United States Patent [19]
Belfort

[11] Patent Number: 5,795,731
[45] Date of Patent: Aug. 18, 1998

[54] INTEINS AS ANTIMICROBIAL TARGETS: GENETIC SCREENS FOR INTEIN FUNCTION

[75] Inventor: Marlene Belfort, Slingerlands, N.Y.

[73] Assignee: Health Research Incorporated, Albany, N.Y.

[21] Appl. No.: 702,902

[22] Filed: Aug. 26, 1996

[51] Int. Cl.$^6$ .............................. C12Q 1/18; C12N 15/00
[52] U.S. Cl. .................. 435/32; 435/69.7; 435/172.3; 435/199
[58] Field of Search ..................... 435/32, 69.7, 199, 435/172.3; 534/199

[56] References Cited

U.S. PATENT DOCUMENTS 5,496,714   3/1996   Comb et al. ........................ 435/69.7

OTHER PUBLICATIONS

West et al "Cloning & Expression of an Intron-deleted phage T4 td gene" J. Biol. Chem. 261(29):13445-13450, 1986.

Davis et al "Protein splicing in Maturation of M. tb Rec A Protein" Cell 71:201-210, 1992.

Anraku, Y. and Hirata, R. (1994) Protozyme: emerging evidence in nature. J. Biochem. 115, 175–178.

Belfort, M., et al. (1995) Prokaryotic introns and inteins: a panoply of form and function. J. Bacteriol. 177, 3897–3903.

Bremer, M., Gimble, F.S., Thorner, J. and Smith, C. (1992). VDE Endonuclease Cleaves *Saccharomyces cerevisiae* Genomic DNA at a Single Site: Physical Mapping of the VMA1 Gene. Nucleic Acids Res. 20, 5484.

Chong, S., Shao, Y., Paulus, H., Benner, J., Perler, F.B., and Xu, M. (1996) Protein splicing involving the *Saccharomyces cerevisiae* VMA intein: The steps in the splicing pathway, side reactions leading to protein cleavage and establishment of an in vitro splicing system (submitted).

Clarke, N.D. (1994) A proposed mechanism for the self-splicing of proteins. Proc. Natl. Acad. Sci. USA 91, 11084–11088.

Clyman. (1995) Some Microbes have splicing proteins. ASM News 61, 344–347.

Colston, M.J., and Davis E.O. (1994). The ins and outs of protein splicing elements. Molecular Microbiology 12, 359–363.

Cooper, A.A., Chen, Y., Lindorfer, M.A. and Stevens, T.H. (1993). Protein splicing of the yeast TFP1 intervening protein sequence: a model for self-excision. EMBO J. 12, 2575–2583.

Cooper, A.A., and Stevens, T.H. (1993). Protein splicing: Excision of intervening sequences at the protein level. BioEssays 15, 667–673.

Cooper, A.A., and Stevens, T.H. (1995) Protein splicing: Self-splicing of genetically mobile elements at the protein level. TIBS 20, 351–357.

Cook, S.N., Jack, W.E., Xiong, X. Danley, L.E., Ellman, F.A., Schultz, P.G. and Noren, C.J. (1995) Photochemically initiated protein splicing. Angew. Chem. Int. Ed. Engel 34, 1620–1630.

Dalgaard, J. (1994) Mobile introns and inteins: friend or foe? Trends Genet 10, 306–7.

Davis, E.O., Jenner, P.J., Brooks, P.C., Colston, M.J. and Sedgwick, S.G. (1992). Protein Splicing in the Maturation of M. Tuberculosis RecA Protein: A Mechanism for Tolerating a Novel Class of Intervening Sequence. Cell. 71, 201–210.

Davis, E.O., Sedgwick, S.G. and Colston, M.J. (1991). Novel Structure of the recA Locus of *Mycobacterium tuberculosis* Implies Processing of the Gene Product. J. Bacteriol. 173, 5653–5662.

Davis, E.O., Thangaraj, J.S., Brooks, P.C., and Colston, M.J. (1994). Evidence of selection for protein introns in the RecAs of pathogenic Mycobacteria. EMBO J. 13, 699–703.

Davis, E.O. and P.J. Jenner. (1995) Protein splicing—the lengths some proteins will go to. Antonie Van Leeuwenhoek 67, 131–137.

Doolittle, R.F. (1993). The comings and goings of homing endonucleases and mobile introns. Proc. Natl. Acad. Sci. USA. 90, 5379–5381.

Doolittle, W.F. and Stoltzfus, A. (1993). Genes-in-pieces revisited. Nature. 361, 403.

Gimble, F.S. and Stephens, B.W. (1995) Substitutions in conserved dodecapeptide motifs that uncouple the DNA binding and DNA cleavage activities of PI-SceI endonuclease. J Biol Chem 270: 5849–56.

Gimble, F.S. and Thorner, J. (1992). Homing of a DNA endonuclease gene by meiotic gene conversion in *Saccharomyces cerevisiae*. Nature. 357, 301–306.

Gimble, F.S. and Thorner, J., (1993). Purification and Characterization of VDE, a Site–Specific Endonuclease from the Yeast *Saccharomyces cerevisiae*. J. Biol. Chem. 268, 21844–21853.

Gu, H.H., Xu, J., Gallagher, M. and Dean, G.E. (1993). Peptide Splicing in the Vacuolar ATPase Subunit A from Candida tropicalis. J. Biol. Chem. 268, 7372–7381.

Hendrix, W.W. (1991). Protein carpentry. Current Biology. 1,71–73.

Hirata, R. and Anraku, Y. (1992). Mutations at the Putative Junction Sites of the Yeast VMA1 Protein, the Catalytic Subunit of the Vacuolar Membrane H+–ATPase, Inhibit its Processing by Protein Splicing. Biochem. Biophys. Res. Comm. 188, 40–47.

Hirata, R., Ohsumi, Y., Nakano, A., Kawasaki, H., Suzuki, K. and Anraku, Y. (1990). Molecular Structure of a Gene, VMA1, Encoding the Catalytic Subunit of H+–Translocating Adenosine Triphosphatase from Vacuolar Membranes of *Saccharomyces cereviaiae*. J. Biol. Chem. 265, 6726–6733.

(List continued on next page.)

*Primary Examiner*—James C. Housel
*Assistant Examiner*—Rodney P. Swartz
*Attorney, Agent, or Firm*—Frommer Lawrence & Haug LLP; William S. Frommer; Thomas J. Kowalski

[57] ABSTRACT

The present invention relates to testing the efficacy of antimicrobial agents which inhibit intein function through genetic screens for monitoring the function of protein inteins, and isolating conditional mutants thereof.

24 Claims, 36 Drawing Sheets

OTHER PUBLICATIONS

Hodges, R.A., Perler, F.B., Noren, C.J. and Jack, W.E. (1992). Protein splicing removes intervening sequences in an archaea DNA polymerase. Nucleic Acids Res. 20, 6153–6157.

Kane, P.M., Yamashiro, C.T., Wolczyk, D.F., Neff, N., Goebl, M. and Stevens, T.H. (1990). Protein Splicing Converts the Yeast TFP1 Gene Product to the 69–kD Subunit of the Vacuolar H+–Adenosine Triphosphatase Science 250, 651–657.

Koonin, E.V. (1995) A protein splice–junction motif in hedgehog family proteins. Trends Biochem. Sci. 20, 41–142.

Kumar, R.A., Vaze, M.B., Chandra. N.R., Vijayan, M. and Muniyappa, K. (1996) Functional characterization of the precursor and spliced forms of recA protein of *Mycobacterium tuberculosis*. Biochemistry. 35, 1793–1802.

Lambowitz, A.M. and Belfort, M. (1993). Introns as mobile genetic elements. Annu. Rev. Biochem. 62, 587–622.

Mueller, J.E., Bryk, M., Loizos, N. and Belfort, M. (1994). Homing Endonucleases. In, Nucleases, eds., Linn, S.M., Lloyd, R.S. Roberts, R.J. (Cold Spring Harbor Press) Cold Spring Harbor, NY. pp. 111–143.

Neff, N.F. (1993) Protein Splicing: selfish genes invade cellular proteins. Current Opinion in Cell Biology. 5,971–976.

Perler, F.B., Comb, D.G., Jack, W.E., Moran, L.S., Qiang, B., Kucera, R.B., Benner, J., Slatko, B.E., Nwankwo, D.O., Hempstead, S.K., Carlow, C.K.S. and Jannasch, H. (1992). Intervening sequences in an Archaea DNA polymerase gene. Proc. Natl. Acad. Sci. USA. 89, 5577–5581.

Perler, F.B., Davis, E.O., Dean, G.E., Gimble F.S., Jack, W.E., Neff, N., Noren, C.J., Thorner, J., and Belfort, M. (19940. Protein splicing elements: inteins and exteins—a definition of terms and recommended nomenclature. Nucleic Acids Res. 22, 1125–1127.

Pietrokovski, S. (1994) Conserved sequence features of inteins (protein introns) and their use in identifying new inteins and related proteins. Protein Science 3,2340–2350.

Shao, Y., Xu, M.–Q. and Paulus, H. (1995) Protein splicing: Characterization of the aminosuccinimide residue at the carboxyl terminus of the excised intervening sequence. Biochemistry 34, 10844–10850.

Shao, Y., Xu, M.–Q. and Paulus, H. (1996) Protein splicing: Evidence for an N–O acyl rearrangement as the initial step in the splicing process. Biochemistry 35, 3810–3815.

Shub, D.A. and Goodrich–Blair, H. (1992). Protein Introns: A New Home for Endonucleases. Cell. 71, 183–186.

Thony–Meyer, L., A. Bock, and H. Hennecke. (1992) Prokaryotic polyprotein precursors. FEBS Lett. 307, 62–5.

Xu, M., Southworth, M.W., Mersha, F.B., Hornstra, L.J., and Perler, F.B. (1993). In vitro protein splicing of purified precursor and the identification of a branched intermediate. Cell 75, 1371–1377.

Xu, M., Comb, D.G., Paulus, H., Noren, C.J., Shao, Y., and Perler, F.B. (1994). Protein splicing: an analysis of the branched intermediate and its resolution by succinimide formation. EMBO J 13, 5517–22.

Xu, M., and Perler, F.B. (1996) The Mechanism of protein splicing and its modulation by Mutation. EMBO J (in press).

Wallace, C.J.A. (1993). The curious case of protein splicing: Mechanistic insights suggested by protein semisynthesis. Protein Science. 2, 697–705.

Pietrokovski, S. Conserved sequence features of inteins (protein introns) and their use in identifying new inteins and related proteins. Protein Sci. 3:2340–2350, 1994.

West, D.K., Belfort, M., Maley, G.F., and Maley, F. Cloning and expression of an intron–deleted phage T4 td gene. J. Biol. Chem. 261:13446–13450, 1986.

Xu, M., Southworth, M.W., Mersha, F.B., Hornstra, L.J., and Perler, F.B. In vitro protein splicing of purified precursor and the identification of a branched intermediate. Cell 75:1371–1377, 1993.

Xu, M. and Perler, F.B. The mechanisms of protein splicing and its modulation by mutation. EMBO J. 1996. (In Press).

Zhou, Y., Zhang, X., and Ebright, R.H. Random mutagenesis of gene–sized DNA molecules by us of PCR with taq DNA polymerase. Nucleic Acids Res. 19:6052, 1991.

Pietrokovski A new intein in cyanobacteria and its significance for the spread of inteins. Trends in Genetics 12:287–88, 1996.

Fshihi, H., Homing events in the gyrA gene of some mycobacteria. 93: 3410–3415, 1996.

Dalgaard, J.Z., Garret, R.A., and Belfort, M., Purification and characterization of two forms of I–*Dmo*I, a thermophilic site–specific endonuclease encoded by an archaeal intron. 269:28885–28892, 1994.

Orbach, M.J., Porro, E.B., and Yanofsky, C., Cloning and characterization of the Gene for β–tubulin from a benomyl–resistant mutant of *Neurospora crassa* and its use as a dominant selectable marker. 6:2452–2461, 1986.

Fragapane, P., Prislei, S., Michienzi, A., Caffarelli, E., and Bozzoni, I., A novel small nucleolar RNA (U16) is encoded inside a ribosomal protein intron and originates by processing of the pre–mRNA. 12:2921–2928, 1993.

Belfort, M., Ehrenman, K., and Chandry, P.S., Genetic and Molecular Analysis of RNA Splicing in *Escherichia coli*. 181:521–539, 1990.

Belfort, M., Moelleken, A., Maley, G.F., and Maley, F., Purification and properties of T4 phage Thymidylate synthetase produced by the cloned gene in an amplification vector. 258:2045–2051, 1983.

Fsihi, H., De Rossi, E., Salazar, L., Cantoni, R., Labo, M., Riccardi, G., Takiff, H.E., Eiglmeier, K., Bergh, S., and Cole, S.T., Gene arrangement and organization in a ~76 kb fragment encompassing the oriC region of the chromosome of *mycobacterium leprae*. 142:3147–3161, 1996.

Kawasaki, M., Makino, S., Matsuzawa, H., Satow, Y., Ohya, Y., and Anraku, Y., Folding–dependent in vitro protein splicing of the *saccharomyces cerevisiae* VMA1 protozyme. 222:827–832, 1996.

Splicing of intein-TS fusion

A. N-TS, C-TS = TS exteins interrupted by intein

Phenotype of Intein-TS fusion

| VARIANT | PHENOTYPE | GROWTH ON | | |
|---|---|---|---|---|
| | | +THY | -THY | TTM |
| Wild type | TS⁺ | + | + | - |
| Mutant | TS⁻ | + | - | + |

+ = growth     - = no growth

B. +THY, -THY, TTM = media supplements

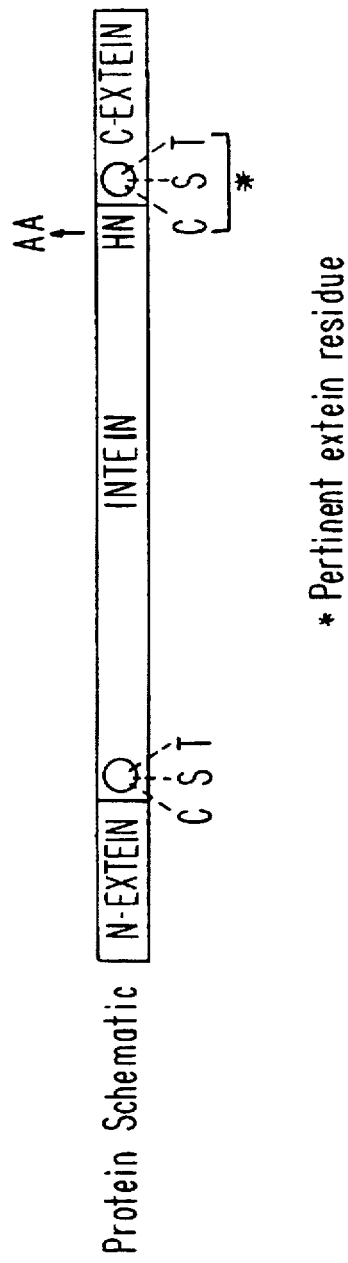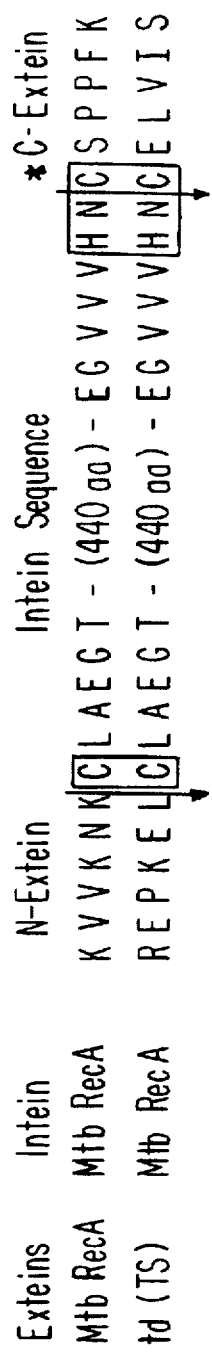
FIG. 2A
FIG. 2B

GROWTH PHENOTYPES b = pKKtdC238(no intein)

c = pKKtdC238Mtb d = pKKtdC238MtbAA(splicing defective intein)

e = pKKtdC238Mtb-ts (temperature sensitive intein mutant)

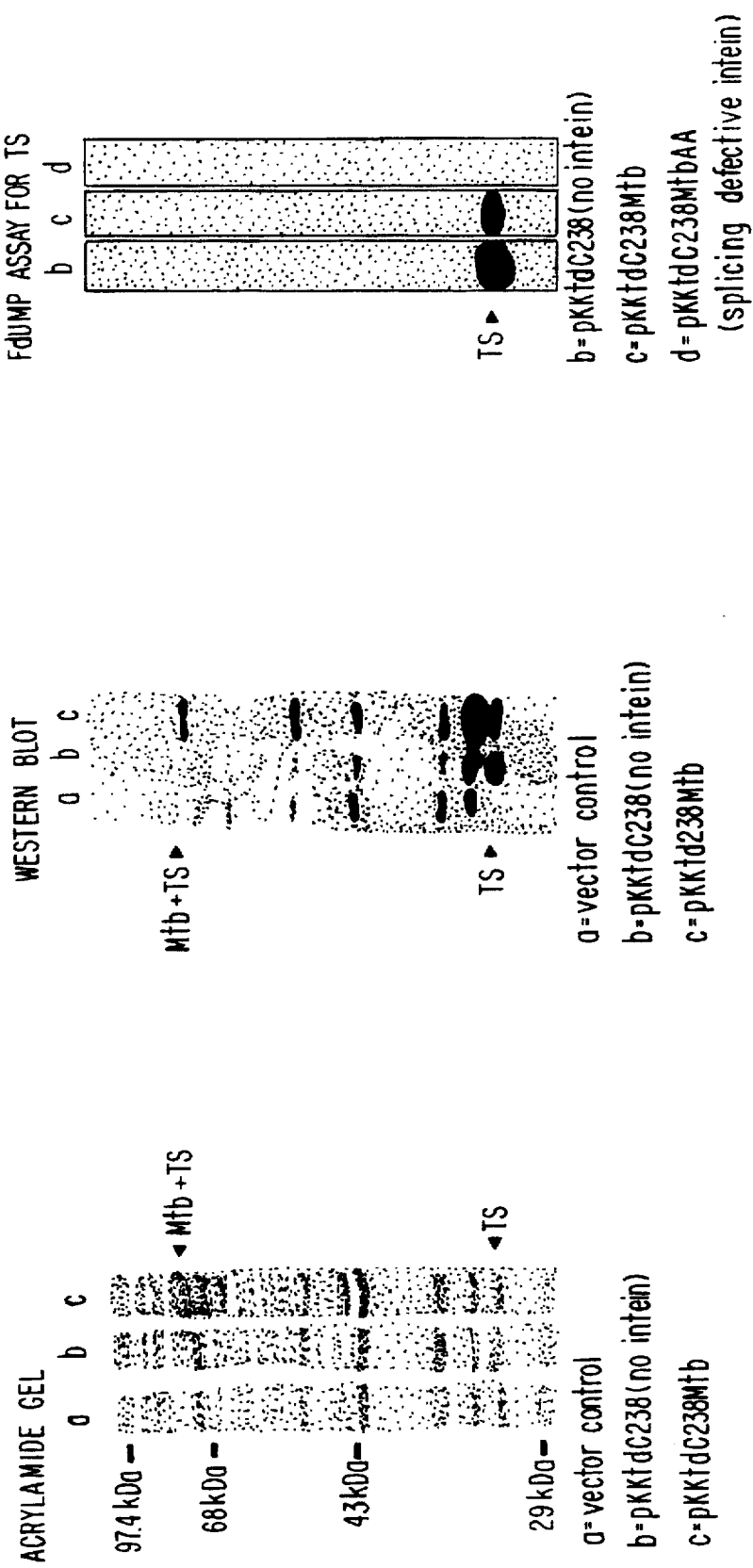

FIG. 5B

```
DNA sequence     861 b.p.      ATGAAACAATAC ... ATGGCGGTGTAA    linear 1         10         20         30         40         50         60
            |          |          |          |          |          |          |
  1 ATGAAACAAT ACCAAGATTT AATTAAAGAC ATTTTTGAAA ATGGTTATGA AACCGATGAT  60
 61 CGTACAGGCA CAGGAACAAT TGCTCTGTTC GGATCTAAAT TACGCTGGA TTTAACTAAA 120
121 GGTTTTCCTG CGTAACAAC TAAGAAGCTC GCCTGCATTGC CTTGCATTGC TGAGCTAATA 180
181 TGTTTTTAT CAGGAAGCAC AAATGTCAAC GATTACGAT TAATTCAACA CGATTCGTTA 240
241 ATCCAAGGCA AAACAGTCTG GGATGAAAT TACGAAAATC AAGCAAAGA TTTAGGATAC 300
301 CATAGCGGTG AACTTGGTCC AATTTATGGA AAACAGTGGC GTGATTTTGG TGGTGTAGAC 360
361 CAAATTATAG AAGTTATTGA TCGTATTAAA AAACTGCCAA ATGATAGGCG TCAAATTGTT 420
421 TCTGCATGGA ATCCAGTGA ACTTAATATAT ATGGCATTAC CGCCTTGTCA TATGTTTCTAT 480
481 CAGTTTAATG TGCGTAATGG CTATTTGGAT TTGCAGTGGT ATCAACGCTC AGTAGATGTT 540
541 TTCTTGGGTC TACGTTTAA TATGCTACGT TAGTTCATAT TGTAGCTAAG 600
601 ATGTGTAATC TTAATTCCAGG GGATTTGATA TTTTCTGTG TAATACTCA TATCTATATG 660
661 AATCACGTAG AACAATGTAA AGAAATTTTG AGGCGTGAAC CTAAAGAGCT TTGTGAGCTG 720
721 GTAATAAGTG GTCTACCTTA TAAATTCCGA TATCTTCTA CTAAGAACA ATTAAAATAT 780
781 GTTCTTAAAC TTAGCCTAA AGATTTCGTT CTTAACAACT AGTATCACA CCCTCCTATT 840
841 AAAGGAAAGA TGGCGGTGTA A                                            861
```

FIG. 6B-1

```
DNA sequence    3253 b.p.    GCTCCTAATTAC ... CGACTCACTATA    circular 10         20         30         40         50         60
          |          |          |          |          |          |
   1 GCTCCTAATT ACTTATTTAC TTATTTTTC GTAGGACTAT CACCTAACTA ACGGGGGCGA    60
  61 ATTCGAGCTC GGTACCCGGG GATCCTCTAG AGTCGACCTG CAGGCATGCA AGCTTGAGTA   120
 121 TTCTATAGTG TCACCTAAAT AGCTTGGCGT AATCATGGTC ATAGCTGTTT CCTGTGTGAA   180
 181 ATTGTTATCC GCTCACAATT CCACACAACA TACGAGCCGG AAGCATAAAG TGTAAAGCCT   240
 241 GGGGTGCCTA ATGAGTGAGC TAACTCACAT TAATTGCGTT GCGCTCACTG CCCGCTTTCC   300
 301 AGTCGGGAAA CCTGTCGTGC CAGCTGCATT AATGAATCGG CCAACGCGCG GGGAGAGGCG   360
 361 GTTTGCGTAT TGGGCGCTCT TCCGCTTCCT CGCTCACTGA CTCGCTGCGC TCGGTCGTTC   420
 421 GGCTGCGGCG AGCGGTATCA GCTCACTCAA AGGCGGTAAT ACGGTTATCC ACAGAATCAG   480
 481 GGGATAACGC AGGAAAGAAC ATGTGAGCAA AAGGCCAGCA AAAGGCCAGG AACCGTAAAA   540
 541 AGGCCGCGTT GCTGGCGTTT TTCCATAGGC TCCGCCCCCC TGACGAGCAT CACAAAAATC   600
 601 GACGCTCAAG TCAGAGGTGG CGAAACCCGA CAGGACTATA AAGATACCAG GCGTTTCCCC   660
 661 CTGGAAGCTC CCTCGTGCGC TCTCCTGTTC CGACCCTGCC GCTTACCGGA TACCTGTCCG   720
 721 CCTTTCTCCC TTCGGGAAGC GTGGCGCTTT CTCATAGCTC ACGCTGTAGG TATCTCAGTT   780
 781 CGGTGTAGGT CGTTCGCTCC AAGCTGGGCT GTGTGCACGA ACCCCCCGTT CAGCCCGACC   840
 841 GCTGCGCCTT ATCCGGTAAC TATCGTCTTG AGTCCAACCC GGTAAGACAC GACTTATCGC   900
 901 CACTGGCAGC AGCCACTGGT AACAGGATTA GCAGAGCGAG GTATGTAGGC GGTGCTACAG   960
 961 AGTTCTTGAA GTGGTGGCCT AACTACGGCT ACACTAGAAG GACAGTATTT GGTATCTGCG  1020
1021 CTCTGCTGAA GCCAGTTACC TTCGGAAAAA GAGTTGGTAG CTCTTGATCC GGCAAACAAA  1080
```

FIG. 6B-2

```
1081 CCACCGCTGG TAGCGGTGGT TTTTTGTTT GCAAGCAGCA GATTACGCGC AGAAAAAAAG 1140
1141 GATCTCAAGA AGATCCTTTG ATCTTTTCTA CGGGGTCTGA CGCTCAGTGG AACGAAAACT 1200
1201 CACGTTAAGG GATTTTGGTC ATGAGATTAT CAAAAGGAT CTTCACCTAG ATCCTTTTAA 1260
1261 ATTAAAATG AAGTTTTAAA TCAATCTAAA GTATATATGA GTAAACTTGG TCTGACAGTT 1320
1321 ACCAATGCTT AATCAGTGAG GCACCTATCT CAGCGATCTG TCTATTTCGT TCATCCATAG 1380
1381 TTGCCTGACT CCCCGTCGTG TAGATAACTA CGATACGGGA GGGCTTACCA TCTGGCCCCA 1440
1441 GTGCTGCAAT GATACCGCGA GACCCACGCT CACCGGCTCC AGATTTATCA GCAATAAACC 1500
1501 AGCCAGCCGG AAGGGCCGAG CGCAGAAGTG GTCCTGCAAC TTTATCCGCC TCCATCCAGT 1560
1561 CTATTAATTG TTGCCGGGAA GCTAGAGTAA GTAGTTCGCC AGTTAATAGT TTGCGCAACG 1620
1621 TTGTTGCCAT TGCTACAGGC ATCGTGGTGT CACGCTCGTC GTTTGGTATG GCTTCATTCA 1680
1681 GCTCCGGTTC CCAACGATCA AGGCGAGTTA CATGATCCCC CATGTTGTGC AAAAAGCGG 1740
1741 TTAGCTCCTT CGGTCCTCCG ATCGTTGTCA GAAGTAAGTT GGCCGCAGTG TTATCACTCA 1800
1801 TGGTTATGGC AGCACTGCAT AATTCTCTTA CTGTCATGCC ATCCGTAAGA TGCTTTTCTG 1860
1861 TGACTGGTGA GTACTCAACC AAGTCATTCT GAGAATAGTG TATGCGGCGA CCGAGTTGCT 1920
1921 CTTGCCCGGC GTCAATACGG GATAATACCG CGCCACATAG CAGAACTTTA AAAGTGCTCA 1980
1981 TCATTGGAAA ACGTTCTTCG GGGCGAAAAC TCTCAAGGAT CTTACCGCTG TTGAGATCCA 2040
2041 GTTCGATGTA ACCCACTCGT GCACCCAACT GATCTTCAGC ATCTTTTACT TTCACCAGCG 2100
2101 TTTCTGGGTG AGCAAAAACA GGAAGGCAAA ATGCCGCAAA AAAGGGAATA AGGGCGACAC 2160
2161 GGAAATGTTG AATACTCATA CTCTTCCTTT TTCAATATTA TTGAAGCATT TATCAGGGTT 2220
```

FIG.6B-3

```
2221 ATTGTCTCAT GAGCGGATAC ATATTTGAAT GTATTTAGAA AAATAAACAA ATAGGGGTTC 2280
2281 CGCGCACATT TCCCCGAAAA GTGCCACCTG ACGTCTAAGA AACCATTATT ATCATGACAT 2340
2341 TAACCTATAA AATAGGCGT ATCACGAGGC CCTTCGTCT CGGGCGTTTC GGTGATGACG 2400
2401 GTGAAAACCT CTGACACATG CAGCTCCCGG AGACGGTCAC AGCTTGTCTG TAAGCGGATG 2460
2461 CCGGGAGCAG ACAAGCCCGT CAGGGCGCGT CAGGGGGTGT TGGCGGGTGT CGGGGCTGGC 2520
2521 TTAACTATGC GGCATCAGAG CAGATTGTAC CCATATGCGG TGTGAAATAC CGGCGCATTA 2580
2581 CGCACAGATG CGTAAGGAGA AAATACCGCA TCAGGCGACG CGCCCTGTAG CGGCGCATTA 2640
2641 AGCGCGGCGG GTGTGGTGGT TACGCGCAGC GTGACCGCTA CACTTGCCAG CGCCCTAGCG 2700
2701 CCCGCTCCTT TCGCTTTCTT CCCTTCCTTT CTCGCCACGT TCGCCGGCTT TCCCCGTCAA 2760
2761 GCTCTAAATC GGGGGCTCCC TTTAGGGTTC CGATTTAGAG CTTTACGGCA CCTCGACCGC 2820
2821 AAAAAACTTG ATTTGGGTGA TGGTTCACGT AGTGGGCCAT CGCCCTGATA GACGGTTTT 2880
2881 CGCCCTTTGA CGTTGGAGTC CACGTTCTTT AATAGTGGAC TCTTGTTCCA AACTGGAACA 2940
2941 ACACTCAACC CTATCTCGGT CTATTCTTTT GATTTATAAG GGATTTTGCC GATTTCGGCC 3000
3001 TATTGGTTAA AAAATGAGCT GATTTAACAA ATATTTAACG CGAATTTAA CAAAATATTA 3060
3061 ACGTTTACAA TTTCCATTCG CCATTCAGGC TGCGCAACTG TTGGGAAGGG CGATCGGTGC 3120
3121 GGGCCTCTTC GCTATTACGC CAGCTGGCGA AAGGGGGATG TGCTGCAAGG CGATTAAGTT 3180
3181 GGGTAACGCC AGGGTTTTCC CAGTCACGAC GTTGTAAAAC GACGGCCAGT GAATTGTAAT 3240
3241 ACGACTCACT ATA                                                   3253
          |         |         |         |         |         |
         10        20        30        40        50        60
```

FIG. 7B-1

DNA sequence     4586 b.p.     TTCTGTTTCCTG ... GATCCCCGGGAA  circular

```
               1          10         20         30         40         50         60
               |          |          |          |          |          |          |
   1   TTCTGTTTCC TGTGTGAAAT TGTTATCCGC TCACAATTCC ACACATTATA CGAGCCGATG    60
  61   ATTAATTGTC AACAGCTCAT TTCAGAATAT TTGCCAGAAC CGTTATGATG TCGGGCAAA    120
 121   AAACATTATC CAGAACGGGA GTGCGCCTTG AGGACACGA ATTATGCAGT GATTACGAC    180
 181   CTGCACAGCC ATACCACAGC TTCCGATGGC TGCCTGACGC CAGAAGCATT GGTGCACCGT   240
 241   GCAGTCGATA AGCTCCGGAT CCTCTACGCC GGACCATCG TGCCCGGCAT CACCGGCGCC   300
 301   ACAGGTGCGG TTGCTGGGCC CTATATCGCC GACATCACCG ATGGGAAGA TCGGGCTCGC   360
 361   CACTTCGGGC TCATGAGCGC TTGTTTCGGC GTGGGTATGG TGGCAGGCC CGTGCCCGGG   420
 421   GGACTGTTGG GCGCCATCTC CTTGCATGCA CCATTCCTTG CGGCGGCGT GCTCAACGGC   480
 481   CTCAACCTAC TACTGGGCTG CTTCCTAATG CAGGAGTCGC ATAAGGAGA GCGTCGACCG   540
 541   ATGCCCTTGA GAGCCTTCAA CCCAGTCAGC TCCTTCCGGT GGGCGGGGG CATGACTATC   600
 601   GTCGCCGCAC TTATGACTGT CTCTCTTTATC ATGCAACTCG TAGGACAGGT GCCGGCAGCG   660
 661   CTCTGGGTCA TTTTCGGCGA GGACCGCTTT CGCTGGAGCG CGACGATGAT CGGCCTGTCG   720
 721   CTTGCGGTAT TCGGAATCTT GCACGCCCTC TGTCACTGG TCCCGCCACC TCCCGCCACC   780
 781   AAACGTTTCG GCGAGAAGCA GGCCATTATC GCCGCATGG CGCCGACCG GCTGGCTAC    840
 841   GTCTTGCTGG CGTTCGGGAC GCGAGGCTGG ATGGCCTTCC CCATTATGAT TCTTCTCGCT   900
 901   TCCGGCGGCA TCGGCGGATGCC CGCGGTTGCAG GCCATGCTGT CCAGGCAGT AGATGACGAC   960
 961   CATCAGGGAC AGCTTCAAGG ATCGCTCGCG GCTCTTACCA GCCTAACTTC GATCACTGA    1020
1021   CCGCTGATCG TCACGGGCGAT TTATGCCGCC TGGGCGAGCA CATGGAACGG GTTGGCATGG   1080
1081   ATTGTAGGCG CCGCCCTATA CCTTGTCTGC CTCCCGCGT TGCGTCGCGG TGCATGGAGC   1140
1141   CGGGCCACCT CGACCTGAAT GGAAGCGGC GGCACCTCGC TAACGGATTC ACCACTCCAA   1200
1201   GAATTGGAGC CAATCAATTC TTGCGGAGAA CTGTGAATGC GCAAACCAAC CCTTGGCAGA   1260
1261   ACATATCCAT CGCGTCCGCC ATCTCCAGCA GCCGCACGCG GCGCATCTCG GCAGGGTTG   1320
1321   GGTCCTGGCC ACGGCGTGCG ATGATCGTGC TCCTGTCGTT GAGGACCCGG CTAGGCTGGC   1380
1381   GGGGTTGCCT TACTGGTTAG CAGAATGAAT CACCGATACG CGAGCGAACG TGAAGCGACT   1440
```

FIG. 7B-2

```
1441 GCTGCTGCAA AACGTCTGCG ACCTGAGCAA CAACATGAAT GGTCTTCGGT TTCCGTGTTT 1500
1501 CGTAAAGTCT GGAAACGCGG AAGTCAGCGC CCTGCACCAT TATGTTCCGG ATCTGCATCG 1560
1561 CAGGATGCTG CTGGCTACCC TGTGAACAC CTACATCTGT ATTAACGAAG CGCTGGCATT 1620
1621 GACCCTGAGT GATTTTTCTC TGTCCCCGCC GCATCCATAC CGCCAGTTGT TTACCCTCAC 1680
1681 AACGTTCCAG TAACCGGGCA TGTTCATCAT CAGTAACCCG TATCGTGAGC ATCCTCTCTC 1740
1741 GTTTCATCGG TATCATTACC CCCATGAACA CTTACACGGA GGCATCAAGT 1800
1801 GACCAAACAG GAAAAAACCG CCCTTAACAT GGCCCGCTTT ATCAGAAGCC AGACATTAAC 1860
1861 GCTTCTGGAG AAACTCAACG AGCTGGACGC GGATGAACAG GCAGACATCT GTGAATCGCT 1920
1921 TCACGACCAC GCTGATGAGC CTGCCTCGCG CGTTTCGGTG ATGACGGTGA 1980
1981 AAACCTCTGA CACATGCAAG TCCGGAGAC GGTCACAGCT TGTCTGTAAG CGGATGCCGG 2040
2041 GAGCAGACAA GCCCGTCAGG GCGCGTCAGC GGGTGTTGGC GGGTGTCGGG GCGCAGCCAT 2100
2101 GACCCAGTCA CGTAGCGATA GCGGAGTGTA TACTGGCTTA ACTATGCGGC ATCAGAGCAG 2160
2161 ATTGTACTGA GAGTGCACCA TATGCGGTGT GAAATACCGC ACAGATGCGT AAGGAGAAAA 2220
2221 TACCGCATCA GGGCGCTCTTC CGCTTCCTCG CTCACTGACT CGCTGCGCTC GGTCGTTCGG 2280
2281 CTGCGGCGAG CGGTATCAGC TCACTCAAAG GCGGTAATAC GGTTATCCAC AGAATCAGGG 2340
2341 GATAACGCAG GAAAGAACAT GTGAGCAAAA AGGCCAGCAA CCGTAAAAAG 2400
2401 GCCGCGTTGC TGGCGTTTTT CCATAGGCTC CGCCCCCCTG ACGAGCATCA CAAAAATCGA 2460
2461 CGCTCAAGTC AGAGGTGGCG AAACCCGACA GGACTATAAA GATACCAGGC GTTTCCCCCT 2520
2521 GGAAGCTCCC TCGTGCGCTC TCCTGTTCCG ACCCTGCCGC TTACCGGATA CCTGTCCGCC 2580
2581 TTTCTCCCTT CGGGAAGCGT GGCGCTTTCT CATAGCTCAC GCTGTAGGTA TCTCAGTTCG 2640
```

FIG. 7B-3

```
2641 GTGTAGGTCG TTCGCTCCAA GCTGGGCTGT GTGCACGAAC CCCCGTCA GCCCGACCGC 2700
2701 TGCGCCTTAT CGGTAACTA TCGTCTTGAG TCCAACCCGG TAAGACACGA CTTATCGCCA 2760
2761 CTGGCAGCAG CCACTGGTAA CAGGATTAGC AGAGGAGGT ATGTAGGCGG TGCTACAGAG 2820
2821 TTCTTGAAGT GGTGGCCTAA CTACGGCTAC ACTAGAAGGA CAGTATTTGG TATCTGCGCT 2880
2881 CTGCTGAAGC CAGTTACCTT CGGAAAAAGA GTTGGTAGCT CTTGATCCGG CAAACAAACC 2940
2941 ACCGCTGGTA GCGGTGGTTT TTTTGTTTGC AAGCAGCAGA TTACGCGCAG AAAAAAAGGA 3000
3001 TCTCAAGAAG ATCCTTTGAT CTTTTCTACG GGGTCTGACG CTCAGTGGAA CGAAAACTCA 3060
3061 CGTTAAGGGA TTTTGGTCAT GAGATTATCA AAAAGGATCT TCACCTAGAT CCTTTTAAAT 3120
3121 TAAAAATGAA GTTTTAAATC AATCTAAAGT ATATATGAGT AAACTTGGTC TGACAGTTAC 3180
3181 CAATGCTTAA TCAGTGAGGC ACCTATCTCA GCGATCTGTC TATTTCGTTC ATCCATAGTT 3240
3241 GCCTGACTCC CCGTCGTGTA GATAACTACG GGTTACCATC TGGCCCCAGT 3300
3301 GCTGCAATGA TACCGCGAGA CCCACGCTCA ATACGGGAGG GCTTACGTC ATTTATCAGC AATAAACCAG 3360
3361 CCAGCCGGAA GGGCCGAGCG CAGAAGTGGT CCTGCAACTT TATCCGCCTC CATCCAGTCT 3420
3421 ATTAATTGTT GCCGGGAAGC TAGAGTAAGT AGTTCGCCAG TTAATAGTTT GCGCAACGTT 3480
3481 GTTGCCATTG CTACAGGCAT CGTGGTGTCA CGCTCGTCGT TTGGTATGGC TTCATTCAGC 3540
3541 TCCGGTTCCC AACGATCAAG GCGAGTTACA TGATCCCCCA TGTTGTGCAA AAAAGCGGTT 3600
3601 AGCTCCTTCG GTCCTCCGAT CGTTGTCAGA AGTAAGTTGG CCGCAGTGTT ATCACTCATG 3660
3661 GTTATGGCAG CACTGCATAA TTCTCTTACT GTCATGCCAT CCGTAAGATG CTTTTCTGTG 3720
3721 ACTGGTGAGT ACTCAACCAA GTCATTCTGA GAATAGTGTA TGCGGCGACC GAGTTGCTCT 3780
```

FIG. 7B-4

```
3781 TGCCGGCGT CAACACGGGA TAATACCGCG GAACTTTAAA AGTGCTCATC 3840
3841 ATTGGAAAAC GTTCTTCGGG GCGAAAACTC TCAAGGATCT GAGATCCAGT 3900
3901 TCGATGTAAC CCACTCGTGC ACCCAACTGA TCTTCAGCAT CACCAGCGTT 3960
3961 TCTGGGTGAG CAAAAACAGG AAGGCAAAAT GCCGCAAAAA GGGAATAAG GGCGACACGG 4020
4021 AAATGTTGAA TACTCATACT CTTCCTTTTT CAATATTATT GAAGCATTTA TCAGGGTTAT 4080
4081 TGTCTCATGA GCGGATACAT ATTTGAATGT ATTTAGAAAA ATAAACAAAA GAGTTTGTAG 4140
4141 AAACGCAAAA AGGCCATCCG TCAGGATGGC CTTCTGCTTA ATTTGATGCC TGGCAGTTTA 4200
4201 TGGCGGGCGT CCTGCCCGCC ACCCTCCGGG CCGTTGCTTC GCAACGTTCA AATCCGCTCC 4260
4261 CGGCGGATTT GTCCTACTCA GGAGAGCGTT CACCGACAAA CAACAGATAA ACGAAAAGC 4320
4321 CCAGTCTTTC GACTCTTTC TTCGTTTAT TTGATGCCTG GCAGTTTCCCT ACTCTCGCAT 4380
4381 GGGGAGACCC CACACTACCA TCGCCGCTAC GGCGTTTCAC TTCTGAGTTC GGCATGGGGT 4440
4441 CAGGTGGGAC CACCGCGCTA CTGCCGCCAG GCAAATTCTG TTTATCAGA CCGCTTCTGC 4500
4501 GTTCTGATTT AATCTGTATC AGGCTGAAAA TCTTCTCTCA TCCGCCAAAA CAGAAGCTTG 4560
4561 GCTGCAGGTC GACGGATCCC CGGGAA                                      4586
              |         |         |         |         |         |
              10        20        30        40        50        60
```

FIG. 8B-1

DNA sequence    5251 b.p.    GAATTCATGAAA ... ACACAGGAAACA    circular

```
          1          10         20         30         40         50         60
          |          |          |          |          |          |          |
   1  GAATTCATGA AACAATACCA AGATTTAATT AAAGACATTT TTGAAAATGG TTATGAAACC    60
  61  GATGATCGTA CAGGCACAGG AACAATTGCT CTGTTCCGAT CTAAATTACG CTGGGATTTA   120
 121  ACTAAAGGTT TTCCTGCGGT AACAACTAAG AAGCTCGCCT GGAAAGCTTG CATTGCTGAG   180
 181  CTAATATGTT TTTTATCAGG AAGCAAAAG GTCAATGATT TACGATTAAT TCAACACGAT   240
 241  TCGTTAATCC AAGGCAAAAC AGTCTGGGAT GAAAATTACG AAATCAAGC AAAGATTTA   300
 301  GGATACCATA GCGGTGAACT TGGTCCAATT TATGGAAAAC AGTGGCGTGA TTTTGGTGGT   360
 361  GTAGACCAAA TTATAGAAGT TATTGATCGT ATTAAAAAAC TGCCAAATGA TAGGCGTCAA   420
 421  ATGTTTTCTG CATGGAATCC AGCTGAACTT AAATATATGG CATTACCGCC TTGTCATATG   480
 481  TTCTATCAGT TTAATGTGCG TAATGGCTAT TTGGATTTGC AGTGGTATCA ACGCTCAGTA   540
 541  GATGTTTTCT TGGGTCTACC GTTTAATATT GCGTCATATG CTACGTTAGT TCATATTGTA   600
 601  GCTAAGATGT GTAATCTTAT TCCAGGGGAT TTGATATTTT CTGGTGGTAA TACTCATATC   660
 661  TATATGAATC ACGTAGAACA ATGTAAAGAA ATTTTGAGGC GTGAACCTAA AGAGCTCTGT   720
 721  GAACTAGTAA TAAGTGGTCT ACCTTATAAA TTTCTACTAA TTCTACTAA AGAACAATTA   780
 781  AAATATGTTC TTAAACTTAG GCCTAAAGAT GCCTAAAGAT ACAACTATGT ATCACACCCT   840
 841  CCTATTAAAG GAAAGATGGC GGTGTAACTG CAGCCAAGCT TCTGTTTTGG CGGATGAGAG   900
 901  AAGATTTTCA GCCTGATACA GATTAAATCA GAACGCAGAA GCGGTCTGAT AAAACAGAAT   960
 961  TTGCCTGGCG GCAGTAGCGC GGTGGTCCCA CCTGACCCCA TGCCGAACTC AGAAGTGAAA  1020
1021  CGCCGTAGCG CCGATGGTAG TGTGGGGTCT CCCCATGCGA GAGTAGGGAA CTGCCAGGCA  1080
1081  TCAAATAAAA CGAAAGGCTC AGTCGAAAGA CTGGGCCTTT CGTTTTATCT GTTGTTTGTC  1140
1141  GGTGAACGCT CTCCTGAGTA GGACAAATCC GCCGGGAGCG GATTTGAACG TTGCGAAGCA  1200
```

FIG. 8B-2

| | | | | |
|---|---|---|---|---|
| 1201 | ACGGCCCGGA | GGGTGGCGGG | CAGGACGCCC | GCCATAAACT | GCCAGGCATC | AAATTAAGCA | 1260 |
| 1261 | GAAGGCCATC | CTGACGGATG | GCCTTTTTGC | GTTTCTACAA | ACTCTTTTGT | TTATTTTCT | 1320 |
| 1321 | AAATACATTC | AAATATGTAT | CCGCTCATGA | GACAATAACC | CTGATAAATG | CTTCAATAAT | 1380 |
| 1381 | ATTGAAAAAG | GAAGAGTATG | AGTATTCAAC | ATTTCCGTGT | CGCCCTTATT | CCCTTTTTG | 1440 |
| 1441 | CGGCATTTTG | CCTTCCTGTT | TTTGCTCACC | CAGAAACGCT | GGTGAAAGTA | AAAGATGCTG | 1500 |
| 1501 | AAGATCAGTT | GGGTGCACGA | GTGGGTTACA | TCGAACTGGA | TCTCAACAGC | GGTAAGATCC | 1560 |
| 1561 | TTGAGAGTTT | TCGCCCCGAA | GAACGTTTTC | CAATGATGAG | CACTTTTAAA | GTTCTGCTAT | 1620 |
| 1621 | GTGGCGCGGT | ATTATCCCGT | GTTGACGCCG | GGCAAGAGCA | ACTCGGTCGC | CGCATACACT | 1680 |
| 1681 | ATTCTCAGAA | TGACTTGGTT | GAGTACTCAC | CAGTCACAGA | AAAGCATCTT | ACGGATGGCA | 1740 |
| 1741 | TGACAGTAAG | AGAATTATGC | AGTGCTGCCA | TAACCATGAG | TGATAACACT | GCGGCCAACT | 1800 |
| 1801 | TACTTCTGAC | AACGATCGGA | GGACCGAAGG | AGCTAACCGC | TTTTTTGCAC | AACATGGGGG | 1860 |
| 1861 | ATCATGTAAC | TCGCCTTGAT | CGTTGGGAAC | CGGAGCTGAA | TGAAGCCATA | CCAAACGACG | 1920 |
| 1921 | AGCGTGACAC | CACGATGCCT | GTAGCAATGG | CAACAACGTT | GCGCAAACTA | TTAACTGGCG | 1980 |
| 1981 | AACTACTTAC | TCTAGCTTCC | CGGCAACAAT | TAATAGACTG | GATGGAGGCG | GATAAAGTTG | 2040 |
| 2041 | CAGGAGAGCG | TGGGTCTCGC | GGTATCATTG | CAGCACTGGG | GCCAGATGGT | AAGCCCTCCC | 2100 |
| 2101 | GTATCGTAGT | TATCTACACG | ACGGGGAGTC | AGGCAACTAT | GGATGAACGA | AATAGACAGA | 2160 |
| 2161 | TCGCTGAGAT | AGGTGCCTCA | CTGATTAAGC | ATTGGTAACT | GTCAGACCAA | GTTTACTCAT | 2220 |
| 2221 | ATATACTTTA | GATTGATTTA | AAACTTCATT | TTTAATTTAA | AAGGATCTAG | GTGAAGATCC | 2280 |
| 2281 | TTTTTGATAA | TCTCATGACC | AAAATCCCTT | AACGTGAGTT | TTCGTTCCAC | TGAGCGTCAG | 2340 |
| 2341 | ACCCCGTAGA | AAAGATCAAA | GGATCTTCTT | GAGATCCTTT | TTTTCTGCGC | GTAATCTGCT | 2400 |
| 2401 | GCTTGCAAAC | AAAAAAACCA | CCGCTACCAG | CGGTGGTTTG | TTTGCCGGAT | CAAGAGCTAC | 2460 |

FIG. 8B-3

```
2461 CAACTCTTTT TCCGAAGTA ACTGGCTTCA GCAGAGCGCA GATACCAAAT ACTGTCCTTC 2520
2521 TAGTGTAGCC GTAGTTAGGC CACCACTTCA AGAACTCTGT AGCACCGCCT ACATACCTCG 2580
2581 CTCTGCTAAT CCTGTTACCA GTGGCTGCTG CCAGTGGCGA TAAGTCGTGT CTTACCGGGT 2640
2641 TGGACTCAAG ACGATAGTTA CCGGATAAGG GGGCTGAACG GGGGGTTCGT 2700
2701 GCACACAGCC CAGCTTGGAG CGAACGACCT GAGATACCTA CAGGTGAGC 2760
2761 ATTGAGAAAG CGCCACGCTT CCCGAAGGGA CAGGTATCCG GTAAGCGGCA 2820
2821 GGGTCGGAAC AGGAGAGCGC ACGAGGGAGC GAAAGCGCCTGG TATCTTTATA 2880
2881 GTCCTGTCGG GTTTCGCCAC CTCTGACTTG TTCCAGGGGG TTTGTGATGC TCGTCAGGGG 2940
2941 GGCGGAGCCT ATGGAAAAAC GCCAGCAACG AGGGTCGATT ACGGTTCCTG GCCTTTTGCT 3000
3001 GGCCTTTTGC TCACATGTTC TTTCCTGCGT TATCCCCTGA TTCTGTGGAT AACCGTATTA 3060
3061 CCGCCTTTGA GTGAGCTGAT ACCGCTCGCC GCAGCCGAAC GACCGAGCGC AGCGAGTCAG 3120
3121 TGAGCGAGGA AGCGGAAGAG CGCCTGATGC GGTATTTTCT CCTTACGCAT CTGTGCGGTA 3180
3181 TTTCACACCG CATATGGTGC ACTCTCAGTA CAATCTGCTC TGATGCCGCA TAGTTAAGCC 3240
3241 AGTATACACT CCGCTATCGC TACGTGACTG GGTCATGGCT GCGCCCCGAC ACCCGCCAAC 3300
3301 ACCCGTCTCC GGGAGCTGCA TGTGTCAGAG GTTTTCACCG TCATCACCGA AACGCGCGAG 3360
3361 GCAGCTGCGG TAAAGCTCAT CAGGTGGTC GTGAAGCGAT TCACAGATGT CTGCCTGTTC 3420
3421 ATCCGCGTCC AGCTCGTTGA GTTTCTCCAG AAGCGTTAAT GTCTGGCTTC TGATAAAGCG 3480
3481 GGCCATGTTA AGGGCGGTTT TTTCCTGTTT GGTCACTTGA TGCCTCCGTG TAAGGGGGAA 3540
3541 TTTCTGTTCA TGGGGGTAAT GATACCGATG AAACGAGAGA GGATGCTCAC GATACGGGTT 3600
3601 ACTGATGATG AACATGCCCG GTTACTGGAA CGTTGTGAGG GTAAACAACT GCGGGTATGG 3660
3661 ATGCGGCGGG ACCAGAGAAA AATCACTCAG GGTCAATGCC AGCGCTTCGT TAATACAGAT 3720
3721 GTAGGTGTTC CACACGGTAG CCAGCAGCAT CCTGCGATGC AGATCCGGAA CATAATGGTG 3780
```

FIG. 8B-4

```
3781 CAGGGGCTG ACTTCCGCGT TTCCAGACTT TATGAAACAC GGAAACTGGA GACCATTCAT 3840
3841 GTTGTTGCTC AGTCGCAGA CGTTTTGCAG CAGCAGTCGC TTCACGTTCG CTCGGGTATC 3900
3901 GGTGATTCAT TCTGCTAACC AGTAAGGCAA CCCGCCAGC CTAGCCGGGT CCTCAACGAC 3960
3961 AGGAGCACGA TCATGCGCAC CCGTGGCAC TGCCCGAGAT GCGCCGGGTG 4020
4021 CGGCTGCTGG AGATGCGGA CGCGATGGAT ATGTTCTGCC AAGGGTTGGT TTGCGCATTC 4080
4081 ACAGTTCTCC GCAAGAATTG ATTGGCTCCA ATTCTTGAG TGTTGAATCC GTTAGCGAGG 4140
4141 TGCCGCCGGC TTCCATTCAG GTCGAGGTGG CCCGGCTCCA TGCACCGCGA CGCAACGCGG 4200
4201 GGAGGCAGAC AAGGTATAGG GCGGGGCCTA CAACCCGTTC CATGTGCTCG 4260
4261 CCGAGGCGGC ATAAATCGCC GTGACGATCA GCGGTCCAGT GATCGAAGTT AGGCTGGTAA 4320
4321 GAGCCGCGAG CGATCCTCT AGCTGTCCCT GATGGTCGTC ATCTACCTGC CTGACACAGCA 4380
4381 TGGCCTGCAA CGCGGGCATC CCGATGCCGC CGGAAGCGAG AAGAATCATA ATGGGAAGG 4440
4441 CCATCCAGCC TCGCGTCGCG AACGCCAGCA CAGCGCGTCG GCCGCCATGC 4500
4501 CGGCGATAAT GGCCTGCTTC TCGCCGAAAC GTTTGGTGCG ACGAAGGCTT CCTACGAGTT 4560
4561 GAGCGAAGCG GTCCTGCCG AAAATGACCC AGAGGCGTGC CGGCACCTGT CCTACGAGTT 4620
4621 GCATGATAAA GAAGACAGTC ATAAGTGCGG CGACGATAGT CATGCCCCGC GCCACCGGA 4680
4681 AGAGCTGAC TGGGTTGAAG GCTCTCAAGG GCATCGGTCG ACGCTCTCCC TTATGCGACT 4740
4741 CCTGCATTAG GAAGCAGCC AGTAGTAGGT TGAGGCCGTT GAGCGCGCC GCCGCAAGGA 4800
4801 ATGGTGCATG CAAGGAGATG GCGCCAACA GTCCCCCGG CACGGGGCCT GCCACCATAC 4860
4861 CCACGCCCGAA ACAAGCGCTC ATGAGCCCGA AGTGGCGAGC CCGATCTTCC CCATCGGTGA 4920
4921 TGTCGGCGAT ATAGGCGCCA GCAACCGCAC CTGTGGGCGC GGTGATGCCG GCCACGATGC 4980
4981 GTCGGCGTA GAGGATCCGG AGCTTATCGA CTGCACGGTG CACCAATGCT TCTGGCGTCA 5040
5041 GGCAGCCATC GGAAGCTGTG GTATGCTGT GCAGGTCGTA AATCACTGCA TAATTCGTGT 5100
5101 CGCTCAAGGC GCACTCCCGT TCTGGATAAT GTTTTTGCG CCGACATCAT AACGGTTCTG 5160
5161 GCAAATATTC TGAAATGAGC TGTTGACAAT TAATCATCGG CTCGTATAAT GTGTGGAATT 5220
5221 GTGAGCGGAT AACAATTTCA CACAGGAAAC A 5251
          |         |         |         |         |         |
         10        20        30        40        50        60
```

FIG. 9B-1

DNA sequence    6571 b.p.    GAATTCATGAAA ... ACACAGGAAACA    circular

```
              10         20         30         40         50         60
    1  GAATTCATGA AACAATACCA AGATTTAATT AAAGACATTT TTGAAAATGG TTATGAAACC    60
   61  GATGATCGTA CAGGCACAGG AACAATTGCT CTGTTCGGAT CTAAATTACG CTGGGATTTA   120
  121  ACTAAAGGTT TTCCTGCGGT AACAACTAAG AAGCTCGCCT GGAAAGCTTG CATTGCTGAG   180
  181  CTAATATGT TTTTATCAGG AAGCACAAAT GTCAATGATT TACGATTAAT TCAACACGAT   240
  241  TCGTTAATCC AAGGCAAAAC GTCTGGAGAT GAAAATTACG AAAATCAAGC AAAGATTTA   300
  301  GGATACCATA GCGGTGAACT TGGTCCAATT TATGGAAAAC AGTGGCGTGA TTTTGGTGT   360
  361  GTAGACCAAA TTATAGAAGT TATTGATCGT ATTAAAATGA TGCCAAATGA TAGGCGTCAA   420
  421  ATTGTTTCTG CATGGAATCC AGCTGAACTT AAATATATGG CATTACCGCC TTGTCATATG   480
  481  TTCTATCAGT TTAAGTGCG TTAAGTGCG AGTGGTATCA ACGCTCAGTA   540
  541  GATGTTTTCT TGGGTCTACC GTTTAATATT GCGTCATATG CTACGTTAGT TCATATTGTA   600
  601  GCTAAGATGT GTAATCTTAT TCCAGGGGAT TTGATATTTT CTGGTGGTAA TACTCATATC   660
  661  TATATGAATC AGTAGAACA ATGTAAGAA ATTTTGAGGC GTGAACCTAA AGAGCTCTGC   720
  721  CTCGCAGAGG GCACTCGGAT CTTCGATCCG GTCACCGGTA CAACGCATCG CATCGAGGAT   780
  781  GTTGTCGATG GGCGCAAGCC GTGGCTGCTG GTGGCTGTG CCAAGGACGG AACGCTGCAT   840
  841  GCGCGGCCCG TGGTGTCCTG GTTGCACCAG GGAACGCGGG ATGTGATCGG GTTGCGGATC   900
  901  GCCGGTGGCG CCATCGTGTG GGCGACACCC GATCACAAGG TGCTGACAGA GTACGGCTGG   960
  961  CGTGCCGCCG GGAACTCCG CAAGGGAGAC AGGGTGGCGC AACCGCGACG CTTCGATGGA  1020
 1021  TTCGGTGACA GTGCGCCGAT TCCGCCCGGAT CATGCCCCGGC ACTTCATCAA TGTTCAGCGG  1080
 1081  GATGGCAGGG ATGGTTGGGT GGGGGGCAAG ACTCCGATCA ACTTCATCAA TGTTCAGCGG  1140
 1141  GCGCTCATTG ACGACGTGAC GCGAATCGCT GCGACGCTCG GTTGCGCGGC CCATCCGCAG  1200
 1201  GGGCGTATCT CACTCGCGAT CGCTCATCGA CCCGGTGAGC GCAACGGTGT GGCAGACCTT  1250
```

FIG. 9B-2

```
1261 TGTCAGCAGG CCGTATCTA CGGCAAGCTC GGTGGGAGA AGACGATTCC GAATTGGTTC 1320
1321 TTCGAGCCGG ACATCGCGGC CGACATTGTC GGCAATCTGC TCTTCGGCCT GTTCGAAAGC 1380
1381 GACGGGTGGG TGAGCCGGGA ACAGACCGGG GCACTTCGGG TCGGTGTCGG GACGACCTCT 1440
1441 GAACAACTCG CGCATCAGAT TCATTGGCTG CTGCTGCGGT TCGGTGTCGG GAGCACCGTT 1500
1501 CGAGATTACG ATCCGACCCA GAAGCGGCCG AGCATCGTCA ACGGTCGACG GATCCAGAGC 1560
1561 AAACGTCAAG TGTTCGAGGT CCGGATCTCG GTATGGATA ACGTCACGGC ATTCGGGAG 1620
1621 TCAGTTCCCA TGTGGGGCC GCGGGTGCC GCGCTTATCC AGGCGATTCC AGAAGCCACG 1680
1681 CAGGGGCGGC GTCGTGGATC GCAAGCGACA CAGAGATGAC CGATGCCGTG 1740
1741 CTGAATTATC TGGACGAGCG CGGCAGGAGG TATCTGGCTG CCGCGGCCAT GATCGGTGTA 1800
1801 GCTTCCGGGG ACCCCGCGG TGGAATGAAG CAGGTCTTAG GTGCCAGCCG CCTTCGTCGG 1860
1861 GATCGGTGC AGGCGCTCGC TGGAATGAAG CAGGTCTTAG GTGCCAGCCG CCTTCGTCGG 1920
1921 GAAGAACTCC GCTATTCCGT GATCGGAGAA GTGACAAAT TCCTGCACGA CATGCTGGCG 1980
1981 GACCTCGAGG TCGAGGAACT GCACACCCTC GTGCCGCAA CCCGCGGGC ACGAACGTTC 2040
2041 GAACTAGTAA TAAGTGTCT ACCTTATAAA TTCCGATATC GGGTTGTCGT GCACAACTGT 2100
2101 AAATATGTTC TTAAACTTAG GCCTAAAGAT TTCGTTCTTA ACAACTATGT AGAACAATTA 2160
2161 CCTATTAAAG GAAAGATGGC GGTGTAACTG CAGCCAAGCT TCTGTTTTGG ATCACACCCT 2220
2221 AAGATTTCA GCCTGATACA GATTAAATCA CAGCCAGAA GCGGTCTGAT CGGATGAGAG 2280
2281 TTGCCTGGCG GCAGTAGCGC GGTGGTCCCA CCTGACCCCA TGCCGAACTC AAACAGAAT 2340
2341 CGCCGTAGCG CCGATGGTAG TGTGGGGTCT CCCCATGCGA GAGTAGGGAA AGAAGTGAAA 2400
2401 TCAAATAAAA CGAAAGGCTC AGTCGAAAGA CTGGGCCTTT CGTTTATCT CTGCCAGGCA 2460
2461 GGTGAACGCT CTCCTGAGTA GGACAAATCC GCCGGGAGCG GATTTGAACG GTTGTTTGTC 2520
2521 ACGGCCCGGA GGTGGCGGG CAGGACGCCC GCCATAAACT GCCAGGCATC TTGCGAAGCA 2580
2581 GAAGGCCATC CTGACGGATG GCCTTTTTGC GCCATAAACT GCCAGGCATC AAATTAAGCA 2640
2641 AAATACATTC AATATGTAT CCGCTCATGA GTTTCTACAA ACTCTTTGT TTATTTTCT 2700
2701 ATTGAAAAAG GAAGAGTATG ATTTCAAAC CTGATAAATG CGCCCTTATT CTTCAATAAT 2760
2761 CGGCATTTG CCTTCCTGTT TTTGCTCACC CAGAAACGCT GGTGAAAGTA AAAGATGCTG 2820
```

FIG. 9B-3

```
2821 AAGATCAGTT GGGTGCACGA GTGGGTTACA TCGAACTGGA TCTCAACAGC GGTAAGATCC 2880
2881 TTGAGAGTTT TCGCCCCGAA GAACGTTTTC CAATGATGAG CACTTTTAAA GTTCTGCTAT 2940
2941 GTGGCGCGGT ATTATCCCGT GTTGACGCCG GGCAAGAGCA ACTCGGTCGC CGCATACACT 3000
3001 ATTCTCAGAA TGACTTGGTT GAGTACTCAC CAGTCACAGA AAAGCATCTT ACGGATGGCA 3060
3061 TGACAGTAAG AGAATTATGC AGTGCTGCCA TAACCATGAG TGATAACACT GCGGCCAACT 3120
3121 TACTTCTGAC AACGATCGGA GGACCGAAGG AGCTAACCGC TTTTTTGCAC AACATGGGGG 3180
3181 ATCATGTAAC TCGCCTTGAT CGTTGGGAAC CGGAGCTGAA TGAAGCCATA CCAAACGACG 3240
3241 AGGGTGACAC CACGATGCCT GTAGCAATGG CAACAACGTT GCGCAAACTA TTAACTGGCG 3300
3301 AACTACTTAC TCTAGCTTCC CGGCAACAAT TAATAGACTG GATGGAGGCG GATAAAGTTG 3360
3361 CAGGAGAGCG TGGGTCTCGC GGTATCATTG CAGCACTGGG GCCAGATGGT AAGCCCTCCC 3420
3421 GTATCGTAGT TATCTACACG ACGGGGAGTC AGGCAACTAT GGATGAACGA AATAGACAGA 3480
3481 TCGCTGAGAT AGGTGCCTCA CTGATTAAGC ATTGGTAACT GTCAGACCAA GTTTACTCAT 3540
3541 ATATACTTTA GATTGATTTA AAACTTCATT TTTAATTTAA AACGTGAGTT TTCGTTCCAC 3600
3601 TGAGCGTCAG 3660
3601 TTTTTGATAA TCTCATGACC AAAATCCCTT AACGTGAGTT TTCGTTCCAC TGAGCGTCAG 3660
3661 ACCCCGTAGA AAGATCAAA GGATCTTCTT GAGATCCTTT TTTTCTGCGC GTAATCTGCT 3720
3721 GCTTGCAAAC AAAAAAACCA CCGCTACCAG CGGTGGTTTG TTTGCCGGAT CAAGAGCTAC 3780
3781 CAACTCTTTT TCCGAAGGTA ACTGGCTTCA GCAGAGCGCA GATACCAAAT ACTGTCCTTC 3840
3841 TAGTGTAGCC GTAGTTAGGC CACCACTTCA AGAACTCTGT AGCACCGCCT ACATACCTCG 3900
3901 CTCTGCTAAT CCTGTTACCA GTGGCTGCTG CCAGTGGCGA TAAGTCGTGT CTTACCGGGT 3960
3961 TGGACTCAAG ACGATAGTTA CCGGATAAGG CGCAGCGGTC GGGCTGAACG GGGGGTTCGT 4020
4021 GCACACAGCC CAGCTTGGAG CGAACGACCT ACACCGAACT GAGATACCTA CAGCGTGAGC 4080
4081 ATTGAGAAAG CGCCACGCTT CCCGAAGGGA GAAAGGCGGA CAGGTATCCG GTAAGCGGCA 4140
4141 GGGTCGGAAC AGGAGAGCGC ACGAGGGAGC TTCCAGGGGG AAACGCCTGG TATCTTTATA 4200
```

FIG. 9B-4

```
4201 GTCCTGTCGG GTTTCGCCAC CTCTGACTTG AGCGTCGATT TTTGTGATGC TGTCAGGGG  4260
4261 GGCGGAGCCT ATGGAAAAAC GCCAGCAACG CGGCCTTTTT ACGGTTCCTG GCCTTTGCT  4320
4321 GGCCTTTTGC TCACATGTTC TTTCCTGCGT TATCCCCTGA TTCTGTGGAT AACCGTATTA 4380
4381 CCGCCTTTGA GTGAGCTGAT ACCGCTCGCC GCAGCCGAAC GACCGAGCGC AGCGAGTCAG 4440
4441 TGAGCGAGGA AGCGGAAGAG CGCCTGATGC GGTATTTTCT CCTTACGCAT CTGTGCGGTA 4500
4501 TTTCACACCG CATATGGTGC ACTCTCAGTA CAATCTGCTC TGATGCCGCA TAGTTAAGCC 4560
4561 AGTATACACT CCGCTATCGC TACGTGACTG GGTCATGCT GCGCCCCGAC ACCCGCCAAC 4620
4621 ACCCGTCTCC GGGAGCTGCA TGTGTCAGAG GTTTTCACCG TCATCACCGA AACGCGCGAG 4680
4681 GCAGTGCGG TAAAGCTCAT CAGCGTGGTC GTGAAGCGAT TCACAGATGT CTGCCTGTTC 4740
4741 ATCCGCGTCC AGCTCGTTGA GTTTCTCCAG AAGCGTTAAT GTCTGGCTTC TGATAAAGCG 4800
4801 GGCCATGTTA AGGGCGGTTT TTTCCTGTTT GGTCACTTGA TGCCTCCGTG TAAGGGGGAA 4860
4861 TTTCTGTTCA TGGGGGTAAT GATACCGATG AAACGAGAGA GGATGCTCAC GATACGGTT 4920
4921 ACTGATGATG AACATGCCCG GTTACTGGAA CGTTGTGAGG GTAAACAACT GCGGTATGG 4980
4981 ATGCGGGGG ACCAGAGAAA AATCACTCAG GGTCAATGCC AGCGCTTCGT TAATACAGAT 5040
5041 GTAGGTGTTC CACAGGGTAG CCAGCAGCAT CCTGCGATGC AGATCCGGAA CATAATGTG 5100
5101 CAGGGGCGCTG ACTTCCGCGT TTCCAGACTT TACGAAACAC GGAAACCGAA GACCATTCAT 5160
5161 GTTGTTGCTC AGGTCGCAGA CGTTTTGCAG CAGCAGTCGC TTCACGTTCG CTCGCGTATC 5220
5221 GGTGATTCAT TCTGCTAACC AGTAAGGCAA CCCCGCCAGC CTAGCCGGGT CCTCAACGAC 5280
5281 AGGAGCACGA TCATGCGCAC CCGTGGCCAG GACCCAACGC TGCCCGAGAT GCGCCGCGTG 5340
5341 CGGCTGCTGG AGATGCGGA CGCGATGGAT ATGTTCTGCC AAGGGTTGGT TTGCGCATTC 5400
5401 ACAGTTCTCC GCAAGAATTG ATTGGCTCCA ATTCTTGGAG TGGTGAATCC GTTAGCGAGG 5460
```

FIG. 9B-5

```
5461 TGCCGCCGGC TTCCATTCAG GTCGAGGTGG CCCGGCTCCA TGCACCGGGA CGCAACGCGG 5520
5521 GGAGGCAGAC AAGGTATAGG GCGGCGCCTA CAATCCATGC CAACCCGTTC CATGTGCTCG 5580
5581 CCGAGGCGGC ATAAATCGCC GTGACGATCA GCGGTCCAGT GATCGAAGTT AGGCTGGTAA 5640
5641 GAGCCGCGAG CGATCCTTGA AGCTGTCCCT GATGGTCGTC ATCTACCTGC CTGGACAGCA 5700
5701 TGGCCTGCAA CGCGGGCATC CCGATGCCGC CGGAAGCGAG AAGAATCATA ATGGGGAAGG 5760
5761 CCATCCAGCC TCGCGTCGCG AACGCCAGCA AGACGTAGCC CAGCGCGTCG GCCGCCATGC 5820
5821 CGGCGATAAT GGCCTGCTTC TCGCCGAAAC GTTTGGTGC GGGACCAGTG ACGAAGGCTT 5880
5881 GAGCGAAGCG GTCCTCGCCG AAAATGACCC AGAGCGCTGC CGGCACCTGT CCTACGAGTT 5940
5941 GCATGATAAA ATAAGTGCGG CGACGATAGT CATGCCCCGC GCCCACCGGA GCCCACCGGA 6000
6001 AGGAGCTGAC TGGGTTGAAG GCTCTCAAGG GCATCGGTCG ACGCTCTCCC TTATGCGACT 6060
6061 CCTGCATTAG GAAGCAGCCC AGTAGTAGGT TGAGGCCGTT GAGCCACCGC GCCGCAAGGA 6120
6121 ATGGTGCATG CAAGGAGATG GCGCCCAACA GTCCCCCGGC CACGGGGCCT GCCACCATAC 6180
6181 CCACGCCGAA ACAAGCGCTC ATGAGCCCGA AGTGGCGAGC CCGATCTTCC CCATCGGTGA 6240
6241 TGTCGGCGAT ATAGGGCCA GCAACGCCAC CTGTGGGGCC CCGATGCGG GCCACGATGC 6300
6301 GTCCGGGTA GAGGATCCGG AGCTTATCGA CTGCACGGTG CACCAATGCT TCTGGCGTCA 6360
6361 GGCAGCCATC GGAAGCTGTG GTATGGCTGT GCAGTCGTA AATCACTGCA TAATTCGTGT 6420
6421 CGCTCAAGGC GCACTCCCGT TCTGGATAAT GTTTTTTGCG CCGACATCAT AACGGTTCTG 6480
6481 GCAAATATTC TGAAATGAGC TGTTGACAAT TAATCATCGG CTCGTATAAT GTGTGGAATT 6540
6541 GTGAGCGGAT AACAATTTCA CACAGGAAAC A 6571
```

FIG. 10B-1

DNA sequence   6571 b.p.   GAATTCATGAAA ... ACACAGGAAACA   circular

```
              10         20         30         40         50         60
       |          |          |          |          |          |          |
   1  GAATTCATGA AACAATACCA AGATTTAATT AAAGACATTT TTGAAAATGG TTATGAAACC    60
  61  GATGATCGTA CAGGCACAGG AACAATTGCT CTGTTCGGAT CTAAATTACG CTGGGATTTA   120
 121  ACTAAAGGTT TCCTGCGCGT AACAACTAAG AAGCTCGCCT GGAAAGCTTG CATTGCTGAG   180
 181  CTAATATGGT TTTTATCAGG AAGCACAAAT GTCAATGATT TACGATTAAT TCAACACGAT   240
 241  TCGTTAATCC AAGGCAAAAC AGTCTGGGAT GAAAATTACG AAAATCAAGC AAAAGATTTA   300
 301  GGATACCATA GCGGTGAACT TGGTCCAATT TATGAAAAAC AGTGGCGTGA TTTTGGTGGT   360
 361  GTAGACCAAA TTATAGAAGT TATTGATCGT ATTAAAAAAC TGCCAAATGA TAGGCGTCAA   420
 421  ATGTTTCTG CATGGAATCC AGCTGAACTT AAATATATGG CATTACCGCC TTGTCATATG   480
 481  TTCTATCAGT TTAATGTGCG TAATGGCTAT TTGGATTTGC AGTGGTATCA ACGCTCAGTA   540
 541  GATGTTTTCT TGGGTCTACC GTTTAATATT GCGTCATATG CTACGTTAGT TCATATTGTA   600
 601  GCTAAGATGT GTAATCTTAT TCCAGGGGAT TTGATATATT CTGGTGTAA TACTCATATC   660
 661  TATATGAATC ACGTAGAACA ATGTAAAGAA ATTTTGAGGC GTGAACCTAA AGAGCTCTGC   720
 721  CTCGCAGAGG GCACTCGGAT CTTCGATCCG GTCACCGGTA CAACGCATCG CATGCGAGAT   780
 781  GTTGTCGATG GGGCAAGCC TAATCATGTC GTGCTGCTG CCAAGGACGG AACGCTGCAT   840
 841  GCGGGGCCCG TGGTGTCCTG GTTGACCAG GGAACGCGGG ATGTGATCGG GTTGCGGATC   900
 901  GCCGGTGGCG CCATCGTGTG GGCGACACCC GATCACAAGG TGCTGACAGA GTACGGCTGG   960
 961  CGTGCCGCCG GGAACTCCG CAAGGGAGAC AGGGTGGGGC AACCGCGACG CTTCGATGGA  1020
1021  TTCGGTGACA GTGCGCCGAT TCCGGGGGAT CATGCCCGGC TGCTTGGCTA CCTGATCGGA  1080
1081  GATGGCCAGG ATGGTTGGGT GGGGGGCCAAG ACTCCGATCA ACTTCATCAA TGTTCAGCGG  1140
1141  GCGCTCATTG ACGACGTGAC GCGAATCGCT GCGACGCTCG GTTGCGCGGC CCATCCGCAG  1200
1201  GGGCGTATCT CACTCGCGAT CGCTCATGA CCCGGTGAGC GCAACGGTGT GCAGACCTT  1260
1261  TGTCAGCAGG CCGGTATCTA CGGCAAGCTC CGGCAAGCTC AGACGATTCC AGACGATTCC GAATTGGTTC  1320
```

FIG. 10B-2

```
1321 TTCGAGCCGG ACATCGCGGC CGACATTGTC GGCAATCTGC TCTTCGGCCT GTTCGAAAGC 1380
1381 GACGGGTGGG TGAGCCCGGA ACAGACCGGG GCACTTCGGG TCGGTTACAC GACGACCTCT 1440
1441 GAACAACTCG CGCATCAGAT TCATTGGCTG CTGCTCGCGT TCGGTGTCGG GAGCACCGTT 1500
1501 CGAGATTACG ATCCGACCCA GAAGCGGCCG AGCATCGTCA ACGGTCGACG GATCCAGAGC 1560
1561 AAACGTCAAG TGTTCGAGGT CCGGATCTCG AGTGGATA ACGTCACGGC ATTCGGGAG 1620
1621 TCAGTTCCCA TGTGGGGGCC GCGCGGTGCC GGCTTATCC AGGCGATTCC AGAAGCCACG 1680
1681 CAGGGCGGC GTCGTGATC GCAAGCGACA GCGCGGTGAC CAGAGATGAC CGATGCCGTG 1740
1741 CTGAATTATC TGGACGAGCG CGCGAGGAGG CCGCGGCCAT GATCGGTGTA 1800
1801 GCTTCCGGGG ACCCCGCGG TGAATGAAG CAGGTCTTAG GTGCCAGCCG CCTTCGTCGG 1860
1861 GATCGCGTGC AGGCGCTCGC GGATGCCCTG GATGACAAAT TCCTGCACGA CATGCTGGCG 1920
1921 GAAGAACTCC GCTATTCCGT GATCCGAGAA GTGCTGCCAA CGGGGCGGGC ACGAACGTTC 1980
1981 GACCTCGAGG TCGAGGAACT GCACACCCTC GTCGCCGAAG GGTTGTCGT GGCCGCCTGT 2040
2041 GAACTAGTAA TAAGTGGTCT ACCTTATATAA TTCCGATATC TTTCTACTAA AGAACAATTA 2100
2101 AAATATGTTC TTAAACTTAG GCCTAAAGAT TTCGTTCTTA ACAACTATGT ATCACACCCT 2160
2161 CCTATTAAAG GAAAGATGGC GGTGTAACTG CAGCCAAGCT TCTGTTTTGG CGGATGAGAG 2220
2221 AAGATTTCA GCCTGATACA GATTAAATCA GAACGCAGAA GCGGTCTGAT AAAACAGAAT 2280
2281 TTGCCTGGCG GCAGTAGCGC GGTGGTCCCA CCTGACCCTC TGCCGAACTC AGAAGTGAAA 2340
2341 CGGGCTAGCG CCGATGGTAG TGTGGGGTCT CCCCATGCGA GAGTAGGGAA CTGCCAGGCA 2400
2401 TCAAATAAAA CGAAAGGCTC AGTCGAAAGA CTGGGCCTTT CGTTTATCT GTTGTTGTC 2460
2461 GGTGAACGCT CTCCTGAGTA GGACAAATCC GCCGGGAGCG GATTTGAACG TTGCGAAGCA 2520
2521 ACGGCCCGA GGGTGGCGGG CAGGACGCCC GCCATAAACT GCCAGGCATC AAATTAAGCA 2580
2581 GAAGGCCATC CTGACGGATG GCCTTTTTGC GCCATAAACT ACTCTTTTGT TTATTTTCT 2640
2641 AAATACATTC AAATATGTAT GTTTCTACAA GACAATAACC CTGATAAATG CTTCAATAAT 2700
2701 ATTGAAAAAG GAAGAGTATG CCGCTCATGA ATTTCCGTGT CGCCCTTATT CCCTTTTTTG 2760
2761 CGGCATTTTG CCTTCCTGTT TTTGCTCACC AGTATTCAAC CAGAAACGCT GGTGAAAGTA 2820
2821 AAGATCAGTT GGGTGCACGA GTGGGTTACA TCGAACTGGA TCTCAACAGC GGTAAGATCC 2880
```

FIG. 10B-3

```
2881 TTGAGAGTTT TCGCCCCGAA GAACGTTTTC CAATGATGAG CACTTTTAAA GTTCTGCTAT 2940
2941 GTGGCGCGGT ATTATCCCGT GTTGACGCCG GGCAAGAGCA ACTCGGTCGC CGCATACACT 3000
3001 ATTCTCAGAA TGACTTGGTT GAGTACTCAC CAGTCACAGA AAAGCATCTT ACGGATGGCA 3060
3061 TGACAGTAAG AGAATTATGC AGTGCTGCCA TAACCATGAG TGATAACACT GCGGCCAACT 3120
3121 TACTTCTGAC AACGATCGGA GGACCGAAGG AGCTAACCGC TTTTTTGCAC AACATGGGGG 3180
3181 ATCATGTAAC TCGCCTTGAT CGTTGGGAAC CGGAGCTGAA TGAAGCCATA CCAAACGACG 3240
3241 AGGTGACAC CACGATGCCT GTAGCAATGG CAACAACGTT GCGCAAACTA TTAACTGGCG 3300
3301 AACTACTTAC TCTAGCTTCC CGGCAACAAT TAATAGACTG GATGGAGGCG GATAAAGTTG 3360
3361 CAGAGAGCG TGGGTCTCGC GGTATCATTG CAGCACTGGG GCCAGATGGT AAGCCCTCCC 3420
3421 GTATCGTAGT TATCTACACG ACGGGGAGTC AGGCAACTAT GGATGAACGA AATAGACAGA 3480
3481 TCGCTGAGAT AGGTGCCTCA CTGATTAAGC ATTGGTAACT GTCAGACCAA GTTTACTCAT 3540
3541 ATATACTTTA GATTGATTTA AAACTTCATT TTTAATTTAA AAGGATCTAG GTGAAGATCC 3600
3601 TTTTTGATAA TCTCATGACC AAAATCCCTT AACGTGAGTT TTCGTTCCAC TGAGCGTCAG 3660
3661 ACCCCGTAGA AAAGATCAAA GGATCTTCTT GAGATCCTTT TTTTCTGCGC GTAATCTGCT 3720
3721 GCTTGCAAAC AAAAAAACCA CCGCTACCAG CGGTGGTTTG TTTGCCGGAT CAAGAGCTAC 3780
3781 CAACTCTTTT TCCGAAGGTA ACTGGCTTCA GCAGAGCGCA GATACCAAAT ACTGTCCTTC 3840
3841 TAGTGTAGCC GTAGTTAGGC CACCACTTCA AGAACTCTGT AGCACCGCCT ACATACCTCG 3900
3901 CTCTGCTAAT CCTGTTACCA GTGGCTGCTG CCAGTGGCGA TAAGTCGTGT CTTACCGGGT 3960
3961 TGGACTCAAG ACGATAGTTA CCGGATAAGG CGCAGCGGTC TAAGCTGAACG GGGGGTTCGT 4020
4021 GCACACAGCC CAGCTTGGAG CGAACGACCT ACACCGAACT GAGATACCTA CAGCGTGAGC 4080
```

FIG. 10B-4

```
4081 ATGAGAAAG CGCCACGCTT CCCGAAGGGA GAAAGGCCGA CAGGTATCCG GTAAGCGGCA 4140
4141 GGGTCGGAAC AGAGAGGCGC CTCTGACTTG TTCCAGGGGG AAACGCCTGG TATCTTTATA 4200
4201 GTCCTGTCGG GTTTCGCCAC CCTGACTTG AGCGTCGATT TTTGTGATGC TCGTCAGGGG 4260
4261 GGCGAGCCT ATGGAAAAAC GCCAGCAACG CGGCCTTTTT ACGGTTCCTG GCCTTTTGCT 4320
4321 GGCCTTTTGC TCACATGTTC TTTCCTGCGT TATCCCCTGA TTCTGTGGAT AACCGTATTA 4380
4381 CCGCCTTTGA GTGAGCTGAT ACCGCTCGCC GCAGCCGAAC GACCGAGCGC AGCGAGTCAG 4440
4441 TGAGCGAGGA AGCGGAAGAG CGCCTGATGC GGTATTTTCT CCTTACGCAT CTGTGCGGTA 4500
4501 TTTCACACCG CATATGGTGC ACTCTCAGTA CAATCTGCTC TGATGCCGCA TAGTTAAGCC 4560
4561 AGTATACACT CCGCTATCGC TACGTGACTG GGTCATGGCT GCGCCCCGAC ACCCGCCAAC 4620
4621 ACCCGTCTCC GGAGCTGCA TGTGTCAGAG GTTTTCACCG TCATCACGA AACGCGGGAG 4680
4681 GCAGCTGCGG TAAAGCTCAT CAGGCGTGTC GTGAAGGCAT GTCTGCTTC CTGCCTGTTC 4740
4741 ATCCGCGTCC AGCTCGTTGA GTTTCTCCAG AAGCGTTAAT GTCTGGCTTC TGATAAAGCG 4800
4801 GGCCATGTTA AGGGCGGTTT TTTCCTGTTT GGTCACTTGA TGCCTCCGTG TAAGGGGGAA 4860
4861 TTTCTGTTCA TGGGGGTAAT GATACCGATG AAACGAGAGA GGATGCTCAC GATACGGGTT 4920
4921 ACTGATGATG AACATGCCCG GTTACTGGAA CGTTGTGAGG GTAAACAACT GCGGTATGG 4980
4981 ATGCGGCGGG ACCAGAGAAA AATCACTCAG GGTCAATGCC AGCGCTTCGT TAATACAGAT 5040
5041 GTAGGTGTTC CACAGGGTAG CCAGCAGCAT CCTGCGATGC AGATCCGGAA CATAATGGTG 5100
5101 CAGGGCGCTG ACTTCCGCGT TTCCAGACTT TACGAAACAC GGAAACCGAA GACCATTCAT 5160
5161 GTTGTTGCTC AGGTCGCAGA CGTTTTGCAG CAGCAGTCGC TTCACGTTCG CTCGCGTATC 5220
5221 GGTGATTCAT TCTGCTAACC AGTAAGGCAA CCCCGCCAGC CTAGCCGGGT CCTCAACGAC 5280
5281 AGGAGCACGA TCATGCGCAC CCGTGGCCAC GACCCAACGC TGCCCGAGAT GCGCCGCGTG 5340
5341 CGGCTGCTGG AGATGGCGGA CGCGATGGAT ATGTTCTGCC AAGGGTTGGT TTGCGCATTC 5400
```

FIG. 10B-5

```
5401 ACAGTTCTCC GCAAGAATTG ATTGGCTCCA ATTCTTGGAG TGGTGAATCC GTTAGGGAGG 5460
5461 TGCCGCCGGC TTCCATTCAG GTCGAGGTGG CCCGGCTCCA TGCACCGCGA CGCAACGCGG 5520
5521 GGAGGCAGAC AAGGTATAGG GCGGGCCTA  CAATCCATGC CAACCCGTTC CATGTGCTCG 5580
5581 CCGAGGCGGC ATAAATCGCC GTGACGATCA GCGGTCCAGT GATCGAAGTT AGGCTGGTAA 5640
5641 GAGCCGCGAG CGATCCTTGA AGCTGTCCCT GATGGTCGTC ATCTACCTGC CTGGACAGCA 5700
5701 TGGCCTGCAA CGCGGCCATC CCGATGCCGC CGGAAGCGAG AAGAATCATA ATGGGGAAGG 5760
5761 CCATCCAGCC TCGCGTCGCG AACGCCAGCA AGACGTAGCC CAGGCGGTCG GCCGCCATGC 5820
5821 CGGCGATAAT GGCCTGCTTC TCGCCGAAAC GTTTGGTGGC GGGACCAGTG ACGAAGGCTT 5880
5881 GAGCGAAGCG GTCCTCGCCG AAAATGACCC AGAGCGTGC  CGGCACCTGT CCTACGAGTT 5940
5941 GCATGATAAA GAAGACAGTC ATAAGTGCGG CGACGATAGT CATGCCCCGC GCCACCCGA  6000
6001 AGGAGCTGAC TGGGTTGAAG GCTCTCAAGG GCATCGGTCG ACGCTCTCCC TTATGCGACT 6060
6061 CCTGCATTAG GAAGCAGCCT AGTAGTAGGT TGAGGCCGTT GAGCACCGC  GCCGCAAGGA 6120
6121 ATGGTGCATG CAAGGAGATG GCGCCAACA  GTCCCCCGGC CACGGGGCCT GCCACCATAC 6180
6181 CCACGCCGAA ACAAGCGCTC ATGAGCCCGA AGTGGCGAGC CCGATCTTCC CCATCGGTGA 6240
6241 TGTCGGCGAT ATAGGCGCCA GCAACCGCAC CTGTGCCGGC GGTGATGCCG GCCACGATGC 6300
6301 GTCCGGCGTA GAGGATCCGG AGCTTATCGA CTGCACGGTG CACCAATGCT TCTGGCGTCA 6360
6361 GGCAGCCATC GGAAGCTGTG GTATGCGTGT CTGCACGGTG AATCACTGCA TAATTCGTGT 6420
6421 CGCTCAAGGC GCACTCCCGT TCTGGATAAT GTTTTTTGCG CCGACATCAT AACGGTTCTG 6480
6481 GCAAATATTC TGAAATGAGC TGTTGACAAT GTTTTTTGCG TAATCATCGG CTCGTATAAT GTGTGGAATT 6540
6541 GTGAGCGGAT AACAATTTCA CACAGGAAAC A                                6571
           |         |         |         |         |         |
           10        20        30        40        50        60
```

FIG. 11A

DNA sequence    1323 b.p.    TGCCTCGCAGAG ... GTGCACAACTGT    linear

```
1/1                                              31/11
TGC CTC GCA GAG GGC ACT CGG ATC TTC GAT CCG GTC ACC GGT ACA ACG CAT CGC ATC GAG
 C   L   A   E   G   T   R   I   F   D   P   V   T   G   T   T   H   R   I   E
61/21                                            91/31
GAT GTT GTC GAT GGG CGC AAG CCT ATT CAT GTC GTG GCT GCT GCC AAG GAC GGA ACG CTG
 D   V   V   D   G   R   K   P   I   H   V   V   A   A   A   K   D   G   T   L
121/41                                           151/51
CAT GCG CGG CCC CTG GTG TCC TGG TTC GAC CAG GGA ACG CGG GAT CAC AAG GTG CTG CGG
 H   A   R   P   L   V   S   W   F   D   Q   G   T   R   D   H   K   V   L   R
181/61                                           211/71
ATC GCC GGT GGC GCC ATC GTG TGG GCG ACA CCC GAT CAC AAG GTG GCG CAA CCG CGA TTC GAT
 I   A   G   G   A   I   V   W   A   T   P   D   H   K   V   A   Q   P   R   F   D
241/81                                           271/91
TGG CGT GCC GCC GGG GAA CTC CGC AAG GGA GAC AGG GTG GCG CGG CTG CTT GGC TAC CTG ATC
 W   R   A   A   G   E   L   R   K   G   D   R   V   A   R   L   L   G   Y   L   I
301/101                                          331/111
GGA TTC GGT GAC AGT GCG CCG ATT CCG GCG GAT CAT GCC CGG CTG CTT GGC TAC CTG ATC
 G   F   G   D   S   A   P   I   P   A   D   H   A   R   L   L   G   Y   L   I
```

FIG. 1/B

```
361/121
GGA GAT GGC AGG GAT GGT TGG GTG GGG GGC AAG ACT CCG ATC AAC TTC ATC AAT GTT CAG
 G   D   G   R   D   G   W   V   G   G   K   T   P   I   N   F   I   N   V   Q
                                         391/131
421/141
CGG GCG CTC ATT GAC GAC GTG ACG CGA ATC GCT GCG ACG CTC GGT TGC GCG GCC CAT CCG
 R   A   L   I   D   D   V   T   R   I   A   A   T   L   G   C   A   A   H   P
                             451/151
481/161
CAG GGG CGT ATC TCA CTC GCG ATC GCT CAT CGA CCC GGT GAG CGC AAC GGT GTG GCA GAC
 Q   G   R   I   S   L   A   I   A   H   R   P   G   E   R   N   G   V   A   D
                                 511/171
541/181
CTT TGT CAG CAG GCC GGT ATC TAC GGC AAG CTC GCG TGG GAG AAG ACG ATT CCG AAT TGG
 L   C   Q   Q   A   G   I   Y   G   K   L   A   W   E   K   T   I   P   N   W
                                     571/191                   631/211
601/201
TTC TTC GAG CCG GAC ATC GCC GAC ATT GTC GGC AAT CTG CTC CGG TTC GGT CTG TTC GAA
 F   F   E   P   D   I   A   D   I   V   G   N   L   L   R   F   G   L   F   E   1
                                         691/231
661/221
AGC GAC GGG TGG GTG AGC CGG GAA CAG ACC GGG GCA CTT CGG CTG CGG TTC GGT ACG ACG
 S   D   G   W   V   S   R   E   Q   T   G   A   L   R   L   R   F   G   T   T
                                             751/251
721/241
TCT GAA CAA CTC GCG CAT CAG ATT CAT TGG CTG CTG CTG CTC CGG TTC GGT GTC GGG AGC
 S   E   Q   L   A   H   Q   I   H   W   L   L   L   L   R   F   G   V   G   S
                                             811/271
781/261
GTT CGA GAT TAC GAT CCG ACC CAG AAG CGG CCC AGC ATC GTC AAC GGT CGA CGG ATC CAG
 V   R   D   Y   D   P   T   Q   K   R   P   S   I   V   N   G   R   R   I   Q
```

FIG. 11C

```
841/281
AGC AAA CGT CAA GTG TTC GAG GTC CGG ATC TCG GGT ATG GAT AAC GTC ACG GCA TTC GCG
 S   K   R   Q   V   F   E   V   R   I   S   G   M   D   N   V   T   A   F   A
                                          871/291
901/301
GAG TCA GTT CCC ATG TGG GGG CCG CGC GGT ATC CAG GCG CTT ATC CAG GCG ATT CCA GAA GCC
 E   S   V   P   M   W   G   P   R   G   I   Q   A   L   I   Q   A   I   P   E   A
                                                  931/311
961/321
ACG CAG GGG CGG CGT GGA TCG CAA GCG ACA TAT CTG GCT GCA GAG ATG ACC GAT GCC
 T   Q   G   R   R   G   S   Q   A   T   Y   L   A   A   E   M   T   D   A
                              991/331                     1051/351
1021/341
GTG CTG AAT TAT CTG GAC CCC CGC GGT GGA ATG AAG CAG GTC TTA GGT GCC AGC CGC ATG ATC GGT
 V   L   N   Y   L   D   P   R   G   G   M   K   Q   V   L   G   A   S   R   M   I   G
                          1111/371
1081/361
GTA GCT TCC GGG GAC CCC CGC GGT GGA ATG AAG CAG GTC TTA GGT GCC AGC CGC CTT CGT
 V   A   S   G   D   P   R   G   G   M   K   Q   V   L   G   A   S   R   L   R
                                      1171/391
1141/381
CGG GAT CGC GTG CAG GCG CTC GCG GAT GAC AAA TTC CTG CAC GAC ATG CTG
 R   D   R   V   Q   A   L   A   D   D   K   F   L   H   D   M   L
              1231/411
1201/401
GCG GAA GAA CTC CGC TAT TCC GTG ATC CGA GAA GTG CTG CCA ACG CGG GCA CGA ACG
 A   E   E   L   R   Y   S   V   I   R   E   V   L   P   T   R   A   R   T
                                                                1291/431
1261/421
TTC GAC CTC GAG GTC GAG GAA CTG CAC ACC CTC GTC GCC GAA GGG GTT GTC CAC AAC
 F   D   L   E   V   E   E   L   H   T   L   V   A   E   G   V   V   H   N
1321/441
TGT
 C
```

MUTATION 1 E220K GAA → AAA
MUTATION 2 H41R CAT → CGT

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: amino acid ( x i ) SEQUENCE DESCRIPTION: SEQ ID NO:1:

Lys Val Val Lys Asn Lys Cys Leu Ala Glu Gly Thr
    1               5                   10

( 2 ) INFORMATION FOR SEQ ID NO:2:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( i i ) MOLECULE TYPE: amino acid ( x i ) SEQUENCE DESCRIPTION: SEQ ID NO:2:

Glu Gly Val Val Val His Asn Cys Ser Pro Pro Phe Lys
    1               5                   10

( 2 ) INFORMATION FOR SEQ ID NO:3:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: amino acid ( x i ) SEQUENCE DESCRIPTION: SEQ ID NO:3:

Arg Glu Pro Lys Glu Leu Cys Leu Ala Glu Gly Thr
    1               5                   10

( 2 ) INFORMATION FOR SEQ ID NO:4:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: amino acid ( x i ) SEQUENCE DESCRIPTION: SEQ ID NO:4:

```
Glu Gly Val Val Val His Asn Cys Glu Leu Val Ile Ser
 1               5                   10
```

( 2 ) INFORMATION FOR SEQ ID NO:5:

( i ) SEQUENCE CHARACTERISTICS:
        ( A ) LENGTH: 861 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
ATGAAACAAT ACCAAGATTT AATTAAAGAC ATTTTTGAAA ATGGTTATGA AACCGATGAT      60
CGTACAGGCA CAGGAACAAT TGCTCTGTTC GGATCTAAAT TACGCTGGGA TTTAACTAAA     120
GGTTTTCCTG CGGTAACAAC TAAGAAGCTC GCCTGGAAAG CTTGCATTGC TGAGCTAATA     180
TGGTTTTTAT CAGGAAGCAC AAATGTCAAT GATTTACGAT TAATTCAACA CGATTCGTTA     240
ATCCAAGGCA AAACAGTCTG GGATGAAAAT TACGAAAATC AAGCAAAGA TTTAGGATAC      300
CATAGCGGTG AACTTGGTCC AATTTATGGA AACAGTGGC GTGATTTTGG TGGTGTAGAC      360
CAAATTATAG AAGTTATTGA TCGTATTAAA AAACTGCCAA ATGATAGGCG TCAAATTGTT     420
TCTGCATGGA ATCCAGCTGA ACTTAAATAT ATGGCATTAC CGCCTTGTCA TATGTTCTAT     480
CAGTTTAATG TGCGTAATGG CTATTTGGAT TTGCAGTGGT ATCAACGCTC AGTAGATGTT     540
TTCTTGGGTC TACCGTTTAA TATTGCGTCA TATGCTACGT TAGTTCATAT TGTAGCTAAG     600
ATGTGTAATC TTATTCCAGG GGATTTGATA TTTTCTGGTG GTAATACTCA TATCTATATG     660
AATCACGTAG AACAATGTAA AGAAATTTTG AGGCGTGAAC CTAAAGAGCT TTGTGAGCTG     720
GTAATAAGTG GTCTACCTTA TAAATTCCGA TATCTTTCTA CTAAAGAACA ATTAAAATAT     780
GTTCTTAAAC TTAGGCCTAA AGATTTCGTT CTTAACAACT ATGTATCACA CCCTCCTATT     840
AAAGGAAAGA TGGCGGTGTA A                                               861
```

( 2 ) INFORMATION FOR SEQ ID NO:6:

( i ) SEQUENCE CHARACTERISTICS:
        ( A ) LENGTH: 3253 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
GCTCCTAATT ACTTATTTAC TTATTTTTTC GTAGGACTAT CACCTAACTA ACGGGGGCGA      60
ATTCGAGCTC GGTACCCGGG GATCCTCTAG AGTCGACCTG CAGGCATGCA AGCTTGAGTA     120
TTCTATAGTG TCACCTAAAT AGCTTGGCGT AATCATGGTC ATAGCTGTTT CCTGTGTGAA     180
ATTGTTATCC GCTCACAATT CCACACAACA TACGAGCCGG AAGCATAAAG TGTAAAGCCT     240
```

-continued

| | | | | | |
|---|---|---|---|---|---|
|GGGGTGCCTA|ATGAGTGAGC|TAACTCACAT|TAATTGCGTT|GCGCTCACTG|CCCGCTTTCC| 300
|AGTCGGGAAA|CCTGTCGTGC|CAGCTGCATT|AATGAATCGG|CCAACGCGCG|GGGAGAGGCG| 360
|GTTTGCGTAT|TGGGCGCTCT|TCCGCTTCCT|CGCTCACTGA|CTCGCTGCGC|TCGGTCGTTC| 420
|GGCTGCGGCG|AGCGGTATCA|GCTCACTCAA|AGGCGGTAAT|ACGGTTATCC|ACAGAATCAG| 480
|GGATAACGC|AGGAAAGAAC|ATGTGAGCAA|AAGGCCAGCA|AAAGGCCAGG|AACCGTAAAA| 540
|AGGCCGCGTT|GCTGGCGTTT|TTCCATAGGC|TCCGCCCCC|TGACGAGCAT|CACAAAAATC| 600
|GACGCTCAAG|TCAGAGGTGG|CGAAACCCGA|CAGGACTATA|AAGATACCAG|GCGTTTCCCC| 660
|CTGGAAGCTC|CCTCGTGCGC|TCTCCTGTTC|CGACCCTGCC|GCTTACCGGA|TACCTGTCCG| 720
|CCTTTCTCCC|TTCGGGAAGC|GTGGCGCTTT|CTCATAGCTC|ACGCTGTAGG|TATCTCAGTT| 780
|CGGTGTAGGT|CGTTCGCTCC|AAGCTGGGCT|GTGTGCACGA|ACCCCCCGTT|CAGCCCGACC| 840
|GCTGCGCCTT|ATCCGGTAAC|TATCGTCTTG|AGTCCAACCC|GGTAAGACAC|GACTTATCGC| 900
|CACTGGCAGC|AGCCACTGGT|AACAGGATTA|GCAGAGCGAG|GTATGTAGGC|GGTGCTACAG| 960
|AGTTCTTGAA|GTGGTGGCCT|AACTACGGCT|ACACTAGAAG|GACAGTATTT|GGTATCTGCG| 1020
|CTCTGCTGAA|GCCAGTTACC|TTCGGAAAAA|GAGTTGGTAG|CTCTTGATCC|GGCAAACAAA| 1080
|CCACCGCTGG|TAGCGGTGGT|TTTTTTGTTT|GCAAGCAGCA|GATTACGCGC|AGAAAAAAAG| 1140
|GATCTCAAGA|AGATCCTTTG|ATCTTTTCTA|CGGGGTCTGA|CGCTCAGTGG|AACGAAAACT| 1200
|CACGTTAAGG|GATTTTGGTC|ATGAGATTAT|CAAAAAGGAT|CTTCACCTAG|ATCCTTTTAA| 1260
|ATTAAAAATG|AAGTTTTAAA|TCAATCTAAA|GTATATATGA|GTAAACTTGG|TCTGACAGTT| 1320
|ACCAATGCTT|AATCAGTGAG|GCACCTATCT|CAGCGATCTG|TCTATTTCGT|TCATCCATAG| 1380
|TTGCCTGACT|CCCCGTCGTG|TAGATAACTA|CGATACGGGA|GGGCTTACCA|TCTGGCCCCA| 1440
|GTGCTGCAAT|GATACCGCGA|GACCCACGCT|CACCGGCTCC|AGATTTATCA|GCAATAAACC| 1500
|AGCCAGCCGG|AAGGGCCGAG|CGCAGAAGTG|GTCCTGCAAC|TTTATCCGCC|TCCATCCAGT| 1560
|CTATTAATTG|TTGCCGGGAA|GCTAGAGTAA|GTAGTTCGCC|AGTTAATAGT|TTGCGCAACG| 1620
|TTGTTGCCAT|TGCTACAGGC|ATCGTGGTGT|CACGCTCGTC|GTTTGGTATG|GCTTCATTCA| 1680
|GCTCCGGTTC|CCAACGATCA|AGGCGAGTTA|CATGATCCCC|CATGTTGTGC|AAAAAAGCGG| 1740
|TTAGCTCCTT|CGGTCCTCCG|ATCGTTGTCA|GAAGTAAGTT|GGCCGCAGTG|TTATCACTCA| 1800
|TGGTTATGGC|AGCACTGCAT|AATTCTCTTA|CTGTCATGCC|ATCCGTAAGA|TGCTTTTCTG| 1860
|TGACTGGTGA|GTACTCAACC|AAGTCATTCT|GAGAATAGTG|TATGCGGCGA|CCGAGTTGCT| 1920
|CTTGCCCGGC|GTCAATACGG|GATAATACCG|CGCCACATAG|CAGAACTTTA|AAAGTGCTCA| 1980
|TCATTGGAAA|ACGTTCTTCG|GGGCGAAAAC|TCTCAAGGAT|CTTACCGCTG|TTGAGATCCA| 2040
|GTTCGATGTA|ACCCACTCGT|GCACCCAACT|GATCTTCAGC|ATCTTTTACT|TTCACCAGCG| 2100
|TTTCTGGGTG|AGCAAAAACA|GGAAGGCAAA|ATGCCGCAAA|AAAGGGAATA|AGGGCGACAC| 2160
|GGAAATGTTG|AATACTCATA|CTCTTCCTTT|TTCAATATTA|TTGAAGCATT|TATCAGGGTT| 2220
|ATTGTCTCAT|GAGCGGATAC|ATATTTGAAT|GTATTTAGAA|AAATAAACAA|ATAGGGGTTC| 2280
|CGCGCACATT|TCCCCGAAAA|GTGCCACCTG|ACGTCTAAGA|AACCATTATT|ATCATGACAT| 2340
|TAACCTATAA|AAATAGGCGT|ATCACGAGGC|CCTTTCGTCT|CGCGCGTTTC|GGTGATGACG| 2400
|GTGAAAACCT|CTGACACATG|CAGCTCCCGG|AGACGGTCAC|AGCTTGTCTG|TAAGCGGATG| 2460
|CCGGGAGCAG|ACAAGCCCGT|CAGGGCGCGT|CAGCGGGTGT|TGGCGGGTGT|CGGGGCTGGC| 2520
|TTAACTATGC|GGCATCAGAG|CAGATTGTAC|TGAGAGTGCA|CCATATGCGG|TGTGAAATAC| 2580
|CGCACAGATG|CGTAAGGAGA|AAATACCGCA|TCAGGCGACG|CGCCCTGTAG|CGGCGCATTA| 2640

| | | | | | |
|---|---|---|---|---|---|
|AGCGCGGCGG|GTGTGGTGGT|TACGCGCAGC|GTGACCGCTA|CACTTGCCAG|CGCCCTAGCG|2700
|CCCGCTCCTT|TCGCTTTCTT|CCCTTCCTTT|CTCGCCACGT|TCGCCGGCTT|TCCCCGTCAA|2760
|GCTCTAAATC|GGGGGCTCCC|TTTAGGGTTC|CGATTTAGAG|CTTTACGGCA|CCTCGACCGC|2820
|AAAAAACTTG|ATTTGGGTGA|TGGTTCACGT|AGTGGGCCAT|CGCCCTGATA|GACGGTTTTT|2880
|CGCCCTTTGA|CGTTGGAGTC|CACGTTCTTT|AATAGTGGAC|TCTTGTTCCA|AACTGGAACA|2940
|ACACTCAACC|CTATCTCGGT|CTATTCTTTT|GATTTATAAG|GGATTTTGCC|GATTTCGGCC|3000
|TATTGGTTAA|AAAATGAGCT|GATTAACAA|ATATTAACG|CGAATTTTAA|CAAAATATTA|3060
|ACGTTTACAA|TTTCCATTCG|CCATTCAGGC|TGCGCAACTG|TTGGGAAGGG|CGATCGGTGC|3120
|GGGCCTCTTC|GCTATTACGC|CAGCTGGCGA|AAGGGGGATG|TGCTGCAAGG|CGATTAAGTT|3180
|GGGTAACGCC|AGGGTTTTCC|CAGTCACGAC|GTTGTAAAAC|GACGGCCAGT|GAATTGTAAT|3240
|ACGACTCACT|ATA| | | | |3253

( 2 ) INFORMATION FOR SEQ ID NO:7:

( i ) SEQUENCE CHARACTERISTICS:
        ( A ) LENGTH: 4586 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

| | | | | | |
|---|---|---|---|---|---|
|TTCTGTTTCC|TGTGTGAAAT|TGTTATCCGC|TCACAATTCC|ACACATTATA|CGAGCCGATG|60
|ATTAATTGTC|AACAGCTCAT|TTCAGAATAT|TTGCCAGAAC|CGTTATGATG|TCGGCGCAAA|120
|AAACATTATC|CAGAACGGGA|GTGCGCCTTG|AGCGACACGA|ATTATGCAGT|GATTACGAC|180
|CTGCACAGCC|ATACCACAGC|TTCCGATGGC|TGCCTGACGC|CAGAAGCATT|GGTGCACCGT|240
|GCAGTCGATA|AGCTCCGGAT|CCTCTACGCC|GGACGCATCG|TGGCCGGCAT|CACCGGCGCC|300
|ACAGGTGCGG|TTGCTGGCGC|CTATATCGCC|GACATCACCG|ATGGGGAAGA|TCGGGCTCGC|360
|CACTTCGGGC|TCATGAGCGC|TTGTTTCGGC|GTGGGTATGG|TGGCAGGCCC|CGTGGCCGGG|420
|GGACTGTTGG|GCGCCATCTC|CTTGCATGCA|CCATTCCTTG|CGGCGGCGGT|GCTCAACGGC|480
|CTCAACCTAC|TACTGGGCTG|CTTCCTAATG|CAGGAGTCGC|ATAAGGGAGA|GCGTCGACCG|540
|ATGCCCTTGA|GAGCCTTCAA|CCCAGTCAGC|TCCTTCCGGT|GGGCGCGGGG|CATGACTATC|600
|GTCGCCGCAC|TTATGACTGT|CTTCTTTATC|ATGCAACTCG|TAGGACAGGT|GCCGGCAGCG|660
|CTCTGGGTCA|TTTTCGGCGA|GGACCGCTTT|CGCTGGAGCG|CGACGATGAT|CGGCCTGTCG|720
|CTTGCGGTAT|TCGGAATCTT|GCACGCCCTC|GCTCAAGCCT|TCGTCACTGG|TCCCGCCACC|780
|AAACGTTTCG|GCGAGAAGCA|GGCCATTATC|GCCGGCATGG|CGGCCGACGC|GCTGGGCTAC|840
|GTCTTGCTGG|CGTTCGCGAC|GCGAGGCTGG|ATGGCCTTCC|CCATTATGAT|TCTTCTCGCT|900
|TCCGGCGGCA|TCGGGATGCC|CGCGTTGCAG|GCCATGCTGT|CCAGGCAGGT|AGATGACGAC|960
|CATCAGGGAC|AGCTTCAAGG|ATCGCTCGCG|GCTCTTACCA|GCCTAACTTC|GATCACTGGA|1020
|CCGCTGATCG|TCACGGCGAT|TTATGCCGCC|TCGGCGAGCA|CATGGAACGG|GTTGGCATGG|1080
|ATTGTAGGCG|CCGCCCTATA|CCTTGTCTGC|CTCCCCGCGT|GCGTCGCGG|TGCATGGAGC|1140
|CGGGCCACCT|CGACCTGAAT|GGAAGCCGGC|GGCACCTCGC|TAACGGATTC|ACCACTCCAA|1200
|GAATTGGAGC|CAATCAATTC|TTGCGGAGAA|CTGTGAATGC|GCAAACCAAC|CCTTGGCAGA|1260
|ACATATCCAT|CGCGTCCGCC|ATCTCCAGCA|GCCGCACGCG|GCGCATCTCG|GGCAGCGTTG|1320

-continued

```
GGTCCTGGCC ACGGGTGCGC ATGATCGTGC TCCTGTCGTT GAGGACCCGG CTAGGCTGGC   1380
GGGGTTGCCT TACTGGTTAG CAGAATGAAT CACCGATACG CGAGCGAACG TGAAGCGACT   1440
GCTGCTGCAA AACGTCTGCG ACCTGAGCAA CAACATGAAT GGTCTTCGGT TTCCGTGTTT   1500
CGTAAAGTCT GGAAACGCGG AAGTCAGCGC CTGCACCAT TATGTTCCGG ATCTGCATCG    1560
CAGGATGCTG CTGGCTACCC TGTGGAACAC CTACATCTGT ATTAACGAAG CGCTGGCATT   1620
GACCCTGAGT GATTTTCTC TGGTCCCGCC GCATCCATAC CGCCAGTTGT TTACCCTCAC    1680
AACGTTCCAG TAACCGGGCA TGTTCATCAT CAGTAACCCG TATCGTGAGC ATCCTCTCTC   1740
GTTTCATCGG TATCATTACC CCCATGAACA GAAATTCCCC CTTACACGGA GGCATCAAGT   1800
GACCAAACAG GAAAAAACCG CCCTTAACAT GGCCCGCTTT ATCAGAAGCC AGACATTAAC   1860
GCTTCTGGAG AAACTCAACG AGCTGGACGC GGATGAACAG GCAGACATCT GTGAATCGCT   1920
TCACGACCAC GCTGATGAGC TTTACCGCAG CTGCCTCGCG CGTTTCGGTG ATGACGGTGA   1980
AAACCTCTGA CACATGCAGC TCCCGGAGAC GGTCACAGCT TGTCTGTAAG CGGATGCCGG   2040
GAGCAGACAA GCCCGTCAGG GCGCGTCAGC GGGTGTTGGC GGGTGTCGGG GCGCAGCCAT   2100
GACCCAGTCA CGTAGCGATA GCGGAGTGTA TACTGGCTTA ACTATGCGGC ATCAGAGCAG   2160
ATTGTACTGA GAGTGCACCA TATGCGGTGT GAAATACCGC ACAGATGCGT AAGGAGAAAA   2220
TACCGCATCA GGCGCTCTTC CGCTTCCTCG CTCACTGACT CGCTGCGCTC GGTCGTTCGG   2280
CTGCGGCGAG CGGTATCAGC TCACTCAAAG GCGGTAATAC GGTTATCCAC AGAATCAGGG   2340
GATAACGCAG GAAAGAACAT GTGAGCAAAA GGCCAGCAAA AGGCCAGGAA CCGTAAAAAG   2400
GCCGCGTTGC TGGCGTTTTT CCATAGGCTC CGCCCCCTG ACGAGCATCA CAAAAATCGA    2460
CGCTCAAGTC AGAGGTGGCG AAACCCGACA GGACTATAAA GATACCAGGC GTTTCCCCCT   2520
GGAAGCTCCC TCGTGCGCTC TCCTGTTCCG ACCCTGCCGC TTACCGGATA CCTGTCCGCC   2580
TTTCTCCCTT CGGGAAGCGT GGCGCTTTCT CATAGCTCAC GCTGTAGGTA TCTCAGTTCG   2640
GTGTAGGTCG TTCGCTCCAA GCTGGGCTGT GTGCACGAAC CCCCCGTTCA GCCCGACCGC   2700
TGCGCCTTAT CCGGTAACTA TCGTCTTGAG TCCAACCCGG TAAGACACGA CTTATCGCCA   2760
CTGGCAGCAG CCACTGGTAA CAGGATTAGC AGAGCGAGGT ATGTAGGCGG TGCTACAGAG   2820
TTCTTGAAGT GGTGGCCTAA CTACGGCTAC ACTAGAAGGA CAGTATTTGG TATCTGCGCT   2880
CTGCTGAAGC CAGTTACCTT CGGAAAAGA GTTGGTAGCT CTTGATCCGG CAAACAAACC    2940
ACCGCTGGTA GCGGTGGTTT TTTTGTTTGC AAGCAGCAGA TTACGCGCAG AAAAAAAGGA   3000
TCTCAAGAAG ATCCTTTGAT CTTTTCTACG GGGTCTGACG CTCAGTGGAA CGAAAACTCA   3060
CGTTAAGGGA TTTTGGTCAT GAGATTATCA AAAAGGATCT TCACCTAGAT CCTTTTAAAT   3120
TAAAAATGAA GTTTTAAATC AATCTAAAGT ATATATGAGT AAACTTGGTC TGACAGTTAC   3180
CAATGCTTAA TCAGTGAGGC ACCTATCTCA GCGATCTGTC TATTTCGTTC ATCCATAGTT   3240
GCCTGACTCC CCGTCGTGTA GATAACTACG ATACGGGAGG GCTTACCATC TGGCCCCAGT   3300
GCTGCAATGA TACCGCGAGA CCCACGCTCA CCGGCTCCAG ATTTATCAGC AATAAACCAG   3360
CCAGCCGGAA GGGCCGAGCG CAGAAGTGGT CCTGCAACTT TATCCGCCTC CATCCAGTCT   3420
ATTAATTGTT GCCGGGAAGC TAGAGTAAGT AGTTCGCCAG TTAATAGTTT GCGCAACGTT   3480
GTTGCCATTG CTACAGGCAT CGTGGTGTCA CGCTCGTCGT TTGGTATGGC TTCATTCAGC   3540
TCCGGTTCCC AACGATCAAG GCGAGTTACA TGATCCCCCA TGTTGTGCAA AAAAGCGGTT   3600
AGCTCCTTCG GTCCTCCGAT CGTTGTCAGA AGTAAGTTGG CCGCAGTGTT ATCACTCATG   3660
GTTATGGCAG CACTGCATAA TTCTCTTACT GTCATGCCAT CCGTAAGATG CTTTTCTGTG   3720
```

| | | | | | |
|---|---|---|---|---|---|
| ACTGGTGAGT | ACTCAACCAA | GTCATTCTGA | GAATAGTGTA | TGCGGCGACC | GAGTTGCTCT | 3780 |
| TGCCCGGCGT | CAACACGGGA | TAATACCGCG | CCACATAGCA | GAACTTTAAA | AGTGCTCATC | 3840 |
| ATTGGAAAAC | GTTCTTCGGG | GCGAAAACTC | TCAAGGATCT | TACCGCTGTT | GAGATCCAGT | 3900 |
| TCGATGTAAC | CCACTCGTGC | ACCCAACTGA | TCTTCAGCAT | CTTTTACTTT | CACCAGCGTT | 3960 |
| TCTGGGTGAG | CAAAAACAGG | AAGGCAAAAT | GCCGCAAAAA | AGGGAATAAG | GGCGACACGG | 4020 |
| AAATGTTGAA | TACTCATACT | CTTCCTTTTT | CAATATTATT | GAAGCATTTA | TCAGGGTTAT | 4080 |
| TGTCTCATGA | GCGGATACAT | ATTTGAATGT | ATTTAGAAAA | ATAAACAAAA | GAGTTTGTAG | 4140 |
| AAACGCAAAA | AGGCCATCCG | TCAGGATGGC | CTTCTGCTTA | ATTTGATGCC | TGGCAGTTTA | 4200 |
| TGGCGGGCGT | CCTGCCCGCC | ACCCTCCGGG | CCGTTGCTTC | GCAACGTTCA | AATCCGCTCC | 4260 |
| CGGCGGATTT | GTCCTACTCA | GGAGAGCGTT | CACCGACAAA | CAACAGATAA | AACGAAAGGC | 4320 |
| CCAGTCTTTC | GACTGAGCCT | TTCGTTTTAT | TTGATGCCTG | GCAGTTCCCT | ACTCTCGCAT | 4380 |
| GGGGAGACCC | CACACTACCA | TCGGCGCTAC | GGCGTTTCAC | TTCTGAGTTC | GGCATGGGGT | 4440 |
| CAGGTGGGAC | CACCGCGCTA | CTGCCGCCAG | GCAAATTCTG | TTTTATCAGA | CCGCTTCTGC | 4500 |
| GTTCTGATTT | AATCTGTATC | AGGCTGAAAA | TCTTCTCTCA | TCCGCCAAAA | CAGAAGCTTG | 4560 |
| GCTGCAGGTC | GACGGATCCC | CGGGAA | | | | 4586 |

( 2 ) INFORMATION FOR SEQ ID NO:8:

( i ) SEQUENCE CHARACTERISTICS:
        ( A ) LENGTH: 5251 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

| | | | | | |
|---|---|---|---|---|---|
| GAATTCATGA | AACAATACCA | AGATTTAATT | AAAGACATTT | TTGAAAATGG | TTATGAAACC | 60 |
| GATGATCGTA | CAGGCACAGG | AACAATTGCT | CTGTTCGGAT | CTAAATTACG | CTGGGATTTA | 120 |
| ACTAAAGGTT | TTCCTGCGGT | AACAACTAAG | AAGCTCGCCT | GGAAAGCTTG | CATTGCTGAG | 180 |
| CTAATATGGT | TTTTATCAGG | AAGCACAAAT | GTCAATGATT | TACGATTAAT | TCAACACGAT | 240 |
| TCGTTAATCC | AAGGCAAAAC | AGTCTGGGAT | GAAAATTACG | AAAATCAAGC | AAAAGATTTA | 300 |
| GGATACCATA | GCGGTGAACT | TGGTCCAATT | TATGGAAAAC | AGTGGCGTGA | TTTTGGTGGT | 360 |
| GTAGACCAAA | TTATAGAAGT | TATTGATCGT | ATTAAAAAAC | TGCCAAATGA | TAGGCGTCAA | 420 |
| ATTGTTTCTG | CATGGAATCC | AGCTGAACTT | AAATATATGG | CATTACCGCC | TTGTCATATG | 480 |
| TTCTATCAGT | TTAATGTGCG | TAATGGCTAT | TTGGATTTGC | AGTGGTATCA | ACGCTCAGTA | 540 |
| GATGTTTTCT | TGGGTCTACC | GTTTAATATT | GCGTCATATG | CTACGTTAGT | TCATATTGTA | 600 |
| GCTAAGATGT | GTAATCTTAT | TCCAGGGGAT | TTGATATTTT | CTGGTGGTAA | TACTCATATC | 660 |
| TATATGAATC | ACGTAGAACA | ATGTAAAGAA | ATTTTGAGGC | GTGAACCTAA | AGAGCTCTGT | 720 |
| GAACTAGTAA | TAAGTGGTCT | ACCTTATAAA | TTCCGATATC | TTTCTACTAA | AGAACAATTA | 780 |
| AAATATGTTC | TTAAACTTAG | GCCTAAAGAT | TTCGTTCTTA | CAACTATGT | ATCACACCCT | 840 |
| CCTATTAAAG | GAAAGATGGC | GGTGTAACTG | CAGCCAAGCT | TCTGTTTTGG | CGGATGAGAG | 900 |
| AAGATTTTCA | GCCTGATACA | GATTAAATCA | GAACGCAGAA | GCGGTCTGAT | AAAACAGAAT | 960 |
| TTGCCTGGCG | GCAGTAGCGC | GGTGGTCCCA | CCTGACCCCA | TGCCGAACTC | AGAAGTGAAA | 1020 |
| CGCCGTAGCG | CCGATGGTAG | TGTGGGGTCT | CCCCATGCGA | GAGTAGGGAA | CTGCCAGGCA | 1080 |
| TCAAATAAAA | CGAAAGGCTC | AGTCGAAAGA | CTGGGCCTTT | CGTTTTATCT | GTTGTTTGTC | 1140 |

```
GGTGAACGCT CTCCTGAGTA GGACAAATCC GCCGGGAGCG GATTTGAACG TTGCGAAGCA      1200
ACGGCCCGGA GGGTGGCGGG CAGGACGCCC GCCATAAACT GCCAGGCATC AAATTAAGCA      1260
GAAGGCCATC CTGACGGATG GCCTTTTTGC GTTTCTACAA ACTCTTTTGT TTATTTTTCT      1320
AAATACATTC AAATATGTAT CCGCTCATGA GACAATAACC CTGATAAATG CTTCAATAAT      1380
ATTGAAAAAG GAAGAGTATG AGTATTCAAC ATTTCCGTGT CGCCCTTATT CCCTTTTTTG      1440
CGGCATTTTG CCTTCCTGTT TTTGCTCACC CAGAAACGCT GGTGAAAGTA AAAGATGCTG      1500
AAGATCAGTT GGGTGCACGA GTGGGTTACA TCGAACTGGA TCTCAACAGC GGTAAGATCC      1560
TTGAGAGTTT TCGCCCCGAA GAACGTTTTC CAATGATGAG CACTTTTAAA GTTCTGCTAT      1620
GTGGCGCGGT ATTATCCCGT GTTGACGCCG GGCAAGAGCA ACTCGGTCGC CGCATACACT      1680
ATTCTCAGAA TGACTTGGTT GAGTACTCAC CAGTCACAGA AAAGCATCTT ACGGATGGCA      1740
TGACAGTAAG AGAATTATGC AGTGCTGCCA TAACCATGAG TGATAACACT GCGGCCAACT      1800
TACTTCTGAC AACGATCGGA GGACCGAAGG AGCTAACCGC TTTTTTGCAC AACATGGGGG      1860
ATCATGTAAC TCGCCTTGAT CGTTGGGAAC CGGAGCTGAA TGAAGCCATA CCAAACGACG      1920
AGCGTGACAC CACGATGCCT GTAGCAATGG CAACAACGTT GCGCAAACTA TTAACTGGCG      1980
AACTACTTAC TCTAGCTTCC CGGCAACAAT TAATAGACTG GATGGAGGCG GATAAAGTTG      2040
CAGGAGAGCG TGGGTCTCGC GGTATCATTG CAGCACTGGG GCCAGATGGT AAGCCCTCCC      2100
GTATCGTAGT TATCTACACG ACGGGGAGTC AGGCAACTAT GGATGAACGA AATAGACAGA      2160
TCGCTGAGAT AGGTGCCTCA CTGATTAAGC ATTGGTAACT GTCAGACCAA GTTTACTCAT      2220
ATATACTTTA GATTGATTTA AAACTTCATT TTTAATTTAA AAGGATCTAG GTGAAGATCC      2280
TTTTTGATAA TCTCATGACC AAAATCCCTT AACGTGAGTT TTCGTTCCAC TGAGCGTCAG      2340
ACCCCGTAGA AAAGATCAAA GGATCTTCTT GAGATCCTTT TTTTCTGCGC GTAATCTGCT      2400
GCTTGCAAAC AAAAAAACCA CCGCTACCAG CGGTGGTTTG TTTGCCGGAT CAAGAGCTAC      2460
CAACTCTTTT TCCGAAGGTA ACTGGCTTCA GCAGAGCGCA GATACCAAAT ACTGTCCTTC      2520
TAGTGTAGCC GTAGTTAGGC CACCACTTCA AGAACTCTGT AGCACCGCCT ACATACCTCG      2580
CTCTGCTAAT CCTGTTACCA GTGGCTGCTG CCAGTGGCGA TAAGTCGTGT CTTACCGGGT      2640
TGGACTCAAG ACGATAGTTA CCGGATAAGG CGCAGCGGTC GGGCTGAACG GGGGGTTCGT      2700
GCACACAGCC CAGCTTGGAG CGAACGACCT ACACCGAACT GAGATACCTA CAGCGTGAGC      2760
ATTGAGAAAG CGCCACGCTT CCCGAAGGGA GAAAGGCGGA CAGGTATCCG GTAAGCGGCA      2820
GGGTCGGAAC AGGAGAGCGC ACGAGGGAGC TTCCAGGGGG AAACGCCTGG TATCTTTATA      2880
GTCCTGTCGG GTTTCGCCAC CTCTGACTTG AGCGTCGATT TTTGTGATGC TCGTCAGGGG      2940
GGCGGAGCCT ATGGAAAAAC GCCAGCAACG CGGCCTTTTT ACGGTTCCTG GCCTTTTGCT      3000
GGCCTTTTGC TCACATGTTC TTTCCTGCGT TATCCCCTGA TTCTGTGGAT AACCGTATTA      3060
CCGCCTTTGA GTGAGCTGAT ACCGCTCGCC GCAGCCGAAC GACCGAGCGC AGCGAGTCAG      3120
TGAGCGAGGA AGCGGAAGAG CGCCTGATGC GGTATTTTCT CCTTACGCAT CTGTGCGGTA      3180
TTTCACACCG CATATGGTGC ACTCTCAGTA CAATCTGCTC TGATGCCGCA TAGTTAAGCC      3240
AGTATACACT CCGCTATCGC TACGTGACTG GGTCATGGCT GCGCCCCGAC ACCCGCCAAC      3300
ACCCGTCTCC GGGAGCTGCA TGTGTCAGAG GTTTTCACCG TCATCACCGA AACGCGCGAG      3360
GCAGCTGCGG TAAAGCTCAT CAGCGTGGTC GTGAAGCGAT TCACAGATGT CTGCCTGTTC      3420
ATCCGCGTCC AGCTCGTTGA GTTTCTCCAG AAGCGTTAAT GTCTGGCTTC TGATAAAGCG      3480
GGCCATGTTA AGGGCGGTTT TTTCCTGTTT GGTCACTTGA TGCCTCCGTG TAAGGGGGAA      3540
```

```
TTTCTGTTCA TGGGGGTAAT GATACCGATG AAACGAGAGA GGATGCTCAC GATACGGGTT      3600
ACTGATGATG AACATGCCCG GTTACTGGAA CGTTGTGAGG GTAAACAACT GGCGGTATGG      3660
ATGCGGCGGG ACCAGAGAAA AATCACTCAG GGTCAATGCC AGCGCTTCGT TAATACAGAT      3720
GTAGGTGTTC CACAGGGTAG CCAGCAGCAT CCTGCGATGC AGATCCGGAA CATAATGGTG      3780
CAGGGCGCTG ACTTCCGCGT TTCCAGACTT TACGAAACAC GGAAACCGAA GACCATTCAT      3840
GTTGTTGCTC AGGTCGCAGA CGTTTTGCAG CAGCAGTCGC TTCACGTTCG CTCGCGTATC      3900
GGTGATTCAT TCTGCTAACC AGTAAGGCAA CCCCGCCAGC CTAGCCGGGT CCTCAACGAC      3960
AGGAGCACGA TCATGCGCAC CCGTGGCCAG GACCCAACGC TGCCCGAGAT GCGCCGCGTG      4020
CGGCTGCTGG AGATGGCGGA CGCGATGGAT ATGTTCTGCC AAGGGTTGGT TTGCGCATTC      4080
ACAGTTCTCC GCAAGAATTG ATTGGCTCCA ATTCTTGGAG TGGTGAATCC GTTAGCGAGG      4140
TGCCGCCGGC TTCCATTCAG GTCGAGGTGG CCCGGCTCCA TGCACCGCGA CGCAACGCGG      4200
GGAGGCAGAC AAGGTATAGG GCGGCGCCTA CAATCCATGC CAACCCGTTC CATGTGCTCG      4260
CCGAGGCGGC ATAAATCGCC GTGACGATCA GCGGTCCAGT GATCGAAGTT AGGCTGGTAA      4320
GAGCCGCGAG CGATCCTTGA AGCTGTCCCT GATGGTCGTC ATCTACCTGC CTGGACAGCA      4380
TGGCCTGCAA CGCGGGCATC CCGATGCCGC CGGAAGCGAG AAGAATCATA ATGGGGAAGG      4440
CCATCCAGCC TCGCGTCGCG AACGCCAGCA AGACGTAGCC CAGCGCGTCG GCCGCCATGC      4500
CGGCGATAAT GGCCTGCTTC TCGCCGAAAC GTTGGTGGC GGGACCAGTG ACGAAGGCTT       4560
GAGCGAAGCG GTCCTCGCCG AAAATGACCC AGAGCGCTGC CGGCACCTGT CCTACGAGTT      4620
GCATGATAAA GAAGACAGTC ATAAGTGCGG CGACGATAGT CATGCCCGC GCCCACCGGA       4680
AGGAGCTGAC TGGGTTGAAG GCTCTCAAGG GCATCGGTCG ACGCTCTCCC TTATGCGACT      4740
CCTGCATTAG GAAGCAGCCC AGTAGTAGGT TGAGGCCGTT GAGCACCGCC GCCGCAAGGA      4800
ATGGTGCATG CAAGGAGATG GCGCCCAACA GTCCCCGGC CACGGGGCCT GCCACCATAC       4860
CCACGCCGAA ACAAGCGCTC ATGAGCCCGA AGTGGCGAGC CCGATCTTCC CCATCGGTGA      4920
TGTCGGCGAT ATAGGCGCCA GCAACCGCAC CTGTGGCGCC GGTGATGCCG GCCACGATGC      4980
GTCCGGCGTA GAGGATCCGG AGCTTATCGA CTGCACGGTG CACCAATGCT TCTGGCGTCA      5040
GGCAGCCATC GGAAGCTGTG GTATGGCTGT GCAGGTCGTA AATCACTGCA TAATTCGTGT      5100
CGCTCAAGGC GCACTCCCGT TCTGGATAAT GTTTTTTGCG CCGACATCAT AACGGTTCTG      5160
GCAAATATTC TGAAATGAGC TGTTGACAAT TAATCATCGG CTCGTATAAT GTGTGGAATT      5220
GTGAGCGGAT AACAATTTCA CACAGGAAAC A                                    5251
```

( 2 ) INFORMATION FOR SEQ ID NO:9:

( i ) SEQUENCE CHARACTERISTICS:
        ( A ) LENGTH: 6571 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
GAATTCATGA AACAATACCA AGATTTAATT AAAGACATTT TTGAAAATGG TTATGAAACC        60
GATGATCGTA CAGGCACAGG AACAATTGCT CTGTTCGGAT CTAAATTACG CTGGGATTTA       120
ACTAAAGGTT TTCCTGCGGT AACAACTAAG AAGCTCGCCT GGAAAGCTTG CATTGCTGAG       180
CTAATATGGT TTTTATCAGG AAGCACAAAT GTCAATGATT TACGATTAAT TCAACACGAT       240
```

-continued

| | | | | | |
|---|---|---|---|---|---|
| TCGTTAATCC | AAGGCAAAAC | AGTCTGGGAT | GAAAATTACG | AAAATCAAGC | AAAAGATTTA | 300
| GGATACCATA | GCGGTGAACT | TGGTCCAATT | TATGGAAAAC | AGTGGCGTGA | TTTTGGTGGT | 360
| GTAGACCAAA | TTATAGAAGT | TATTGATCGT | ATTAAAAAAC | TGCCAAATGA | TAGGCGTCAA | 420
| ATTGTTTCTG | CATGGAATCC | AGCTGAACTT | AAATATATGG | CATTACCGCC | TTGTCATATG | 480
| TTCTATCAGT | TTAATGTGCG | TAATGGCTAT | TTGGATTTGC | AGTGGTATCA | ACGCTCAGTA | 540
| GATGTTTTCT | TGGGTCTACC | GTTAATATT | GCGTCATATG | CTACGTTAGT | TCATATTGTA | 600
| GCTAAGATGT | GTAATCTTAT | TCCAGGGGAT | TTGATATTTT | CTGGTGGTAA | TACTCATATC | 660
| TATATGAATC | ACGTAGAACA | ATGTAAAGAA | ATTTTGAGGC | GTGAACCTAA | AGAGCTCTGC | 720
| CTCGCAGAGG | GCACTCGGAT | CTTCGATCCG | GTCACCGGTA | CAACGCATCG | CATCGAGGAT | 780
| GTTGTCGATG | GGCGCAAGCC | TATTCATGTC | GTGGCTGCTG | CCAAGGACGG | AACGCTGCAT | 840
| GCGCGGCCCG | TGGTGTCCTG | GTTCGACCAG | GGAACGCGGG | ATGTGATCGG | GTTGCGGATC | 900
| GCCGGTGGCG | CCATCGTGTG | GGCGACACCC | GATCACAAGG | TGCTGACAGA | GTACGGCTGG | 960
| CGTGCCGCCG | GGGAACTCCG | CAAGGGAGAC | AGGGTGGCGC | AACCGCGACG | CTTCGATGGA | 1020
| TTCGGTGACA | GTGCGCCGAT | TCCGGCGGAT | CATGCCCGGC | TGCTTGGCTA | CCTGATCGGA | 1080
| GATGGCAGGG | ATGGTTGGGT | GGGGGGCAAG | ACTCCGATCA | ACTTCATCAA | TGTTCAGCGG | 1140
| GCGCTCATTG | ACGACGTGAC | GCGAATCGCT | GCGACGCTCG | GTTGCGCGGC | CCATCCGCAG | 1200
| GGGCGTATCT | CACTCGCGAT | CGCTCATCGA | CCCGGTGAGC | GCAACGGTGT | GGCAGACCTT | 1260
| TGTCAGCAGG | CCGGTATCTA | CGGCAAGCTC | GCGTGGGAGA | AGACGATTCC | GAATTGGTTC | 1320
| TTCGAGCCGG | ACATCGCGGC | CGACATTGTC | GGCAATCTGC | TCTTCGGCCT | GTTCGAAAGC | 1380
| GACGGGTGGG | TGAGCCGGGA | ACAGACCGGG | GCACTTCGGG | TCGGTTACAC | GACGACCTCT | 1440
| GAACAACTCG | CGCATCAGAT | TCATTGGCTG | CTGCTGCGGT | TCGGTGTCGG | GAGCACCGTT | 1500
| CGAGATTACG | ATCCGACCCA | GAAGCGGCCG | AGCATCGTCA | ACGGTCGACG | GATCCAGAGC | 1560
| AAACGTCAAG | TGTTCGAGGT | CCGGATCTCG | GGTATGGATA | ACGTCACGGC | ATTCGCGGAG | 1620
| TCAGTTCCCA | TGTGGGGGCC | GCGCGGTGCC | GCGCTTATCC | AGGCGATTCC | AGAAGCCACG | 1680
| CAGGGGCGGC | GTCGTGGATC | GCAAGCGACA | TATCTGGCTG | CAGAGATGAC | CGATGCCGTG | 1740
| CTGAATTATC | TGGACGAGCG | CGGCGTGACC | GCGCAGGAGG | CCGCGGCCAT | GATCGGTGTA | 1800
| GCTTCCGGGG | ACCCCGCGG | TGGAATGAAG | CAGGTCTTAG | GTGCCAGCCG | CCTTCGTCGG | 1860
| GATCGCGTGC | AGGCGCTCGC | GGATGCCCTG | GATGACAAAT | TCCTGCACGA | CATGCTGGCG | 1920
| GAAGAACTCC | GCTATTCCGT | GATCCGAGAA | GTGCTGCCAA | CGCGGCGGGC | ACGAACGTTC | 1980
| GACCTCGAGG | TCGAGGAACT | GCACACCCTC | GTCGCCGAAG | GGGTTGTCGT | GCACAACTGT | 2040
| GAACTAGTAA | TAAGTGGTCT | ACCTTATAAA | TTCCGATATC | TTTCTACTAA | AGAACAATTA | 2100
| AAATATGTTC | TTAAACTTAG | GCCTAAAGAT | TTCGTTCTTA | ACAACTATGT | ATCACACCCT | 2160
| CCTATTAAAG | GAAAGATGGC | GGTGTAACTG | CAGCCAAGCT | TCTGTTTTGG | CGGATGAGAG | 2220
| AAGATTTTCA | GCCTGATACA | GATTAAATCA | GAACGCAGAA | GCGGTCTGAT | AAAACAGAAT | 2280
| TTGCCTGGCG | GCAGTAGCGC | GGTGGTCCCA | CCTGACCCCA | TGCCGAACTC | AGAAGTGAAA | 2340
| CGCCGTAGCG | CCGATGGTAG | TGTGGGGTCT | CCCCATGCGA | GAGTAGGGAA | CTGCCAGGCA | 2400
| TCAAATAAAA | CGAAAGGCTC | AGTCGAAAGA | CTGGGCCTTT | CGTTTATCT | GTTGTTTGTC | 2460
| GGTGAACGCT | CTCCTGAGTA | GGACAAATCC | GCCGGGAGCG | GATTTGAACG | TTGCGAAGCA | 2520
| ACGGCCCGGA | GGGTGGCGGG | CAGGACGCCC | GCCATAAACT | GCCAGGCATC | AAATTAAGCA | 2580
| GAAGGCCATC | CTGACGGATG | GCCTTTTTGC | GTTTCTACAA | ACTCTTTTGT | TTATTTTCT | 2640

```
AAATACATTC  AAATATGTAT  CCGCTCATGA  GACAATAACC  CTGATAAATG  CTTCAATAAT   2700
ATTGAAAAAG  GAAGAGTATG  AGTATTCAAC  ATTTCCGTGT  CGCCCTTATT  CCCTTTTTTG   2760
CGGCATTTTG  CCTTCCTGTT  TTTGCTCACC  CAGAAACGCT  GGTGAAAGTA  AAAGATGCTG   2820
AAGATCAGTT  GGGTGCACGA  GTGGGTTACA  TCGAACTGGA  TCTCAACAGC  GGTAAGATCC   2880
TTGAGAGTTT  TCGCCCCGAA  GAACGTTTTC  CAATGATGAG  CACTTTTAAA  GTTCTGCTAT   2940
GTGGCGCGGT  ATTATCCCGT  GTTGACGCCG  GGCAAGAGCA  ACTCGGTCGC  CGCATACACT   3000
ATTCTCAGAA  TGACTTGGTT  GAGTACTCAC  CAGTCACAGA  AAAGCATCTT  ACGGATGGCA   3060
TGACAGTAAG  AGAATTATGC  AGTGCTGCCA  TAACCATGAG  TGATAACACT  GCGGCCAACT   3120
TACTTCTGAC  AACGATCGGA  GGACCGAAGG  AGCTAACCGC  TTTTTTGCAC  AACATGGGGG   3180
ATCATGTAAC  TCGCCTTGAT  CGTTGGGAAC  CGGAGCTGAA  TGAAGCCATA  CCAAACGACG   3240
AGCGTGACAC  CACGATGCCT  GTAGCAATGG  CAACAACGTT  GCGCAAACTA  TTAACTGGCG   3300
AACTACTTAC  TCTAGCTTCC  CGGCAACAAT  TAATAGACTG  GATGGAGGCG  GATAAAGTTG   3360
CAGGAGAGCG  TGGGTCTCGC  GGTATCATTG  CAGCACTGGG  GCCAGATGGT  AAGCCCTCCC   3420
GTATCGTAGT  TATCTACACG  ACGGGGAGTC  AGGCAACTAT  GGATGAACGA  AATAGACAGA   3480
TCGCTGAGAT  AGGTGCCTCA  CTGATTAAGC  ATTGGTAACT  GTCAGACCAA  GTTACTCAT    3540
ATATACTTTA  GATTGATTTA  AAACTTCATT  TTTAATTTAA  AAGGATCTAG  GTGAAGATCC   3600
TTTTTGATAA  TCTCATGACC  AAAATCCCTT  AACGTGAGTT  TTCGTTCCAC  TGAGCGTCAG   3660
ACCCCGTAGA  AAAGATCAAA  GGATCTTCTT  GAGATCCTTT  TTTTCTGCGC  GTAATCTGCT   3720
GCTTGCAAAC  AAAAAAACCA  CCGCTACCAG  CGGTGGTTTG  TTTGCCGGAT  CAAGAGCTAC   3780
CAACTCTTTT  TCCGAAGGTA  ACTGGCTTCA  GCAGAGCGCA  GATACCAAAT  ACTGTCCTTC   3840
TAGTGTAGCC  GTAGTTAGGC  CACCACTTCA  AGAACTCTGT  AGCACCGCCT  ACATACCTCG   3900
CTCTGCTAAT  CCTGTTACCA  GTGGCTGCTG  CCAGTGGCGA  TAAGTCGTGT  CTTACCGGGT   3960
TGGACTCAAG  ACGATAGTTA  CCGGATAAGG  CGCAGCGGTC  GGGCTGAACG  GGGGGTTCGT   4020
GCACACAGCC  CAGCTTGGAG  CGAACGACCT  ACACCGAACT  GAGATACCTA  CAGCGTGAGC   4080
ATTGAGAAAG  CGCCACGCTT  CCCGAAGGGA  GAAAGGCGGA  CAGGTATCCG  GTAAGCGGCA   4140
GGGTCGGAAC  AGGAGAGCGC  ACGAGGGAGC  TTCCAGGGGG  AAACGCCTGG  TATCTTTATA   4200
GTCCTGTCGG  GTTTCGCCAC  CTCTGACTTG  AGCGTCGATT  TTTGTGATGC  TCGTCAGGGG   4260
GGCGGAGCCT  ATGGAAAAAC  GCCAGCAACG  CGGCCTTTTT  ACGGTTCCTG  GCCTTTTGCT   4320
GGCCTTTTGC  TCACATGTTC  TTTCCTGCGT  TATCCCCTGA  TTCTGTGGAT  AACCGTATTA   4380
CCGCCTTTGA  GTGAGCTGAT  ACCGCTCGCC  GCAGCCGAAC  GACCGAGCGC  AGCGAGTCAG   4440
TGAGCGAGGA  AGCGGAAGAG  CGCCTGATGC  GGTATTTTCT  CCTTACGCAT  CTGTGCGGTA   4500
TTTCACACCG  CATATGGTGC  ACTCTCAGTA  CAATCTGCTC  TGATGCCGCA  TAGTTAAGCC   4560
AGTATACACT  CCGCTATCGC  TACGTGACTG  GGTCATGGCT  GCGCCCCGAC  ACCCGCCAAC   4620
ACCCGTCTCC  GGGAGCTGCA  TGTGTCAGAG  GTTTTCACCG  TCATCACCGA  AACGCGCGAG   4680
GCAGCTGCGG  TAAAGCTCAT  CAGCGTGGTC  GTGAAGCGAT  TCACAGATGT  CTGCCTGTTC   4740
ATCCGCGTCC  AGCTCGTTGA  GTTTCTCCAG  AAGCGTTAAT  GTCTGGCTTC  TGATAAAGCG   4800
GGCCATGTTA  AGGGCGGTTT  TTTCCTGTTT  GGTCACTTGA  TGCCTCCGTG  TAAGGGGGAA   4860
TTTCTGTTCA  TGGGGGTAAT  GATACCGATG  AAACGAGAGA  GGATGCTCAC  GATACGGGTT   4920
ACTGATGATG  AACATGCCCG  GTTACTGGAA  CGTTGTGAGG  GTAAACAACT  GGCGGTATGG   4980
ATGCGGCGGG  ACCAGAGAAA  AATCACTCAG  GGTCAATGCC  AGCGCTTCGT  TAATACAGAT   5040
```

-continued

```
GTAGGTGTTC  CACAGGGTAG  CCAGCAGCAT  CCTGCGATGC  AGATCCGGAA  CATAATGGTG    5100
CAGGGCGCTG  ACTTCCGCGT  TTCCAGACTT  TACGAAACAC  GGAAACCGAA  GACCATTCAT    5160
GTTGTTGCTC  AGGTCGCAGA  CGTTTTGCAG  CAGCAGTCGC  TTCACGTTCG  CTCGCGTATC    5220
GGTGATTCAT  TCTGCTAACC  AGTAAGGCAA  CCCCGCCAGC  CTAGCCGGGT  CCTCAACGAC    5280
AGGAGCACGA  TCATGCGCAC  CCGTGGCCAG  GACCCAACGC  TGCCCGAGAT  GCGCCGCGTG    5340
CGGCTGCTGG  AGATGGCGGA  CGCGATGGAT  ATGTTCTGCC  AAGGGTTGGT  TTGCGCATTC    5400
ACAGTTCTCC  GCAAGAATTG  ATTGGCTCCA  ATTCTTGGAG  TGGTGAATCC  GTTAGCGAGG    5460
TGCCGCCGGC  TTCCATTCAG  GTCGAGGTGG  CCCGGCTCCA  TGCACCGCGA  CGCAACGCGG    5520
GGAGGCAGAC  AAGGTATAGG  GCGGCGCCTA  CAATCCATGC  CAACCCGTTC  CATGTGCTCG    5580
CCGAGGCGGC  ATAAATCGCC  GTGACGATCA  GCGGTCCAGT  GATCGAAGTT  AGGCTGGTAA    5640
GAGCCGCGAG  CGATCCTTGA  AGCTGTCCCT  GATGGTCGTC  ATCTACCTGC  CTGGACAGCA    5700
TGGCCTGCAA  CGCGGGCATC  CCGATGCCGC  CGGAAGCGAG  AAGAATCATA  ATGGGGAAGG    5760
CCATCCAGCC  TCGCGTCGCG  AACGCCAGCA  AGACGTAGCC  CAGCGCGTCG  GCCGCCATGC    5820
CGGCGATAAT  GGCCTGCTTC  TCGCCGAAAC  GTTTGGTGGC  GGGACCAGTG  ACGAAGGCTT    5880
GAGCGAAGCG  GTCCTCGCCG  AAAATGACCC  AGAGCGCTGC  CGGCACCTGT  CCTACGAGTT    5940
GCATGATAAA  GAAGACAGTC  ATAAGTGCGG  CGACGATAGT  CATGCCCGC   GCCCACCGGA    6000
AGGAGCTGAC  TGGGTTGAAG  GCTCTCAAGG  GCATCGGTCG  ACGCTCTCCC  TTATGCGACT    6060
CCTGCATTAG  GAAGCAGCCC  AGTAGTAGGT  TGAGGCCGTT  GAGCACCGCC  GCCGCAAGGA    6120
ATGGTGCATG  CAAGGAGATG  GCGCCCAACA  GTCCCCCGGC  CACGGGGCCT  GCCACCATAC    6180
CCACGCCGAA  ACAAGCGCTC  ATGAGCCCGA  AGTGGCGAGC  CCGATCTTCC  CCATCGGTGA    6240
TGTCGGCGAT  ATAGGCGCCA  GCAACCGCAC  CTGTGGCGCC  GGTGATGCCG  GCCACGATGC    6300
GTCCGGCGTA  GAGGATCCGG  AGCTTATCGA  CTGCACGGTG  CACCAATGCT  TCTGGCGTCA    6360
GGCAGCCATC  GGAAGCTGTG  GTATGGCTGT  GCAGGTCGTA  AATCACTGCA  TAATTCGTGT    6420
CGCTCAAGGC  GCACTCCCGT  TCTGGATAAT  GTTTTTTGCG  CCGACATCAT  AACGGTTCTG    6480
GCAAATATTC  TGAAATGAGC  TGTTGACAAT  TAATCATCGG  CTCGTATAAT  GTGTGGAATT    6540
GTGAGCGGAT  AACAATTTCA  CACAGGAAAC  A                                    6571
```

( 2 ) INFORMATION FOR SEQ ID NO:10:

( i ) SEQUENCE CHARACTERISTICS:
        ( A ) LENGTH: 6571 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
GAATTCATGA  AACAATACCA  AGATTTAATT  AAAGACATTT  TTGAAAATGG  TTATGAAACC     60
GATGATCGTA  CAGGCACAGG  AACAATTGCT  CTGTTCGGAT  CTAAATTACG  CTGGGATTTA    120
ACTAAAGGTT  TTCCTGCGGT  AACAACTAAG  AAGCTCGCCT  GGAAAGCTTG  CATTGCTGAG    180
CTAATATGGT  TTTTATCAGG  AAGCACAAAT  GTCAATGATT  TACGATTAAT  TCAACACGAT    240
TCGTTAATCC  AAGGCAAAAC  AGTCTGGGAT  GAAAATTACG  AAAATCAAGC  AAAAGATTTA    300
GGATACCATA  GCGGTGAACT  TGGTCCAATT  TATGGAAAAC  AGTGGCGTGA  TTTTGGTGGT    360
GTAGACCAAA  TTATAGAAGT  TATTGATCGT  ATTAAAAAAC  TGCCAAATGA  TAGGCGTCAA    420
ATTGTTTCTG  CATGGAATCC  AGCTGAACTT  AAATATATGG  CATTACCGCC  TTGTCATATG    480
```

```
TTCTATCAGT TTAATGTGCG TAATGGCTAT TTGGATTTGC AGTGGTATCA ACGCTCAGTA    540
GATGTTTTCT TGGGTCTACC GTTTAATATT GCGTCATATG CTACGTTAGT TCATATTGTA    600
GCTAAGATGT GTAATCTTAT TCCAGGGGAT TTGATATTTT CTGGTGGTAA TACTCATATC    660
TATATGAATC ACGTAGAACA ATGTAAAGAA ATTTGAGGC GTGAACCTAA AGAGCTCTGC     720
CTCGCAGAGG GCACTCGGAT CTTCGATCCG GTCACCGGTA CAACGCATCG CATCGAGGAT    780
GTTGTCGATG GGCGCAAGCC TATTCATGTC GTGGCTGCTG CCAAGGACGG AACGCTGCAT    840
GCGCGGCCCG TGGTGTCCTG GTTCGACCAG GGAACGCGGG ATGTGATCGG GTTGCGGATC    900
GCCGGTGGCG CCATCGTGTG GGCGACACCC GATCACAAGG TGCTGACAGA GTACGGCTGG    960
CGTGCCGCCG GGGAACTCCG CAAGGGAGAC AGGGTGGCGC AACCGCGACG CTTCGATGGA   1020
TTCGGTGACA GTGCGCCGAT TCCGGCGGAT CATGCCCGGC TGCTTGGCTA CCTGATCGGA   1080
GATGGCAGGG ATGGTTGGGT GGGGGGCAAG ACTCCGATCA ACTTCATCAA TGTTCAGCGG   1140
GCGCTCATTG ACGACGTGAC GCGAATCGCT GCGACGCTCG GTTGCGCGGC CCATCCGCAG   1200
GGGCGTATCT CACTCGCGAT CGCTCATCGA CCCGGTGAGC GCAACGGTGT GGCAGACCTT   1260
TGTCAGCAGG CCGGTATCTA CGGCAAGCTC GCGTGGGAGA AGACGATTCC GAATTGGTTC   1320
TTCGAGCCGG ACATCGCGGC CGACATTGTC GGCAATCTGC TCTTCGGCCT GTTCGAAAGC   1380
GACGGGTGGG TGAGCCGGGA ACAGACCGGG GCACTTCGGG TCGGTTACAC GACGACCTCT   1440
GAACAACTCG CGCATCAGAT TCATTGGCTG CTGCTGCGGT TCGGTGTCGG GAGCACCGTT   1500
CGAGATTACG ATCCGACCCA GAAGCGGCCG AGCATCGTCA ACGGTCGACG GATCCAGAGC   1560
AAACGTCAAG TGTTCGAGGT CCGGATCTCG GGTATGGATA ACGTCACGGC ATTCGCGGAG   1620
TCAGTTCCCA TGTGGGGGCC GCGCGGTGCC GCGCTTATCC AGGCGATTCC AGAAGCCACG   1680
CAGGGGCGGC GTCGTGGATC GCAAGCGACA TATCTGGCTG CAGAGATGAC CGATGCCGTG   1740
CTGAATTATC TGGACGAGCG CGGCGTGACC GCGCAGGAGG CCGCGGCCAT GATCGGTGTA   1800
GCTTCCGGGG ACCCCGCGG TGGAATGAAG CAGGTCTTAG GTGCCAGCCG CCTTCGTCGG    1860
GATCGCGTGC AGGCGCTCGC GGATGCCCTG GATGACAAAT TCCTGCACGA CATGCTGGCG   1920
GAAGAACTCC GCTATTCCGT GATCCGAGAA GTGCTGCCAA CGCGGCGGGC ACGAACGTTC   1980
GACCTCGAGG TCGAGGAACT GCACACCCTC GTCGCCGAAG GGGTTGTCGT GGCCGCCTGT   2040
GAACTAGTAA TAAGTGGTCT ACCTTATAAA TTCCGATATC TTTCTACTAA AGAACAATTA   2100
AAATATGTTC TTAAACTTAG GCCTAAAGAT TTCGTTCTTA ACAACTATGT ATCACACCCT   2160
CCTATTAAAG GAAAGATGGC GGTGTAACTG CAGCCAAGCT TCTGTTTTGG CGGATGAGAG   2220
AAGATTTTCA GCCTGATACA GATTAAATCA GAACGCAGAA GCGGTCTGAT AAAACAGAAT   2280
TTGCCTGGCG GCAGTAGCGC GGTGGTCCCA CCTGACCCCA TGCCGAACTC AGAAGTGAAA   2340
CGCCGTAGCG CCGATGGTAG TGTGGGGTCT CCCCATGCGA GAGTAGGGAA CTGCCAGGCA   2400
TCAAATAAAA CGAAAGGCTC AGTCGAAAGA CTGGGCCTTT CGTTTTATCT GTTGTTTGTC   2460
GGTGAACGCT CTCCTGAGTA GGACAAATCC GCCGGGAGCG GATTTGAACG TTGCGAAGCA   2520
ACGGCCCGGA GGGTGGCGGG CAGGACGCCC GCCATAAACT GCCAGGCATC AAATTAAGCA   2580
GAAGGCCATC CTGACGGATG GCCTTTTTGC GTTCTACAA ACTCTTTTGT TTATTTTTCT    2640
AAATACATTC AAATATGTAT CCGCTCATGA GACAATAACC CTGATAAATG CTTCAATAAT   2700
ATTGAAAAAG GAAGAGTATG AGTATTCAAC ATTTCCGTGT CGCCCTTATT CCCTTTTTTG   2760
CGGCATTTTG CCTTCCTGTT TTTGCTCACC CAGAAACGCT GGTGAAAGTA AAAGATGCTG   2820
AAGATCAGTT GGGTGCACGA GTGGGTTACA TCGAACTGGA TCTCAACAGC GGTAAGATCC   2880
```

```
TTGAGAGTTT  TCGCCCCGAA  GAACGTTTTC  CAATGATGAG  CACTTTTAAA  GTTCTGCTAT    2940
GTGGCGCGGT  ATTATCCCGT  GTTGACGCCG  GGCAAGAGCA  ACTCGGTCGC  CGCATACACT    3000
ATTCTCAGAA  TGACTTGGTT  GAGTACTCAC  CAGTCACAGA  AAAGCATCTT  ACGGATGGCA    3060
TGACAGTAAG  AGAATTATGC  AGTGCTGCCA  TAACCATGAG  TGATAACACT  GCGGCCAACT    3120
TACTTCTGAC  AACGATCGGA  GGACCGAAGG  AGCTAACCGC  TTTTTTGCAC  AACATGGGGG    3180
ATCATGTAAC  TCGCCTTGAT  CGTTGGGAAC  CGGAGCTGAA  TGAAGCCATA  CCAAACGACG    3240
AGCGTGACAC  CACGATGCCT  GTAGCAATGG  CAACAACGTT  GCGCAAACTA  TTAACTGGCG    3300
AACTACTTAC  TCTAGCTTCC  CGGCAACAAT  TAATAGACTG  GATGGAGGCG  GATAAAGTTG    3360
CAGGAGAGCG  TGGGTCTCGC  GGTATCATTG  CAGCACTGGG  GCCAGATGGT  AAGCCCTCCC    3420
GTATCGTAGT  TATCTACACG  ACGGGGAGTC  AGGCAACTAT  GGATGAACGA  AATAGACAGA    3480
TCGCTGAGAT  AGGTGCCTCA  CTGATTAAGC  ATTGGTAACT  GTCAGACCAA  GTTACTCAT     3540
ATATACTTTA  GATTGATTTA  AAACTTCATT  TTTAATTTAA  AAGGATCTAG  GTGAAGATCC    3600
TTTTTGATAA  TCTCATGACC  AAAATCCCTT  AACGTGAGTT  TTCGTTCCAC  TGAGCGTCAG    3660
ACCCCGTAGA  AAAGATCAAA  GGATCTTCTT  GAGATCCTTT  TTTTCTGCGC  GTAATCTGCT    3720
GCTTGCAAAC  AAAAAAACCA  CCGCTACCAG  CGGTGGTTTG  TTTGCCGGAT  CAAGAGCTAC    3780
CAACTCTTTT  TCCGAAGGTA  ACTGGCTTCA  GCAGAGCGCA  GATACCAAAT  ACTGTCCTTC    3840
TAGTGTAGCC  GTAGTTAGGC  CACCACTTCA  AGAACTCTGT  AGCACCGCCT  ACATACCTCG    3900
CTCTGCTAAT  CCTGTTACCA  GTGGCTGCTG  CCAGTGGCGA  TAAGTCGTGT  CTTACCGGGT    3960
TGGACTCAAG  ACGATAGTTA  CCGGATAAGG  CGCAGCGGTC  GGGCTGAACG  GGGGGTTCGT    4020
GCACACAGCC  CAGCTTGGAG  CGAACGACCT  ACACCGAACT  GAGATACCTA  CAGCGTGAGC    4080
ATTGAGAAAG  CGCCACGCTT  CCCGAAGGGA  GAAAGGCGGA  CAGGTATCCG  GTAAGCGGCA    4140
GGGTCGGAAC  AGGAGAGCGC  ACGAGGGAGC  TTCCAGGGGG  AAACGCCTGG  TATCTTTATA    4200
GTCCTGTCGG  GTTTCGCCAC  CTCTGACTTG  AGCGTCGATT  TTTGTGATGC  TCGTCAGGGG    4260
GGCGGAGCCT  ATGGAAAAAC  GCCAGCAACG  CGGCCTTTTT  ACGGTTCCTG  GCCTTTTGCT    4320
GGCCTTTTGC  TCACATGTTC  TTTCCTGCGT  TATCCCCTGA  TTCTGTGGAT  AACCGTATTA    4380
CCGCCTTTGA  GTGAGCTGAT  ACCGCTCGCC  GCAGCCGAAC  GACCGAGCGC  AGCGAGTCAG    4440
TGAGCGAGGA  AGCGGAAGAG  CGCCTGATGC  GGTATTTTCT  CCTTACGCAT  CTGTGCGGTA    4500
TTTCACACCG  CATATGGTGC  ACTCTCAGTA  CAATCTGCTC  TGATGCCGCA  TAGTTAAGCC    4560
AGTATACACT  CCGCTATCGC  TACGTGACTG  GGTCATGGCT  GCGCCCCGAC  ACCCGCCAAC    4620
ACCCGTCTCC  GGGAGCTGCA  TGTGTCAGAG  GTTTTCACCG  TCATCACCGA  AACGCGCGAG    4680
GCAGCTGCGG  TAAAGCTCAT  CAGCGTGGTC  GTGAAGCGAT  TCACAGATGT  CTGCCTGTTC    4740
ATCCGCGTCC  AGCTCGTTGA  GTTTCTCCAG  AAGCGTTAAT  GTCTGGCTTC  TGATAAAGCG    4800
GGCCATGTTA  AGGGCGGTTT  TTTCCTGTTT  GGTCACTTGA  TGCCTCCGTG  TAAGGGGGAA    4860
TTTCTGTTCA  TGGGGGTAAT  GATACCGATG  AAACGAGAGA  GGATGCTCAC  GATACGGGTT    4920
ACTGATGATG  AACATGCCCG  GTTACTGGAA  CGTTGTGAGG  GTAAACAACT  GGCGGTATGG    4980
ATGCGGCGGG  ACCAGAGAAA  AATCACTCAG  GGTCAATGCC  AGCGCTTCGT  TAATACAGAT    5040
GTAGGTGTTC  CACAGGGTAG  CCAGCAGCAT  CCTGCGATGC  AGATCCGGAA  CATAATGGTG    5100
CAGGGCGCTG  ACTTCCGCGT  TTCCAGACTT  TACGAAACAC  GGAAACCGAA  GACCATTCAT    5160
GTTGTTGCTC  AGGTCGCAGA  CGTTTTGCAG  CAGCAGTCGC  TTCACGTTCG  CTCGCGTATC    5220
GGTGATTCAT  TCTGCTAACC  AGTAAGGCAA  CCCCGCCAGC  CTAGCCGGGT  CCTCAACGAC    5280
```

-continued

| | | | | | |
|---|---|---|---|---|---|
| AGGAGCACGA | TCATGCGCAC | CCGTGGCCAG | GACCCAACGC | TGCCCGAGAT | GCGCCGCGTG | 5340 |
| CGGCTGCTGG | AGATGGCGGA | CGCGATGGAT | ATGTTCTGCC | AAGGGTTGGT | TTGCGCATTC | 5400 |
| ACAGTTCTCC | GCAAGAATTG | ATTGGCTCCA | ATTCTTGGAG | TGGTGAATCC | GTTAGCGAGG | 5460 |
| TGCCGCCGGC | TTCCATTCAG | GTCGAGGTGG | CCCGGCTCCA | TGCACCGCGA | CGCAACGCGG | 5520 |
| GGAGGCAGAC | AAGGTATAGG | GCGGCGCCTA | CAATCCATGC | CAACCCGTTC | CATGTGCTCG | 5580 |
| CCGAGGCGGC | ATAAATCGCC | GTGACGATCA | GCGGTCCAGT | GATCGAAGTT | AGGCTGGTAA | 5640 |
| GAGCCGCGAG | CGATCCTTGA | AGCTGTCCCT | GATGGTCGTC | ATCTACCTGC | CTGGACAGCA | 5700 |
| TGGCCTGCAA | CGCGGGCATC | CCGATGCCGC | CGGAAGCGAG | AAGAATCATA | ATGGGGAAGG | 5760 |
| CCATCCAGCC | TCGCGTCGCG | AACGCCAGCA | AGACGTAGCC | CAGCGCGTCG | GCCGCCATGC | 5820 |
| CGGCGATAAT | GGCCTGCTTC | TCGCCGAAAC | GTTGGTGGC | GGGACCAGTG | ACGAAGGCTT | 5880 |
| GAGCGAAGCG | GTCCTCGCCG | AAAATGACCC | AGAGCGCTGC | CGGCACCTGT | CCTACGAGTT | 5940 |
| GCATGATAAA | GAAGACAGTC | ATAAGTGCGG | CGACGATAGT | CATGCCCCGC | GCCCACCGGA | 6000 |
| AGGAGCTGAC | TGGGTTGAAG | GCTCTCAAGG | GCATCGGTCG | ACGCTCTCCC | TTATGCGACT | 6060 |
| CCTGCATTAG | GAAGCAGCCC | AGTAGTAGGT | TGAGGCCGTT | GAGCACCGCC | GCCGCAAGGA | 6120 |
| ATGGTGCATG | CAAGGAGATG | GCGCCCAACA | GTCCCCGGC | CACGGGCCT | GCCACCATAC | 6180 |
| CCACGCCGAA | ACAAGCGCTC | ATGAGCCCGA | AGTGGCGAGC | CCGATCTTCC | CCATCGGTGA | 6240 |
| TGTCGGCGAT | ATAGGCGCCA | GCAACCGCAC | CTGTGGCGCC | GGTGATGCCG | GCCACGATGC | 6300 |
| GTCCGGCGTA | GAGGATCCGG | AGCTTATCGA | CTGCACGGTG | CACCAATGCT | TCTGGCGTCA | 6360 |
| GGCAGCCATC | GGAAGCTGTG | GTATGGCTGT | GCAGGTCGTA | AATCACTGCA | TAATTCGTGT | 6420 |
| CGCTCAAGGC | GCACTCCCGT | TCTGGATAAT | GTTTTTGCG | CCGACATCAT | AACGGTTCTG | 6480 |
| GCAAATATTC | TGAAATGAGC | TGTTGACAAT | TAATCATCGG | CTCGTATAAT | GTGTGGAATT | 6540 |
| GTGAGCGGAT | AACAATTTCA | CACAGGAAAC | A | | | 6571 |

( 2 ) INFORMATION FOR SEQ ID NO:11:

( i ) SEQUENCE CHARACTERISTICS:
        ( A ) LENGTH: 1323 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

| | | | | | |
|---|---|---|---|---|---|
| TGCCTCGCAG | AGGGCACTCG | GATCTTCGAT | CCGGTCACCG | GTACAACGCA | TCGCATCGAG | 60 |
| GATGTTGTCG | ATGGGCGCAA | GCCTATTCAT | GTCGTGGCTG | CTGCCAAGGA | CGGAACGCTG | 120 |
| CATGCGCGGC | CCGTGGTGTC | CTGGTTCGAC | CAGGGAACGC | GGGATGTGAT | CGGGTTGCGG | 180 |
| ATCGCCGGTG | GCGCCATCGT | GTGGGCGACA | CCCGATCACA | AGGTGCTGAC | AGAGTACGGC | 240 |
| TGGCGTGCCG | CCGGGGAACT | CCGCAAGGGA | GACAGGGTGG | CGCAACCGCG | ACGCTTCGAT | 300 |
| GGATTCGGTG | ACAGTGCGCC | GATTCCGGCG | GATCATGCCC | GGCTGCTTGG | CTACCTGATC | 360 |
| GGAGATGGCA | GGGATGGTTG | GGTGGGGGGC | AAGACTCCGA | TCAACTTCAT | CAATGTTCAG | 420 |
| CGGGCGCTCA | TTGACGACGT | GACGCGAATC | GCTGCGACGC | TCGGTTGCGC | GGCCCATCCG | 480 |
| CAGGGGCGTA | TCTCACTCGC | GATCGCTCAT | CGACCCGGTG | AGCGCAACGG | TGTGGCAGAC | 540 |
| CTTTGTCAGC | AGGCCGGTAT | CTACGGCAAG | CTCGCGTGGG | AGAAGACGAT | TCCGAATTGG | 600 |
| TTCTTCGAGC | CGGACATCGC | GGCCGACATT | GTCGGCAATC | TGCTCTTCGG | CCTGTTCGAA | 660 |

|            |            |            |            |            |            |      |
|------------|------------|------------|------------|------------|------------|------|
| AGCGACGGGT | GGGTGAGCCG | GGAACAGACC | GGGGCACTTC | GGGTCGGTTA | CACGACGACC | 720  |
| TCTGAACAAC | TCGCGCATCA | GATTCATTGG | CTGCTGCTGC | GGTTCGGTGT | CGGGAGCACC | 780  |
| GTTCGAGATT | ACGATCCGAC | CCAGAAGCGG | CCGAGCATCG | TCAACGGTCG | ACGGATCCAG | 840  |
| AGCAAACGTC | AAGTGTTCGA | GGTCCGGATC | TCGGGTATGG | ATAACGTCAC | GGCATTCGCG | 900  |
| GAGTCAGTTC | CCATGTGGGG | GCCGCGCGGT | GCCGCGCTTA | TCCAGGCGAT | TCCAGAAGCC | 960  |
| ACGCAGGGGC | GGCGTCGTGG | ATCGCAAGCG | ACATATCTGG | CTGCAGAGAT | GACCGATGCC | 1020 |
| GTGCTGAATT | ATCTGGACGA | GCGCGGCGTG | ACCGCGCAGG | AGGCCGCGGC | CATGATCGGT | 1080 |
| GTAGCTTCCG | GGGACCCCCG | CGGTGGAATG | AAGCAGGTCT | TAGGTGCCAG | CCGCCTTCGT | 1140 |
| CGGGATCGCG | TGCAGGCGCT | CGCGGATGCC | CTGGATGACA | AATTCCTGCA | CGACATGCTG | 1200 |
| GCGGAAGAAC | TCCGCTATTC | CGTGATCCGA | GAAGTGCTGC | CAACGCGGCG | GCACGAACG  | 1260 |
| TTCGACCTCG | AGGTCGAGGA | ACTGCACACC | CTCGTCGCCG | AAGGGGTTGT | CGTGCACAAC | 1320 |
| TGT        |            |            |            |            |            | 1323 |

( 2 ) INFORMATION FOR SEQ ID NO:12:

( i ) SEQUENCE CHARACTERISTICS:
        ( A ) LENGTH: 1323 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

|            |            |            |            |            |            |      |
|------------|------------|------------|------------|------------|------------|------|
| TGCCTCGCAG | AGGGCACTCG | GATCTTCGAT | CCGGTCACCG | GTACAACGCA | TCGCATCGAG | 60   |
| GATGTTGTCG | ATGGGCGCAA | GCCTATTCAT | GTCGTGGCTG | CTGCCAAGGA | CGGAACGCTG | 120  |
| CATGCGCGGC | CCGTGGTGTC | CTGGTTCGAC | CAGGGAACGC | GGGATGTGAT | CGGGTTGCGG | 180  |
| ATCGCCGGTG | GCGCCATCGT | GTGGGCGACA | CCCGATCACA | AGGTGCTGAC | AGAGTACGGC | 240  |
| TGGCGTGCCG | CCGGGGAACT | CCGCAAGGGA | GACAGGGTGG | CGCAACCGCG | ACGCTTCGAT | 300  |
| GGATTCGGTG | ACAGTGCGCC | GATTCCGGCG | GATCATGCCC | GGCTGCTTGG | CTACCTGATC | 360  |
| GGAGATGGCA | GGGATGGTTG | GGTGGGGGGC | AAGACTCCGA | TCAACTTCAT | CAATGTTCAG | 420  |
| CGGGCGCTCA | TTGACGACGT | GACGCGAATC | GCTGCGACGC | TCGGTTGCGC | GGCCCATCCG | 480  |
| CAGGGGCGTA | TCTCACTCGC | GATCGCTCAT | CGACCCGGTG | AGCGCAACGG | TGTGGCAGAC | 540  |
| CTTTGTCAGC | AGGCCGGTAT | CTACGGCAAG | CTCGCGTGGG | AGAAGACGAT | TCCGAATTGG | 600  |
| TTCTTCGAGC | CGGACATCGC | GGCCGACATT | GTCGGCAATC | TGCTCTTCGG | CCTGTTCAAA | 660  |
| AGCGACGGGT | GGGTGAGCCG | GGAACAGACC | GGGGCACTTC | GGGTCGGTTA | CACGACGACC | 720  |
| TCTGAACAAC | TCGCGCATCA | GATTCATTGG | CTGCTGCTGC | GGTTCGGTGT | CGGGAGCACC | 780  |
| GTTCGAGATT | ACGATCCGAC | CCAGAAGCGG | CCGAGCATCG | TCAACGGTCG | ACGGATCCAG | 840  |
| AGCAAACGTC | AAGTGTTCGA | GGTCCGGATC | TCGGGTATGG | ATAACGTCAC | GGCATTCGCG | 900  |
| GAGTCAGTTC | CCATGTGGGG | GCCGCGCGGT | GCCGCGCTTA | TCCAGGCGAT | TCCAGAAGCC | 960  |
| ACGCAGGGGC | GGCGTCGTGG | ATCGCAAGCG | ACATATCTGG | CTGCAGAGAT | GACCGATGCC | 1020 |
| GTGCTGAATT | ATCTGGACGA | GCGCGGCGTG | ACCGCGCAGG | AGGCCGCGGC | CATGATCGGT | 1080 |
| GTAGCTTCCG | GGGACCCCCG | CGGTGGAATG | AAGCAGGTCT | TAGGTGCCAG | CCGCCTTCGT | 1140 |
| CGGGATCGCG | TGCAGGCGCT | CGCGGATGCC | CTGGATGACA | AATTCCTGCA | CGACATGCTG | 1200 |
| GCGGAAGAAC | TCCGCTATTC | CGTGATCCGA | GAAGTGCTGC | CAACGCGGCG | GCACGAACG  | 1260 |
| TTCGACCTCG | AGGTCGAGGA | ACTGCACACC | CTCGTCGCCG | AAGGGGTTGT | CGTGCACAAC | 1320 |

TGT                                                                                                                 1 3 2 3

( 2 ) INFORMATION FOR SEQ ID NO:13:

( i ) SEQUENCE CHARACTERISTICS:
  ( A ) LENGTH: 1323 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:13:

```
TGCCTCGCAG   AGGGCACTCG   GATCTTCGAT   CCGGTCACCG   GTACAACGCA   TCGCATCGAG        60
GATGTTGTCG   ATGGGCGCAA   GCCTATTCAT   GTCGTGGCTG   CTGCCAAGGA   CGGAACGCTG       120
CGTGCGCGGC   CCGTGGTGTC   CTGGTTCGAC   CAGGGAACGC   GGGATGTGAT   CGGGTTGCGG       180
ATCGCCGGTG   GCGCCATCGT   GTGGGCGACA   CCCGATCACA   AGGTGCTGAC   AGAGTACGGC       240
TGGCGTGCCG   CCGGGGAACT   CCGCAAGGGA   GACAGGGTGG   CGCAACCGCG   ACGCTTCGAT       300
GGATTCGGTG   ACAGTGCGCC   GATTCCGGCG   GATCATGCCC   GGCTGCTTGG   CTACCTGATC       360
GGAGATGGCA   GGGATGGTTG   GGTGGGGGGC   AAGACTCCGA   TCAACTTCAT   CAATGTTCAG       420
CGGGCGCTCA   TTGACGACGT   GACGCGAATC   GCTGCGACGC   TCGGTTGCGC   GGCCCATCCG       480
CAGGGGCGTA   TCTCACTCGC   GATCGCTCAT   CGACCCGGTG   AGCGCAACGG   TGTGGCAGAC       540
CTTTGTCAGC   AGGCCGGTAT   CTACGGCAAG   CTCGCGTGGG   AGAAGACGAT   TCCGAATTGG       600
TTCTTCGAGC   CGGACATCGC   GGCCGACATT   GTCGGCAATC   TGCTCTTCGG   CCTGTTCGAA       660
AGCGACGGGT   GGGTGAGCCG   GGAACAGACC   GGGGCACTTC   GGGTCGGTTA   CACGACGACC       720
TCTGAACAAC   TCGCGCATCA   GATTCATTGG   CTGCTGCTGC   GGTTCGGTGT   CGGGAGCACC       780
GTTCGAGATT   ACGATCCGAC   CCAGAAGCGG   CCGAGCATCG   TCAACGGTCG   ACGGATCCAG       840
AGCAAACGTC   AAGTGTTCGA   GGTCCGGATC   TCGGGTATGG   ATAACGTCAC   GGCATTCGCG       900
GAGTCAGTTC   CCATGTGGGG   GCCGCGCGGT   GCCGCGCTTA   TCCAGGCGAT   TCCAGAAGCC       960
ACGCAGGGGC   GGCGTCGTGG   ATCGCAAGCG   ACATATCTGG   CTGCAGAGAT   GACCGATGCC      1020
GTGCTGAATT   ATCTGGACGA   GCGCGGCGTG   ACCGCGCAGG   AGGCCGCGGC   CATGATCGGT      1080
GTAGCTTCCG   GGGACCCCCG   CGGTGGAATG   AAGCAGGTCT   TAGGTGCCAG   CCGCCTTCGT      1140
CGGGATCGCG   TGCAGGCGCT   CGCGGATGCC   CTGGATGACA   AATTCCTGCA   CGACATGCTG      1200
GCGGAAGAAC   TCCGCTATTC   CGTGATCCGA   GAAGTGCTGC   CAACGCGGCG   GGCACGAACG      1260
TTCGACCTCG   AGGTCGAGGA   ACTGCACACC   CTCGTCGCCG   AAGGGGTTGT   CGTGCACAAC      1320
TGT                                                                              1323
```

( 2 ) INFORMATION FOR SEQ ID NO:14:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( i i ) MOLECULE TYPE: amino acid ( x i ) SEQUENCE DESCRIPTION: SEQ ID NO:14:

```
Asp  Leu  Ile  Lys  Asp  Ile  Phe  Glu  Asn  Gly  Tyr  Glu
 1              5                        10
```

( 2 ) INFORMATION FOR SEQ ID NO:15:

( i ) SEQUENCE CHARACTERISTICS:
   ( A ) LENGTH: 30 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:15:

TCCGAATTCA TGAAACAATA CCAAGATTTA                              30

( 2 ) INFORMATION FOR SEQ ID NO:16:

( i ) SEQUENCE CHARACTERISTICS:
      ( A ) LENGTH: 45 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:16:

CCCGGATCCA TCGATCTGCA GTTACACCGC CATCTTTCCT TTAAT             45

( 2 ) INFORMATION FOR SEQ ID NO:17:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:17:

ACCACTTATT ACTAGTTCAC AGAGCTCTTT ACCTTC                       36

( 2 ) INFORMATION FOR SEQ ID NO:18:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:18:

GAACCTAAAG AGCTCTGCCT CGCAGAGGGC ACTCGG                       36

( 2 ) INFORMATION FOR SEQ ID NO:19:

( i ) SEQUENCE CHARACTERISTICS:
      ( A ) LENGTH: 42 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:19:

ACTTATTACT AGTTCACAGT TGTGCACGAC AACCCCTTCG GC                42

( 2 ) INFORMATION FOR SEQ ID NO:20:

( i ) SEQUENCE CHARACTERISTICS:
      ( A ) LENGTH: 47 base pairs
      ( B ) TYPE: nucleic acid
      ( C ) STRANDEDNESS: single -continued ( D ) TOPOLOGY: linear ( i i ) MOLECULE TYPE: DNA (genomic)

( x i ) SEQUENCE DESCRIPTION: SEQ ID NO:20:

ACTTATTACT AGTTCACAGG CGGCCACGAC AACCCTTCGG CGACGAG     47

( 2 ) INFORMATION FOR SEQ ID NO:21:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:21:

CCGCCATCTT TCCTTTAATA GGAG     24

( 2 ) INFORMATION FOR SEQ ID NO:22:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:22:

GAACAATGTA AAGAAATTTT GAGGC     25

( 2 ) INFORMATION FOR SEQ ID NO:23:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:23:

GGGTGGCGCA ACCGCGACGC TTCG     24

( 2 ) INFORMATION FOR SEQ ID NO:24:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:24:

CGTGGGAGAA GACGATTCCG AATTGG     26

( 2 ) INFORMATION FOR SEQ ID NO:25:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:25:

GGATGACAAA TTCCTGCACG ACAT 24

(2) INFORMATION FOR SEQ ID NO:26:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:26:

GCCCGCCGCG TTGGCAGCAC TTCT 24

(2) INFORMATION FOR SEQ ID NO:27:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:27:

GGAATCGCCT GGATAAGCGC GGCA 24

(2) INFORMATION FOR SEQ ID NO:28:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:28:

CGAACAGGCC GAAGAGCAGA TTGC 24

(2) INFORMATION FOR SEQ ID NO:29:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:29:

GCCAAGCAGC CGGGCATGAT CCGC 24

(2) INFORMATION FOR SEQ ID NO:30:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:30:

GCGTTCCCTG GTCGAACCAG GACA 24

(2) INFORMATION FOR SEQ ID NO:31:

```
( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:31:

GTATGGATAA CGTCACGGCA TTCG                                                    2 4
```

INTEINS AS ANTIMICROBIAL TARGETS: GENETIC SCREENS FOR INTEIN FUNCTION

FIELD OF THE INVENTION

This invention relates to using the intein as an antimicrobial target, and testing the efficacy of agents which inhibit intein function through genetic screens for monitoring the function of protein inteins, and isolating conditional mutants thereof.

Several publications are referenced in this application. Full citations to these references is found at the end of the specification preceding the claims. These references describe the state-of-the-art to which this invention pertains.

BACKGROUND AND SIGNIFICANCE

Resistance to antimicrobial drugs is a growing global problem in the fight against infectious diseases. Screening of drugs against novel molecular targets within the microbial pathogen is therefore of paramount importance in developing new antibiotics. Inteins, which have been discovered in a variety of microbial systems, including bacterial pathogens, are novel antibiotic targets.

Inteins are protein splicing elements that occur naturally as in-frame protein fusions (Cooper and Stevens, 1993; Colston and Davis, 1994; Perler et al., 1994; Cooper and Stevens, 1995). Once excised, the intein can act as an endonuclease to mediate the movement of the insertional element to new sites (Cooper and Stevens, 1993). The spliced host protein performs the original function specified by the gene prior to the insertional event.

Acronyms for the word intein include: intervening protein sequence, protein intron, protein spacer and protein insert. Inteins must be removed post-translationally to restore function of the protein they interrupt (FIG. 1A). They are phylogenetically widespread, having been found in all three biological kingdoms, eubacteria, archaea and eukaryotes (Cooper and Stevens, 1993; Colston and Davis, 1994; Perler et al., 1994; Cooper and Stevens, 1995). Intein nomenclature parallels that for RNA splicing, whereby the coding sequences of a gene (exteins) are interrupted by sequences that specify the protein splicing element (intein) (Perler et al., 1994). The terms extein and intein refer to both the genetic material and corresponding protein products (FIG. 1A).

A precursor protein is synthesized comprising exteins interrupted by an intein. Protein splicing then results in intein excision, and extein ligation, which restores the uninterrupted reading frame to the intein-containing protein. Highly conserved sequences appear at the junction of the inteins and the exteins; His (H) and Asn (N), occur at the C-terminal end of the intein, and Ser (S), Thr (T) or Cys (C) occur immediately downstream of each splice junction (FIG. 2).

Several potential mechanisms for protein splicing have been proposed. These mechanisms generally involve nucleophilic attack on the peptide bond at the N-extein-intein junction by a nucleophilic residue which is the N-terminal amino acid of the C-extein (typically a serine, threonine or cysteine), or the conserved asparagine at the N-terminus of the intein, giving rise to a branched polypeptide chain (Xu et al., 1993; Clarke, 1994). Cyclization of the invariant Asn residue at the C terminus of the intein to succinimide then occurs (Xu et al., 1994), which leads to excision of the intein, and subsequent peptide bond formation (ligation) between the exteins (variations reviewed by Cooper et al., 1995).

Thus far, 12 inteins have been reported in various strains of bacteria, fungi and archaea (Cooper and Stevens, 1995; Fsihi et al., 1996; Pietrokovski, 1996). In addition to the discovery of three different inteins in various Mycobacteria (Davis et al., 1994; Fsihi et al., 1996), one has been found in the fungus *Candida tropicalis* (Gu et al., 1993), a close relative of the pathogen *Candida albicans*.

It is anticipated that many more inteins will be discovered as genome sequencing and research advance, and that inteins will emerge as frequent residents of genes in diverse pathogens. However, inteins are not known to exist in higher eukaryotes, including mammals. Accordingly, the use of inteins as drug targets to inhibit the growth of the pathogens in which they reside, as in the present invention, will have wide applicability against a diverse array of microbial pathogens while minimizing insult to the mammalian host.

A method for monitoring intein function would enable the further study of these critical elements involved in protein splicing, facilitating the elucidation of the exact mechanism of protein splicing, and elucidating the key functional elements in the overall mechanism. With the knowledge of the important functional elements in protein splicing, the potential inhibition of these elements can be examined, in an effort to design antimicrobial agents which can target the pathogens which possess inteins in critical genes. Furthermore, development of genetic systems that monitor intein function would provide an empirical assay for screening potential antimicrobial agents, such as those generated by combinatorial approaches.

Targeting drugs against intein function would provide a new approach to arrest growth of organisms with inteins in critical genes. For example, drugs that block the function of the intein in an important protein (the RecA protein; Davis et al., 1991, 1992) of *Mycobacterium tuberculosis* could be used to inhibit the growth of this pathogen, which causes tuberculosis. More generally, drugs that inhibit intein function would be useful antimicrobial agents for a broad spectrum of pathogens that may contain inteins, and due to the absence of inteins in mammalian genes, the administration of such anti-intein agents would not result in deleterious adverse effects.

U.S. Pat. No. 5,496,714, entitled, "Modification of protein by use of a controllable intervening protein sequence", awarded to Donald G. Comb et al., is directed to modified proteins into which has been inserted a controllable intervening protein sequence capable of excision under predetermined conditions. Although this patent does mention conditional splicing and insertion of inteins into reporter genes, it does not address the concept of using inteins as targets for antimicrobial agents.

A publication by Cooper, et al., entitled "Protein splicing of the yeast TFP1 intervening protein sequence: a model for self-excision", in EMBO Journal (1993), 12: 2575–2583, discloses protein splicing of *Saccharomyces cerevisiae* TFP1 gene product. The article describes deletion of a portion of the intein, leading to prevention of splicing of the intein, but there is no indication that inteins can be used as genetic screens for antimicrobial agents.

Additionally, a publication by Davis et al., entitled "Protein splicing in maturation of the *M. tuberculosis* RecA protein: A mechanism for tolerating a novel class of intervening sequence", Cell (1992) 71: 201–210, describes the construction of a fusion of an intein to a genetic reporter system, the β-galactosidase gene, but there is no teaching of the concept of using genetic screens for inteins as drug targets for antimicrobials.

Further, a publication by Colston et al., entitled "The ins and outs of protein splicing elements", in Molecular Microbiology (1994), 12 (3): 359–363, discloses the sequence homology at the splice sites of the known examples of protein splicing. However, there is no discussion of the concept of monitoring intein function as a method of determining the efficacy of antimicrobial agents.

Several publications discuss the properties of inteins, their functional importance and their mechanism of action. These include:

1. Davis, E. O. et al., "Novel Structure of the recA Locus of *Mycobacterium tuberculosis* Implies Processing of the Gene Product" J. Bacteriology (1991), 173: 5653–5662;
2. Belfort, M. et al., "Prokaryotic Introns and Inteins: a Panoply of Form and Function" J. Bacteriology (1995), 177: 3897–3903;
3. Dalgaard, J. "Mobile introns and inteins: friend or foe?" Trends in Genetics (1994), 10: 306–307;
4. Pietrokovski, S. "Conserved sequence features of inteins (protein introns) and their use in identifying new inteins and related proteins" Protein Science (1994), 3: 2340–2350;
5. Shao, Y. et al., "Protein Splicing: Characterization of the Aminosuccinimide Residue at the Carboxyl Terminus of the Excised Intervening Sequence" Biochemistry (1995), 34: 10844–10850; and
6. Clarke, N. D. "A proposed mechanism for the self-splicing of proteins" Proc. Natl. Acad. Sci. (1994), 91: 11084–11088.

Although each of the above-identified publications characterize protein inteins and the functional significance of these splicing elements, none of these publications identify the utility of inteins as drug screens for antimicrobial agents.

SUMMARY OF THE INVENTION

The invention provides a method of screening chemical agents (at varying concentrations) that inhibit inteins, by monitoring intein function, as a means of impairing the growth of pathogens possessing inteins in critical genes, thereby providing a new type of antimicrobial drug.

Additionally, the invention provides a genetic system to monitor intein function comprising cloning an intein of interest into a reporter gene and detecting the production of extein product.

The invention further provides a method of monitoring Mtb RecA intein function, wherein the Mtb RecA intein is derived from the *Mycobacterium tuberculosis*, which comprises creating a silent restriction site within a plasmid-borne td gene of phage T4 which results in an altered td gene; cloning the Mtb recA intein into the recipient clones; and detecting the production of thymidylate synthase (TS).

Additionally, the invention provides a method of detecting conditional splicing inteins which comprises cloning a conditional splicing intein into the plasmid-borne phage T4 td gene, and detecting the production of TS at varying temperatures.

The invention further provides a method of selecting intein mutants, including conditionally splicing inteins, which comprises cloning a wild-type intein into the plasmid-borne phage T4 td gene, mutagenizing and isolating variants that cannot produce TS, with conditionally splicing inteins being those mutants that can produce TS at one specific temperature, but not another.

These and other embodiments are disclosed or are obvious from the following detailed description.

BRIEF DESCRIPTION OF THE FIGURES

FIG. 2A shows a schematic representation of an intein and flanking exteins with conserved residues, and mutations in a non-splicing Mtb intein with the conserved histidine and asparagine residues at the C-terminus of the intein sequence substituted by alanine;

FIG. 2B shows the partial amino acid sequence of the translational product derived from the wild-type Mtb recA gene (N-Extein=SEQ. ID. NO: 1 and C-Extein=SEQ. ID. NO: 2) and from insertion of Mtb RecA intein into a selected site in the td gene (N-Extein=SEQ. ID. NO: 3 and C-Extein= SEQ. ID. NO: 4);

FIG. 3 shows the results of monitoring intein function with TS-intein fusion variants, wherein b represents a positive control with pKKtdC238 (no intein), c represents pKKtdC238Mtb, d represents pKKtdC238MtbAA, containing a splicing defective intein, and e represents pKKtdC238Mtb-ts, a temperature sensitive intein mutant;

FIG. 3B shows a polyacrylamide SDS-PAGE gel which demonstrates the resultant products from the splicing reactions, as reflected by the TS band (c);

FIG. 3C shows a Western blot with antibodies directed against the TS splicing product;

FIG. 3D shows the results of an FdUMP assay for spliced TS;

FIG. 5B SEQ. ID. NO:5 shows the DNA sequence of the uninterrupted phage T4 td gene;

FIG. 6B SEQ. ID. NO:6 shows the DNA sequence of the vector pGEM3-Zf(−);

FIG. 7B SEQ. ID. NO:7 shows the DNA sequence of the inducible expression vector pKK223-3;

FIG. 8B SEQ. ID. NO:8 shows the DNA sequence of the recipient clone pKKtdC238;

FIG. 9B SEQ. ID. NO:9 shows the DNA sequence of pKKtdC238Mtb;

FIG. 10B SEQ. ID. NO:10 shows the DNA sequence of pKKtdC238MtbAA; and

FIG. 11 shows the DNA and protein sequences of the Mtb intein SEQ. ID. NO:11, and sequence changes of two conditionally splicing mutants (mutation 1=SEQ ID. NO: 12 and mutation 2=SEQ. ID. NO: 13).

DETAILED DESCRIPTION OF THE INVENTION

The present invention relates to using the intein as an antimicrobial target, and testing the efficacy of agents that inhibit inteins, through a genetic system to monitor intein function, isolating conditional intein mutants, and monitoring potential drug interactions with pathogens possessing inteins in critical genes.

Figures 1A, 1B:
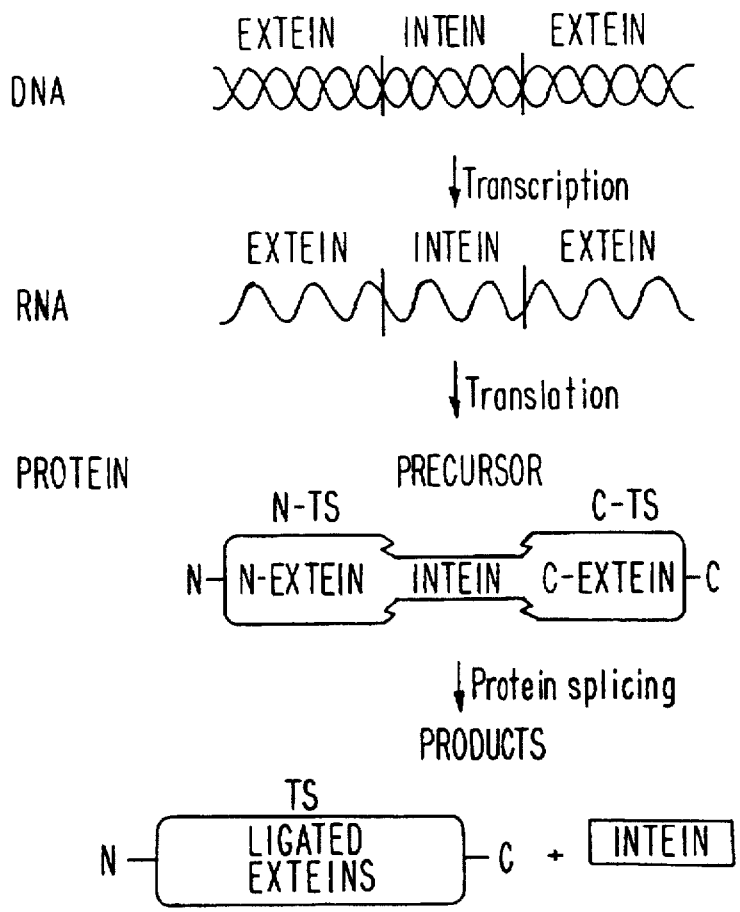
FIG. 1A shows the splicing of intein-TS (thymidylate synthase) fusion from a precursor protein to yield the ligated extein, i.e., thymidylate synthase, and the spliced intein sequence.
FIG. 1B shows the phenotype of intein-TS fusion which is used as genetic screens for intein function.

More specifically, the present invention relates to a genetic system to monitor intein function based on fusions of the *M. tuberculosis* RecA intein (Mtb intein) (Davis et al., 1991) to the thymidylate synthase (TS) reporter system. The uninterrupted phage T4 td gene, which encodes the 30 kDa TS, has been adapted for this purpose (West et al., 1986). The cloned td gene can complement *Escherichia coli* thyA cells deficient in host TS for growth on medium lacking thymine (−THY medium), conferring a $TS^+$ phenotype. In contrast, mutant td⁻ constructs in a thyA host can be selected on medium containing trimethoprim and thymine (TTM medium), indicating a $TS^-$ phenotype (Belfort et al, 1990; FIG. 1B).

Inteins are readily identifiable by virtue of conserved sequence motifs (Pietrokovski, 1994, 1996). To date, no inteins have been identified in the *E. coli* sequence database, which represents greater than 30% of the genome. Although there is some likelihood that inteins exist in *E. coli*, such a finding would not undermine the use of *E. coli* as the host cell for monitoring intein function. Genetic interruptions are readily removed by gene replacement, a technique that was in fact used to render the intron-containing td gene intronless (West et al., 1986).

Figure 3A:
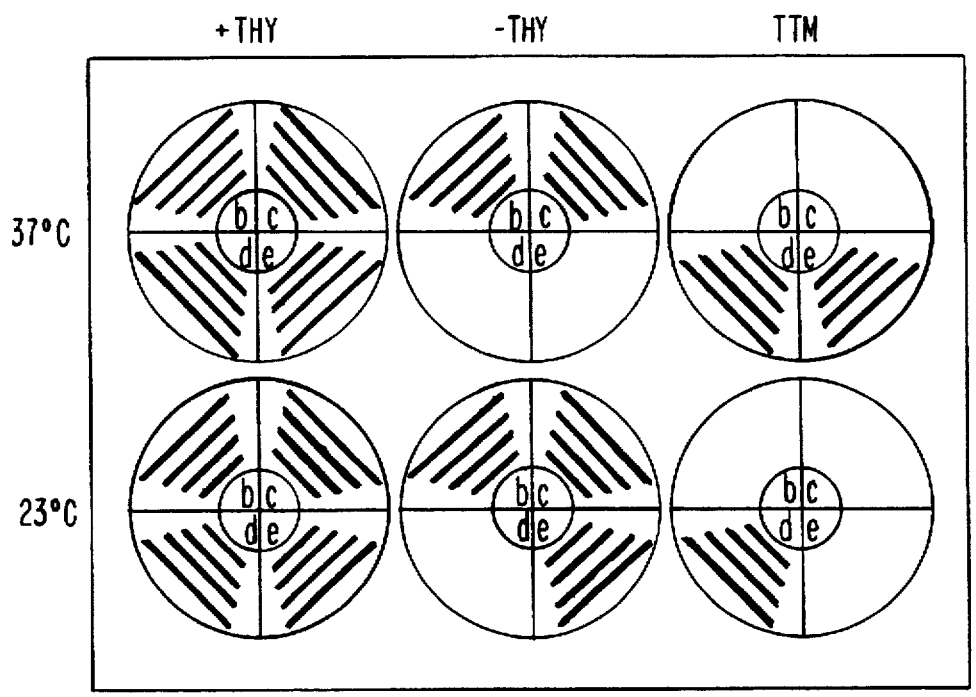
FIG. 3A shows the growth phenotypes from splicing proficient (c), splicing defective (d) and conditionally splicing (e) inteins.

In-frame fusions of the Mtb intein were made to the TS "exteins" and these constructs are $TS^+$, i.e., capable of growth on −THY but not TTM medium. In contrast, a mutant Mtb intein which is unable to splice because of critical mutations that have been introduced (terminal HN to AA mutations; FIG. 2), rendered the constructs $TS^-$, i.e., capable of growth on TTM, but not −THY medium (FIGS. 1B and 3A). These phenotypic selections were instrumental in isolating conditional intein mutants which can splice at 23° C. but not at 37° C. Thus, the present invention provides a method of monitoring intein function by detecting the production of TS.

Further, the present invention provides a method of monitoring drug-induced impairment of intein function, in addition to a method of monitoring mutation-induced inhibition of intein function.

The drug screen comprises the use of several different Mtb intein variants in the TS reporter system, i.e., a splicing-proficient intein which effectively excises the intein, yielding ligated TS, a range of conditionally splicing inteins with different phenotypic properties (mutant inteins which display temperature sensitive splicing proficiency), and a splicing defective intein. The rationale for including conditional inteins in the screen is that their splicing function is somewhat compromised by mutation, and they would therefore be likely to be more readily-inhibited by drugs targeting the intein than the wild type (Table 1). These conditional inteins serve to sensitize the drug screen, in addition to providing an initial indication of intein rather than extein targeting by the drug under investigation.

The intein-TS reporter constructs are grown in the presence and absence of drug, at varying concentrations of drug, at the permissive temperature for the conditional inteins, and their phenotypes are scored at different drug concentrations (Table 1). A different reporter system is then employed, such that splicing-proficient, conditionally splicing and splicing-defective intein-β-galactosidase fusions are used to retest compounds that appear to inhibit intein function (i.e., to induce the $TS^-$ phenotype), to ensure that the inhibition is unrelated to the TS reporter, but rather reflects reduced intein function. Compounds that pass the latter test are tested for growth inhibition of Mycobacterial strains (*M. tuberculosis* and BCG). Hence, the TS reporter system is merely an example of a reporter gene which is applicable to the methods of the present invention, but other reporter systems are equally adaptable to the present invention, such as the β-galactosidase reporter system, identified hereinabove.

TABLE 1

TS phenotypes for intein-targeted drug screen

| Intein[a] Variant | No inhibitor[b] | | | | Weak inhibitor[c] | | | | Strong inhibitor[d] | | | |
|---|---|---|---|---|---|---|---|---|---|---|---|---|
| | +THY | −THY | TTM | φ | +THY | −THY | TTM | φ | +THY | −THY | TTM | φ |
| WT intein-TS | + | + | − | $TS^+$ | + | + | − | $TS^+$ | + | − | + | $TS^-$ |
| CS intein-TS | + | + | − | $TS^+$ | + | − | + | $TS^-$ | + | − | + | $TS^-$ |
| SD intein-TS | + | − | + | $TS^-$ | + | − | + | $TS^-$ | + | − | + | $TS^-$ |

[a]WT = wild-type, splicing proficient intein
CS = conditionally splicing intein
SD = splicing-defective intein
[b]No drug, or drug ineffective at inhibiting intein function
[c]Drug that inhibits weakly
[d]Drug that inhibits strongly
[b, c, d]+THY represents minimal medium supplemented with thymine
−THY represents thymineless minimal medium
TTM represents minimal medium supplemented with trimethoprim and thymine
φ represents phenotype
+ represents growth
− represents no growth Further, the skilled artisan can make intein fusions to other sites in the td reporter gene, or one can make fusions to other reporter genes that are capable of monitoring gene function by straightforward microbiological screening methods.

Cloning techniques and methods of inserting genetic point mutations within intein gene sequences are known in the art. Without undue experimentation, the skilled artisan can use intein genes of interest, other than those which are specifically disclosed herein, for use in the present invention.

Further, the skilled artisan can use any art recognized method of detecting the extein product in the practice of the present invention, including standard analytical methods such as SDS-PAGE electrophoresis, chromatographic separation, enzyme complex formation assays, UV and fluorometric methods, immunoaffinity methods and calorimetric methods, without the burden of undue experimentation.

The following Example is provided for illustration and is not to be considered a limitation of the invention.

EXAMPLE

Preparation of TS-Intein Fusions and Analysis of the their Intein Function

Preparation of the td gene with insertion sites for the inteins

Figure 4:
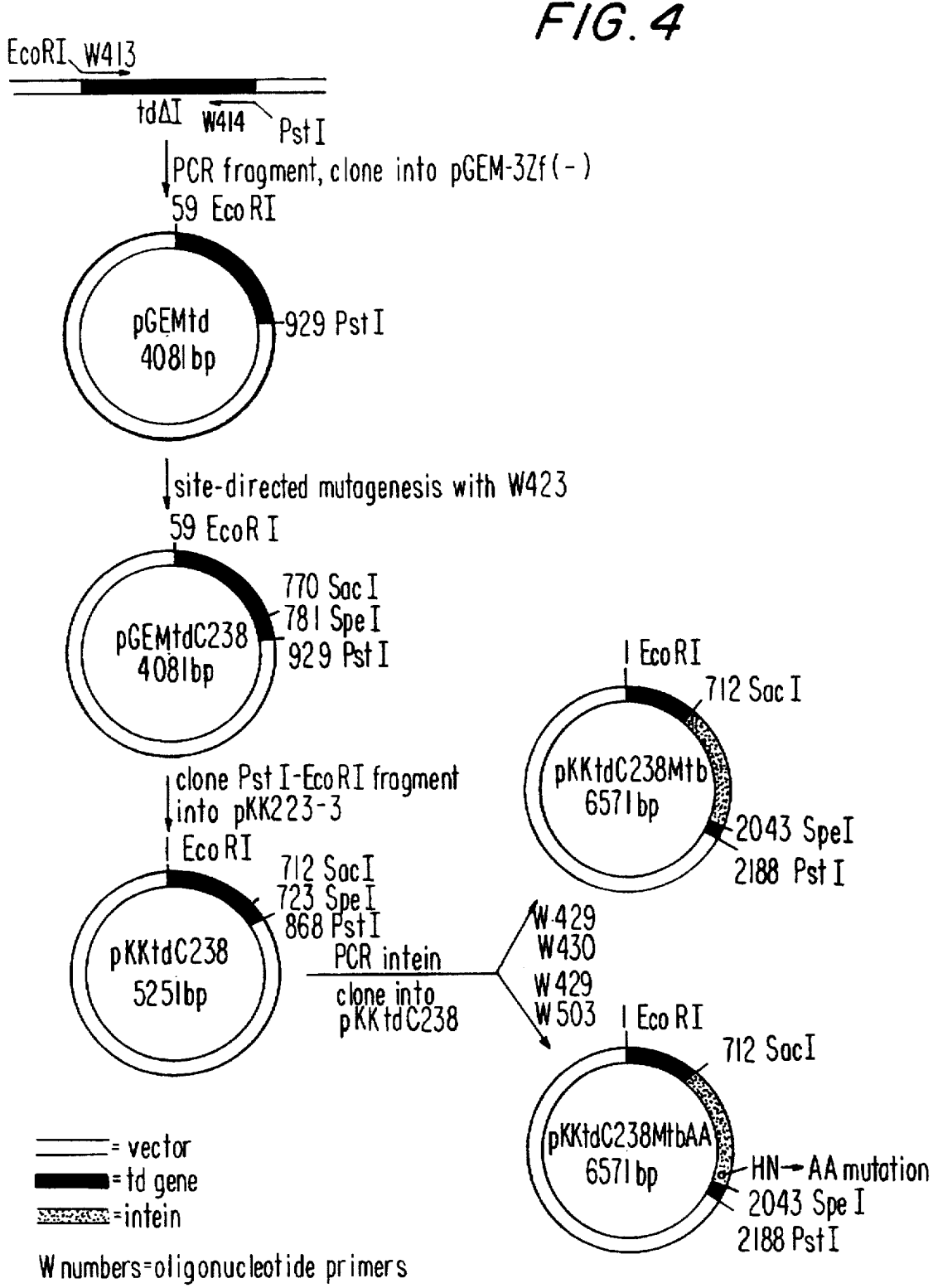
FIG. 4 shows the cloning strategy for pGEMtd, pGEMtdC238, pKKtdC238, pKKtdC238Mtb and pKKtdC238MtbAA.
Figure 5A:
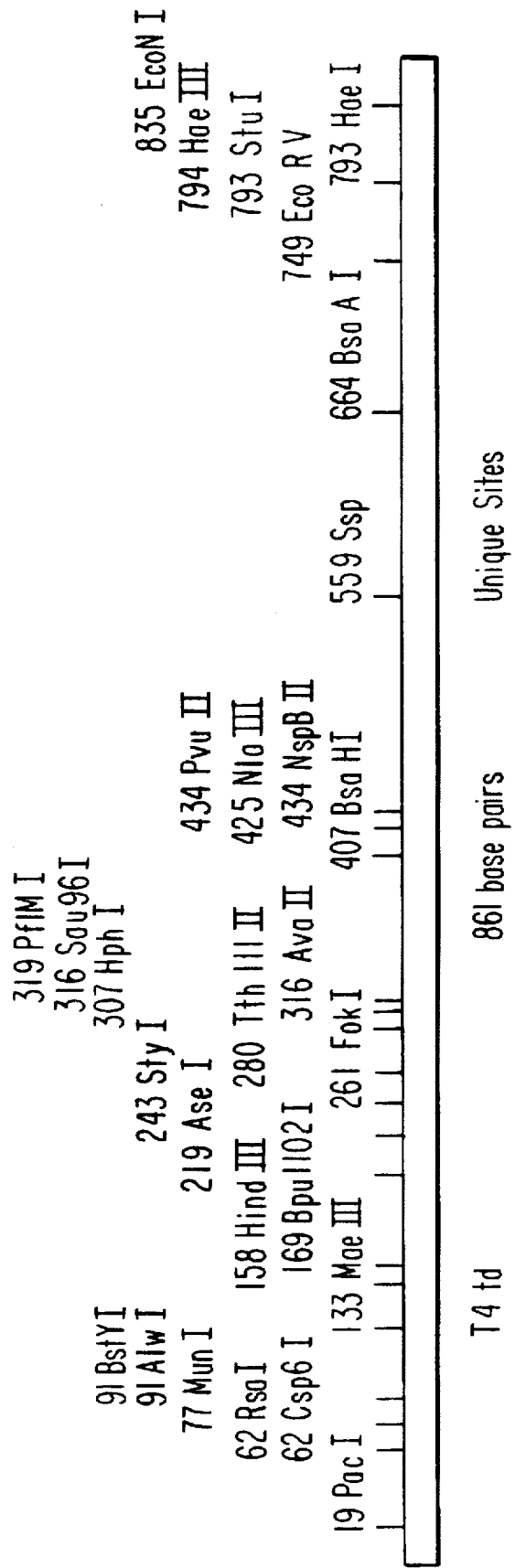
FIG. 5A shows a restriction map of the uninterrupted phage T4 td gene.
Figure 6A:
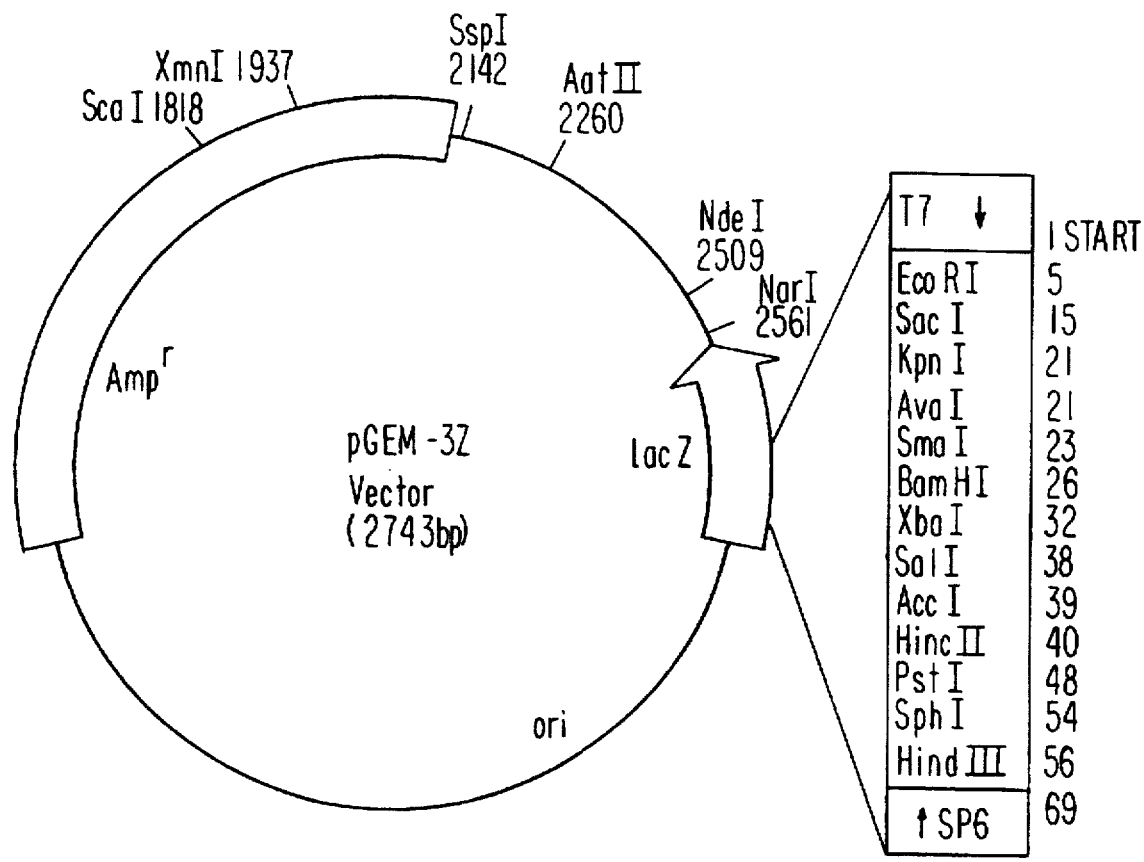
FIG. 6A shows a restriction map of the vector pGEM3-Zf(−)
Figure 7A:
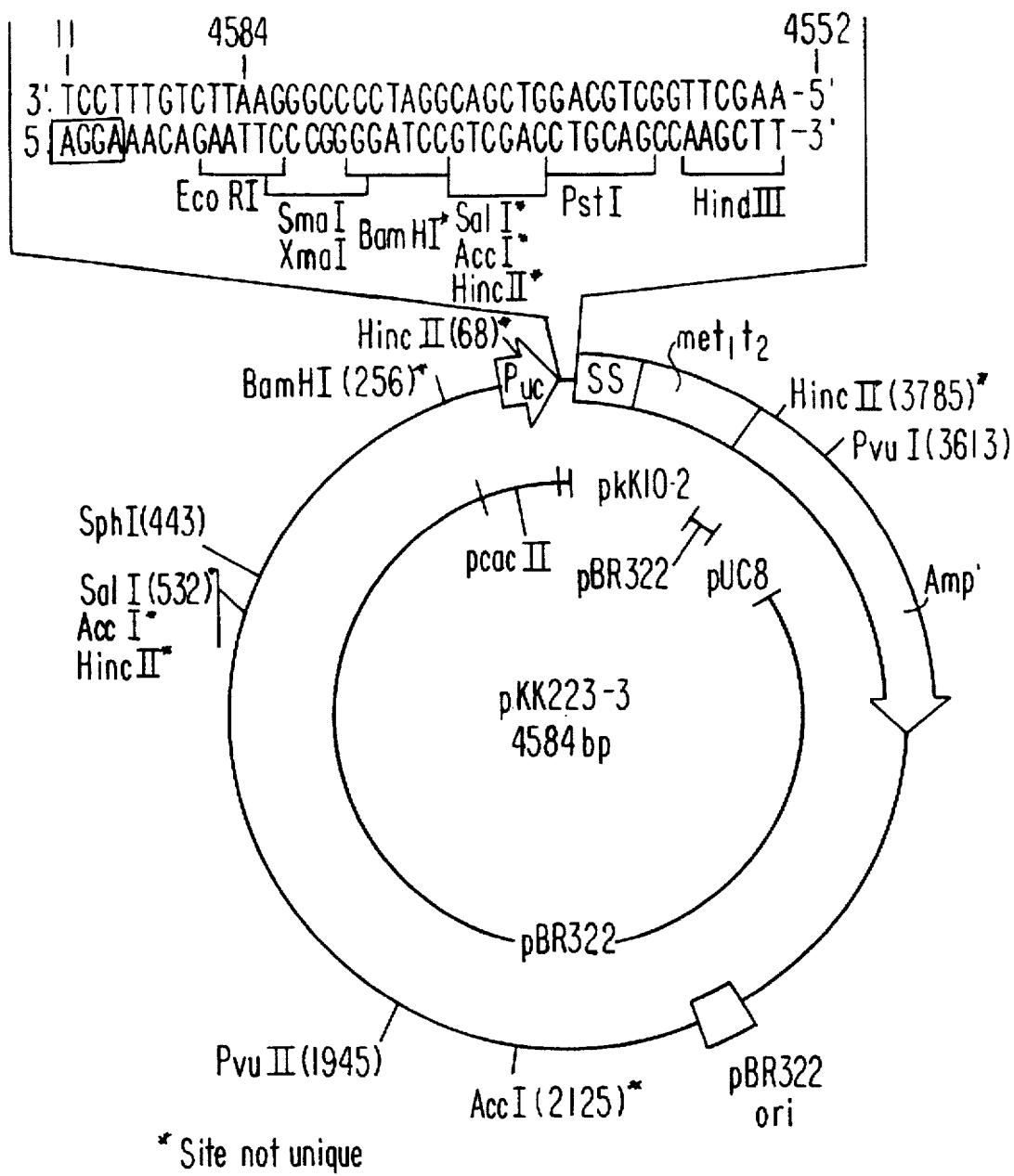
FIG. 7A shows a restriction map of the inducible expression vector pKK223-3.
Figure 8A:
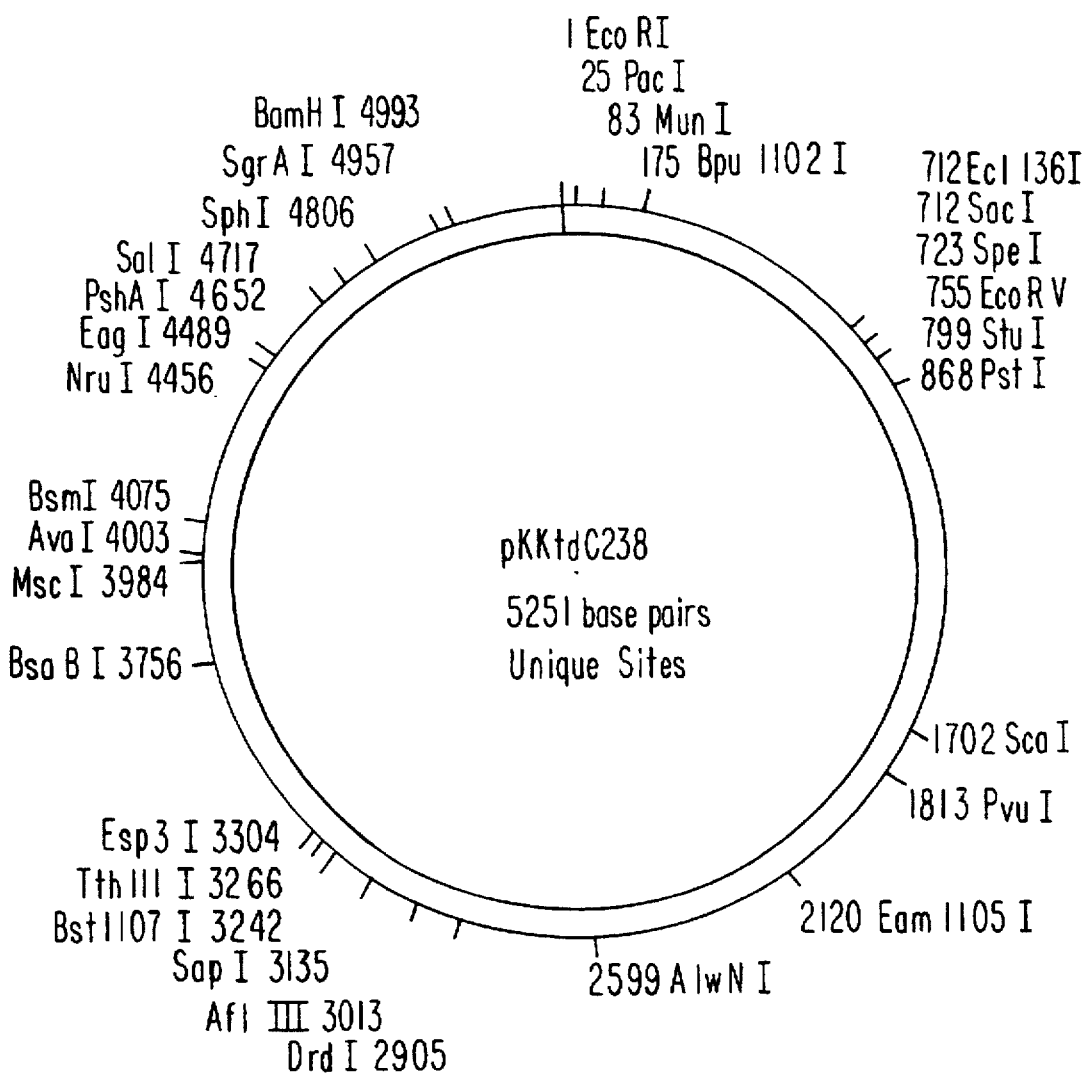
FIG. 8A shows a restriction map of the recipient clone pKKtdC238.

The intronless T4 td gene (FIGS. 4 and 5) was cloned into the vector pGEM3-Zf(–) (FIGS. 4 and 6). This was achieved by amplifying the intronless bacteriophage T4 td gene from pKTdΔI (West et al., 1986) with PCR primers W413 and W414 (Table 2), containing PstI and EcoRI sites, and cloning into the PstI-EcoRI internal of pGEM3-Zf(–). Silent restriction sites were created within the td gene so as to allow the insertion of the intein immediately upstream of a Cys residue in the downstream extein, as required for Mtb intein function (FIGS. 2A and 2B, asterisks), creating an altered reporter gene. A residue was chosen (C238) and equipped with a silent restriction sites by site-directed mutagenesis with oligonucleotide W423 (FIG. 4, Table 2). This created silent SacI and SpeI sites upstream of C238. The phenotype of the td clone containing the silent restriction sites was evaluated in the absence of the intein insertions, and shown to have native TS activity. The altered td gene was recloned into the inducible expression vector pKK223-3 (FIG. 7), to generate recipient clone pKKtdC238 (FIGS. 4 and 8).

Preparation of TS-intein fusions

Figure 9A:
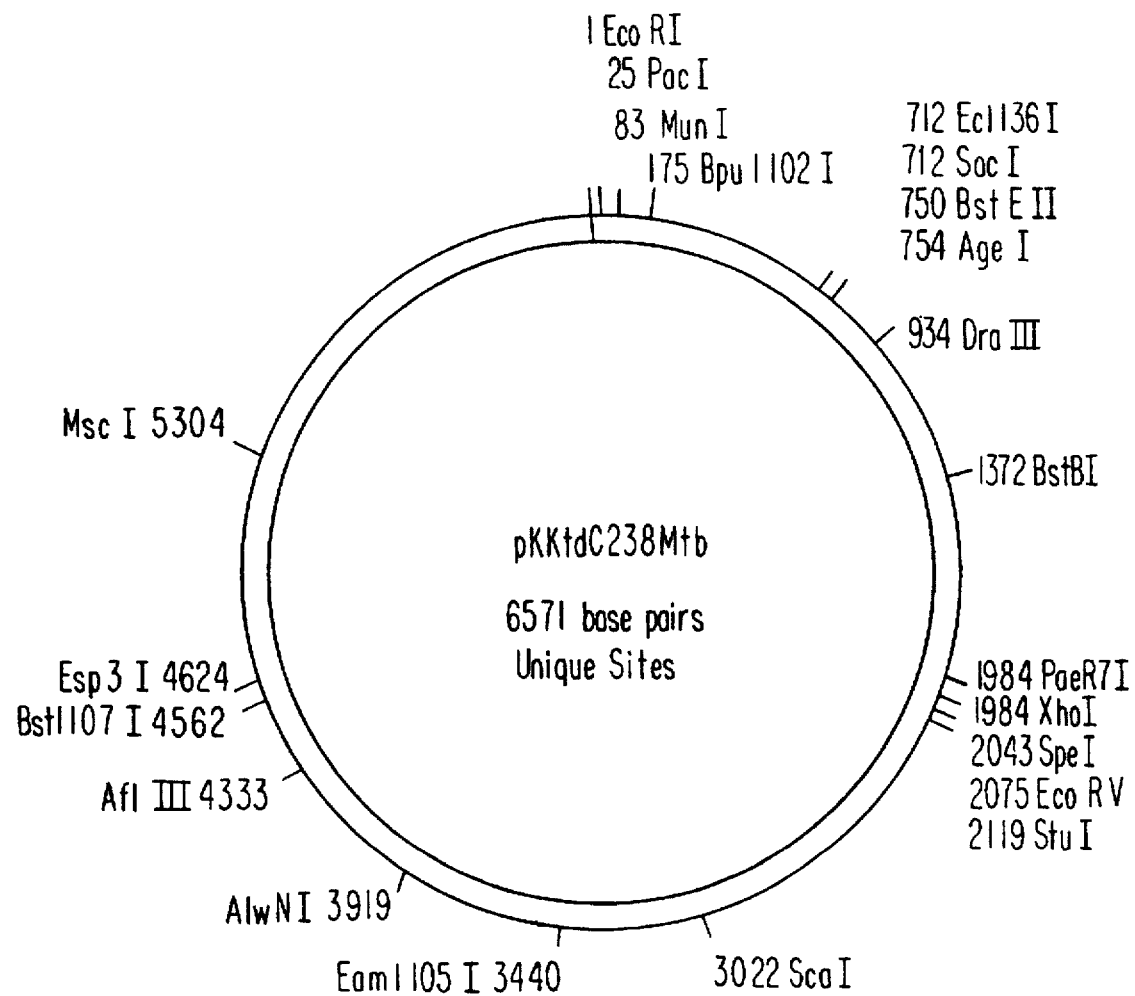
FIG. 9A shows a restriction map of pKKtdC238Mtb, which contains the wild-type intein.
Figure 10A:
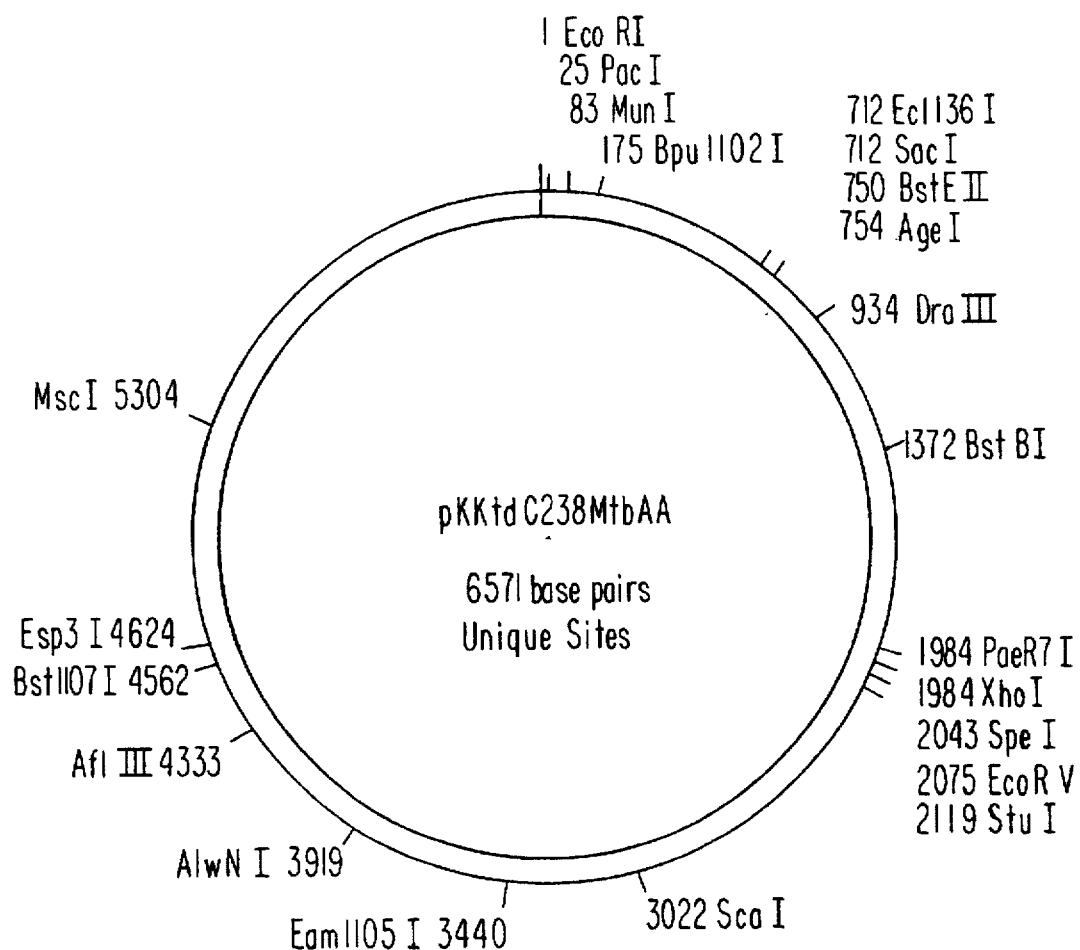
FIG. 10A shows a restriction map of pKKtdC238MtbAA, a splicing deficient mutant.

The recipient clone pKKtdC238 allows the Mtb intein to be inserted into a location preceding a cysteine at 238. The wild-type Mtb intein and a mutated non-splicing intein (with the conserved his(H)–asp(N) residues substituted by ala(A) –ala(A) residues at the carboxy terminus of the intein, MtbAA—FIG. 2A) were inserted into the C238 position of pKKtdC238. This was achieved by amplifying the Mtb intein from *M. tuberculosis* DNA with oligonucleotide primers complementary to the intein, and containing SacI (5' primer) and SpeI (3' primer) sites for cloning into pKKtdC238. To clone the wild-type intein, oligonucleotide primers W429 (5') and W430 (3') were used. To clone the mutant MtbAA intein, the primers W429 (5') and W503 (3') were used, where W503 has all the features of W430 plus the programmed HN to AA mutation (FIG. 4 and Table 2). The newly created clones were named pKKtdC238Mtb (FIG. 9) and pKKtdC238MtbAA (FIG. 10). The C238Mtb pair are the prototypes for testing intein splicing function in the TS reporter background.

In vivo phenotypes, splicing and TS activity

The effectiveness of the splicing reaction in the new extein context was demonstrated using four techniques (FIG. 3). First, the pKKtdC238Mtb clone, containing the wild-type intein, showed a TS+ phenotype, which was indistinguishable from clones containing inteinless td genes. In contrast, the pKKtdC238MtbAA clone containing the non-splicing intein mutant showed a TS– phenotype (FIG. 3A, b–d). Second, a faint band corresponding in size to spliced TS was observed on Coomassie-stained gels (10% acrylamide) with extracts of cells containing the wild-type pKKtdC238Mtb clone (FIG. 3B, lane c), but not the mutant pKKtdC238MtbAA clone (not shown). Third, Western blots using antibodies to TS (polyclonal antibodies directed against the sequence DLIKDIFENGYE (SEQ. ID. NO.:14) (12 amino acid alpha-peptide) corresponding to an N-terminal region of TS) confirmed that the additional bands on the Coomassie gels were, in fact, spliced TS (FIG. 3C, lanes b and c). The presence of unspliced precursor was also noted in both the stained gels (FIG. 3B, lane c) and Western blots (FIG. 3C, lane c).

Finally, an [$^3$H]-FdUMP activity assay for TS function, where the FdUMP (5-fluoro-2'-deoxyuridine 5'-monophosphate) forms a covalent complex with active TS, was performed. The FdUMP assay was performed as described by Belfort et al., 1983, by incubating crude cell extracts containing thymidylate synthase (TS) with a tritium-labeled substrate analog, [$^3$H]-FdUMP, in the presence of a cofactor, methylenetetrahydrofolate. The labeled covalent [$^3$H]-FdUMP-TS complex was then separated on a 10% SDS-PAGE gel and visualized by fluorography. The assay showed conclusively that an active TS was expressed in cells harboring the wild-type pKKtdC238Mtb clone, but not the mutant pKKtdC238MtbAA clone (FIG. 3D, lanes c and d), and that the relative size of the enzyme was equal to that which was expected for the spliced product. These results clearly indicate that the TS phenotypes are viable as a reporter of intein function.

Mutant libraries

Using error-prone PCR a library of randomly mutated Mtb inteins was created with restriction sites appropriate for cloning into the aforementioned locations of the td gene. Random mutagenesis was performed on the intein using error-prone PCR with primers W429 and W430 and Taq DNA polymerase, which lacks 3'–5' exonucleolytic editing activity, which, therefore, generates mutation-rich products (Zhou et al., 1991). Further, the inteins were cloned into the td gene at the SacI and SpeI sites of pKKtdC238 with high efficiency. Enough DNA was created in a single mutagenic reaction to evaluate approximately $10^7$ mutant clones. The premise of the screening system is that if the intein does not splice out of the TS protein, TS will be inactive. Therefore, by placing the intein coding sequence into the td gene and transforming it into TS-deficient cells, one can select for intein mutants that do splice under some conditions (the TS+ phenotype), but do not splice under other conditions (the TS– phenotype).

From the first $10^5$ clones, two temperature-sensitive intein mutants were isolated by selecting TS– clones on TTM at 37° C. and screening these for the TS+ phenotype at 23° C. One of these mutants is shown in FIG. 3A (segment e), with the desired TS– phenotype at 37° C. (growth on TTM media but not on –THY media lacking thymine), and TS+ phenotype at 23° C. (growth on –THY but not on TTM media). The two mutants have slightly different phenotypes with respect to their temperature transitions, and in both cases, recloning the intein into pKKtdC238 conferred the phenotype in the new TS extein context.

These results indicate that each mutational change is different, and that they each reside within the intein, as anticipated. The two mutational changes consist of (where the amino acids are numbered from Cys 1 of intein):

| Mutant | Position | Change | Name |
|---|---|---|---|
| 1 | 220 | Glu to Lys | E220K |
| 2 | 41 | His to Arg | H41R |

The DNA and protein sequences of the Mtb intein, and sequence changes of two conditionally splicing mutants are shown in FIG. 11.

To sequence mutated inteins, PCR was used to amplify the inteins with td-specific primers W270 and W451 (Table 2), flanking the intein insertion site. The PCR fragments were purified on a 1% agarose gel, and subjected to sequencing on an Applied Biosystems automated sequencer with a set of sequencing primers (W270, W366, W367, W369, W370, W371, W372, W373, W374, W451 and W579, shown in Table 2).

Depending upon the most desirable temperature for the drug screen, mutants with different temperature transitions can be readily isolated. For example, for screens conducted at 37° C., mutant inteins that are functional at this temperature, but inactive at 42° C., would be desirable.

Further, these results verify the efficacy of the genetic system of the present invention in isolating intein mutants, and its potential for screening drugs targeted against inteins.

2. Belfort, M., Moelleken, A., Maley, G. F., and Maley, F. (1983). Purification and properties of T4 phage thymidylate synthetase produced by the cloned gene in an amplification vector. J. Biol. Chem. 258, 2045-2051.
3. Belfort, M. et al., 1995. Prokaryotic Introns and Inteins: A panoply of form and function. J. Bacter. 177: 3897-3903.
4. Clarke, N. D. (1994). A proposed mechanism for the self-splicing of proteins. Proc. Natl. Acad. Sci., 91: 11084-11088.
5. Colston, M. J. and Davis, E. O. (1994). The ins and outs of protein splicing elements. Mol. Microbiol. 12, 359-363.
6. Cooper, A. A. and Stevens, T. H. (1993). Protein splicing: Excision of intervening sequences at the protein level. Bioessays 15, 667-674.
7. Cooper, A. A. and Stevens, T. H. (1995). Protein splicing: self-splicing of genetically mobile elements at the protein level. TIBS 351-356.
8. Dalgaard, J. (1994). Mobile introns and inteins: friend or foe? Trends in Genetics, 10: 306-307.
9. Davis, E. D. et al., (1991). Novel structure of the recA Locus of *mycobacterium tuberculosis* implies processing of the gene product. J. Bacter. 173: 5653-5662.
10. Davis, E. O., Jenner, P. J., Brooks, P. C., Colston, M. J., and Sedgwick, S. G. (1992). Protein splicing in the

TABLE 2

Oligonucleotides for Cloning and Sequencing (5' to 3')

td Cloning Primers:

W413 SEQ. ID. NO: 15 TCCGAATTCATGAAACAATACCAAGATTTA
W414 SEQ. ID. NO: 16 CCCGGATCCATCGATCTGCAGTTACACCGCCATCTTTCCTTTAAT
Mutagenic Oligo for SacI-SpeI generation in td:

W423 SEQ. ID. NO: 17 ACCACTTATTACTAGTTCACAGAGCTCTTTACCTTC
Primers for Cloning and Insertion of Mtb Intein:

W429 SEQ. ID. NO: 18 GAACCTAAAGAGCTCTGCCTCGCAGAGGGCACTCGG
W430 SEQ. ID. NO: 19 ACTTATTACTAGTTCACAGTTGTGCACGACAACCCCTTCGGGC
Primer (3') to generate MtbAA (mutagenic equivalent to W430):

W530 SEQ. ID. NO: 20 ACTTATTACTAGTTCACAGGCGGCCACGACAACCCTTCGGCGACGAG
Mtb Intein Sequencing Primers:

W270 SEQ. ID. NO: 21 CCGCCATCTTTCCTTTAATAGGAG
W451 SEQ. ID. NO: 22 GAACAATGTAAAGAAATTTTGAGGC
W366 SEQ. ID. NO: 23 GGGTGGCGCAACCGCGACGCTTCG
W367 SEQ. ID. NO: 24 CGTGGGAGAAGACGATTCCGAATTGG
W369 SEQ. ID. NO: 25 GGATGACAAATTCCTGCACGACAT
W370 SEQ. ID. NO: 26 GCCCGCCGCGTTGGCAGCACTTCT
W371 SEQ. ID. NO: 27 GGAATCGCCTGGATAAGCGCGGCA
W372 SEQ. ID. NO: 28 CGAACAGGCCGAAGAGCAGATTGC
W373 SEQ. ID. NO: 29 GCCAAGCAGCCGGGCATGATCCGC
W374 SEQ. ID. NO: 30 GCGTTCCCTGGTCGAACCAGGACA
W579 SEQ. ID. NO: 31 GTATGGATAACGTCACGGCATTCG

Having thus described in detail certain preferred embodiments of the present invention, it is to be understood that the invention defined by the appended claims is not to be limited by particular details set forth in the above description, as many apparent variations thereof are possible without departing from the spirit or scope thereof.

REFERENCES

1. Belfort, M., Ehrenman, K., and Chandry, P. S. (1990). Genetic and molecular analysis of RNA splicing in *Escherichia coli*. Methods Enzymol. 181, 521-539.

maturation of the *M. tuberculosis* RecA protein: A mechanism for tolerating a novel class of intervening sequence. Cell 71, 201-210.
11. Davis, E. O., Sedgwick, S. G., and Colsten, M. J. (1991). Novel structure of the RecA locus of *Mycobacterium tuberculosis* implies processing of the gene product. J. Bacteriol. 173, 5653-5662.
12. Davis, E. O., Thangaraj, H. S., Brooks, P. C., and Colston, M. J. (1994). Evidence of selection for protein introns in the RecAs of pathogenic mycobacteria. EMBO J. 13, 699-703.

13. Fsihi, H., Vincent, V., and Cole, S. T. (1996). Homing events in the gyrA gene of some mycobacteria. Proc. Natl. Acad. Sci. USA 93, 3410–3415.
14. Gu, H. H., Xu, J., Gallagher, M., and Dean, G. E. (1993). Peptide splicing the vacuolar ATPase subunit A from Candida tropicalis. J. Biol. Chem. 268, 7372–7381.
15. Perler, F. B., Davis, E. O., Dean, G. E., Gimble, F. S., Jack, W. E., Neff, N., Noren, C. J., Thorner, J., and Belfort, M. (1994). Protein splicing elements: inteins and exteins—a definition of terms and recommended nomenclature. Nucl. Acids Res. 22, 1125–1127.
16. Pietrokovski, S. (1994). Conserved sequence features of inteins (protein introns) and their use in identifying new in identifying new inteins and related proteins. Protein Science, 3: 2340–2350.
17. Pietrokovski, S. (1996). A new intein in cyanobacteria and its significance for the spread of inteins. Trends in Genetics 12: 287–288.
18. Shao, Y. et al., (1995). Protein splicing: Characterization of the Aminosuccinimide Residue at the Carboxyl Terminus of the Excised Intervening Sequence. Biochem. 34: 10844–10850.
19. West, D. K., Belfort, M., Maley, G. F. and Maley, F. (1986). Cloning and expression of an intron-deleted phage T4 td gene. J. Biol. Chem. 261: 13446–13450.
20. Xu, M., Southworth, M. W., Mersha, F. B., Hornstra, L. J., and Perler, F. B. (1993). In vitro protein splicing of purified precursor and the identification of a branched intermediate. Cell. 75: 1371–1377.
21. Xu, M., Comb, D. G., Paulus, H., Noren, C. J., Shao, Y., and Perler, F. B., (1994). Protein splicing: An analysis of the intermediate and its resolution by succinimide formation. EMBO J. 13: 5517–5522.
22. Zhou, Y., Zhang, X. and Ebright, R. H. (1991). Random mutagenesis of gene-sized DNA molecules by use of PCR with taq DNA polymerase. Nucleic Acids Res. 19: 6052.

What I claim is:

1. A method for screening an agent for antimicrobial activity against a microbial pathogen having an intein in a gene encoding a protein which facilitates growth of said pathogen comprising detecting inhibition of said intein by steps comprising:

preparing recombinant clones of an inducible expression vector containing: (a) an altered reporter gene comprising a silent restriction site within a reporter gene, and (b) said intein;

detecting the production of extein product of said intein by said recombinant clones in the presence of varying concentrations of said agent;

wherein reduced production of said extein product indicates inhibition of said intein, and antimicrobial activity of said agent against said pathogen.

2. The method of claim 1 wherein said detecting is selected from the group consisting of gel electrophoresis, Western blot, in vivo phenotype characterization and complex formation assay.

3. The method of claim 1 wherein said reporter gene is the phage T4 td gene.

4. The method of claim 3 wherein said intein is the Mtb RecA intein from the RecA protein of *Mycobacterium tuberculosis*.

5. The method of claim 4 wherein said inducible expression vector containing an altered reporter gene comprising a silent restriction site within a reporter gene, but without said intein, is pKKtdC238.

6. The method of claim 5 wherein the preparing of said recombinant clones comprises cloning said intein gene into said pKKtdC238 and results in clones pKKtdC238Mtb and pKKtdC238MtbAA.

7. The method of claim 4 wherein said detecting is performed in selective medium with *Escherichia coli* thyA cells deficient in host thymidylate synthase (TS).

8. The method of claim 5 wherein said intein is inserted, preceding cystein 238 of said phage T4 td gene, into said inducible expression vector containing said altered reporter gene comprising a silent restriction site within said phage T4 td reporter gene.

9. The method of claim 5 wherein the most C-terminal residues of said Mtb recA intein, Histidine-Asparagine, are substituted by Alanine-Alanine, resulting in a mutated non-splicing intein.

10. The method of claim 7 wherein said medium is deficient in thymine.

11. The method of claim 7 wherein said medium comprises trimethoprim and thymine.

12. A method for screening an agent for antimicrobial activity against a microbial pathogen having an intein in a gene encoding a protein which facilitates growth of said pathogen comprising detecting inhibition of said intein by monitoring intein function, which comprises:

creating a silent restriction site within a reporter gene which results in an altered reporter gene;

cloning said altered reporter gene into an inducible expression vector;

cloning said intein into said inducible expression vector containing said altered reporter gene to generate recombinant clones; and detecting the production of extein product of said intein by said recombinant clones in the presence of varying concentrations of said agent;

wherein reduced production of said extein product indicates inhibition of said intein, and antimicrobial activity of said agent against said pathogen.

13. The method of claim 12 wherein said detecting is selected from the group consisting of gel electrophoresis, Western blot, in vivo phenotype characterization, and complex formation assay.

14. The method of claim 12 wherein said reporter gene is the phage T4 td gene.

15. The method of claim 14 wherein said intein of interest is the Mtb RecA intein from the RecA protein of *Mycobacterium tuberculosis*.

16. The method of claim 15 wherein said inducible expression vector containing an altered reporter gene comprising a silent restriction site within a reporter gene, but without said intein, is pKKtdC238.

17. The method of claim 16 wherein said cloning of said intein into said pKKtdC238 results in clones pKKtdC238Mtb and pKKtdC238MtbAA.

18. The method of claim 12 wherein said detecting is performed in selective medium with *Escherichia coli* thyA cells deficient in host thymidylate synthase (TS).

19. The method of claim 14 wherein said intein is inserted, preceding cystein 238 of said phage T4 td gene, into said inducible expression vector containing said altered reporter gene comprising a silent restriction site within said phage T4 td reporter gene.

20. The method of claim 15 wherein the most C-terminal residues of said Mtb RecA intein, Histidine-Asparagine, are substituted by Alanine-Alanine, resulting in a mutated non-splicing intein.

21. The method of claim 18 wherein said medium is deficient in thymine.

22. The method of claim 18 wherein said medium comprises trimethoprim and thymine.

23. A method for screening an agent for antimicrobial activity against a microbial pathogen having an intein in a gene encoding a protein which facilitates growth of said pathogen comprising detecting inhibition of said intein using conditional splicing variants of said intein, which comprises:

creating a silent restriction site within a reporter gene which results in an altered reporter gene;

cloning said altered reporter gene into an inducible expression vector;

cloning said conditional splicing intein variants into said inducible expression vector containing said altered reporter gene to generate recombinant clones; and detecting the production of extein product of said conditional splicing intein variants by the recombinant clones in the presence of varying concentrations of said agent, and at varying temperatures;

wherein reduced production of said extein product of said conditional splicing intein variants indicates inhibition of said intein, and antimicrobial activity of said agent against said pathogen.

24. The method of claim 23 wherein said detecting is selected from the group consisting of gel electrophoresis, Western blot, in vivo phenotype characterization, and complex formation assay.

* * * * *

UNITED STATES PATENT AND TRADEMARK OFFICE
CERTIFICATE OF CORRECTION

PATENT NO. : 5,795,731
DATED : August 18, 1998
INVENTOR(S) : Marlene Belfort

It is certified that error appears in the above-identified patent and that said Letters Patent is hereby corrected as shown below:

Column 1, line 5, insert the following:

--This invention was made with government support under Grant No. GM44844 awarded by National Institutes of Health. The government has certain rights in the invention.--

Signed and Sealed this

Twenty-second Day of June, 1999

Attest:

Q. TODD DICKINSON

*Attesting Officer*   *Acting Commissioner of Patents and Trademarks*

UNITED STATES PATENT AND TRADEMARK OFFICE
CERTIFICATE OF CORRECTION

| | | |
|---|---|---|
| PATENT NO. | : 5,795,731 | Page 1 of 1 |
| APPLICATION NO. | : 08/702902 | |
| DATED | : August 18, 1998 | |
| INVENTOR(S) | : Marlene Belfort | |

It is certified that error appears in the above-identified patent and that said Letters Patent is hereby corrected as shown below:

Column 1, line 16, please insert the following paragraph:

--STATEMENT REGARDING FEDERALLY SPONSORED RESEARCH OR DEVELOPMENT

This invention was made with government support under GM44844 awarded by the National Institutes of Health. The government has certain rights in the invention.--

Signed and Sealed this
Eighth Day of May, 2012

David J. Kappos
*Director of the United States Patent and Trademark Office*